US008796182B2

(12) United States Patent
Steinthorsdottir et al.

(10) Patent No.: US 8,796,182 B2
(45) Date of Patent: Aug. 5, 2014

(54) GENETIC MARKERS ASSOCIATED WITH RISK OF DIABETES MELLITUS

(75) Inventors: Valgerdur Steinthorsdottir, Reykjavik (IS); Gudmar Thorleifsson, Reykjavík (IS); Daniel Gudbjartsson, Reykjavík (IS); Gisli Masson, Reykjavik (IS); Augustine Kong, Reykjavík (IS)

(73) Assignee: deCODE Genetics ehf., Reykjavik (IS)

( * ) Notice: Subject to any disclaimer, the term of this patent is extended or adjusted under 35 U.S.C. 154(b) by 0 days.

(21) Appl. No.: 13/382,620

(22) PCT Filed: Jul. 9, 2010

(86) PCT No.: PCT/IS2010/050007
§ 371 (c)(1),
(2), (4) Date: May 8, 2012

(87) PCT Pub. No.: WO2011/004405
PCT Pub. Date: Jan. 13, 2011

(65) Prior Publication Data
US 2012/0220477 A1   Aug. 30, 2012

(30) Foreign Application Priority Data

Jul. 10, 2009 (IS) .............................. 8836

(51) Int. Cl.
*C40B 30/04* (2006.01)
*G06F 19/10* (2011.01)
*C12Q 1/68* (2006.01)

(52) U.S. Cl.
USPC .............................. 506/7; 435/6.1

(58) Field of Classification Search
None
See application file for complete search history.

(56) References Cited

U.S. PATENT DOCUMENTS

| 4,376,110 | A  | 3/1983  | David et al.    |
|-----------|----|---------|-----------------|
| 5,223,409 | A  | 6/1993  | Ladner et al.   |
| 5,288,644 | A  | 2/1994  | Beavis et al.   |
| 5,445,934 | A  | 8/1995  | Fodor et al.    |
| 5,700,637 | A  | 12/1997 | Southern        |
| 5,744,305 | A  | 4/1998  | Fodor et al.    |
| 5,945,334 | A  | 8/1999  | Besemer et al.  |
| 6,054,270 | A  | 4/2000  | Southern        |
| 6,300,063 | B1 | 10/2001 | Lipshutz et al. |
| 6,429,027 | B1 | 8/2002  | Chee et al.     |
| 6,733,977 | B2 | 5/2004  | Besemer et al.  |
| 6,858,394 | B1 | 2/2005  | Chee et al.     |
| 7,364,858 | B2 | 4/2008  | Barany et al.   |
| 7,585,630 | B2 | 9/2009  | Grant           |
| 2002/0150896 | A1 | 10/2002 | Polonsky et al. |
| 2003/0092019 | A1 | 5/2003  | Meyer et al.    |
| 2006/0286588 | A1 | 12/2006 | Grant           |
| 2009/0275043 | A1 | 11/2009 | Grant           |
| 2010/0086921 | A1 | 4/2010  | Steinthorsdottir et al. |
| 2012/0149016 | A1 | 6/2012  | Grant           |

FOREIGN PATENT DOCUMENTS

| EP | 373 203 A1       | 6/1990  |
|----|------------------|---------|
| EP | 619 321 A1       | 10/1994 |
| WO | WO-90/02809 A1   | 3/1990  |
| WO | WO-91/17271 A1   | 11/1991 |
| WO | WO-92/01047 A1   | 1/1992  |
| WO | WO-92/09690 A2   | 6/1992  |
| WO | WO-92/15679 A1   | 9/1992  |
| WO | WO-92/18619 A1   | 10/1992 |
| WO | WO-92/20791 A1   | 11/1992 |
| WO | WO-93/01288 A1   | 1/1993  |
| WO | WO-03/024447 A1  | 3/2003  |
| WO | WO-2004/041193 A2| 5/2004  |
| WO | WO-2004/042358 A2| 5/2004  |
| WO | WO-2004/065370 A1| 8/2004  |
| WO | WO-2006/137085 A1| 12/2006 |
| WO | WO-2007/048236 A1| 5/2007  |
| WO | WO-2007/084236 A2| 7/2007  |
| WO | WO-2008/065682 A2| 6/2008  |

OTHER PUBLICATIONS

Andersson et al., Type 2 diabetes risk alleles near ADCY5, CDKAL1 and HHEX-IDE are associated with reduced birthweight, Diabetologia, 53(9):1908-16 (2010).
Bell et al., Methylation of a CTCF-dependent boundary controls imprinted expression of the Igf2 gene, Nature, 405(6785):482-5 (2000).
Bell et al., The protein CTCF is required for the enhancer blocking activity of vertebrate insulators, Cell 98(3):387-96 (1999).
Bitton et al., The Framingham Heart Study's impact on global risk assessment, Prog. Cardiovasc. Dis., 53(1):68-78 (2010).
Brunner et al., Distinct DNA methylation patterns characterize differentiated human embryonic stem cells and developing human fetal liver, Genome Res., 19(6):1044-56 (2009).
Cauchi et al., Analysis of novel risk loci for type 2 diabetes in a general French population: the D.E.S.I.R. study, J. Mol. Med. (Berl.), 86(3):341-8 (2008).
Cauchi et al., Post genome-wide association studies of novel genes associated with type 2 diabetes show gene-gene interaction and high predictive value, PLoS One, 3(5):e2031 (2008).
Chen et al., The evolution of gene regulation by transcription factors and microRNAs, Nat. Rev. Genet., 8(2):93-103 (2007).

(Continued)

*Primary Examiner* — Stephanie K Mummert
*Assistant Examiner* — Jonah Smith
(74) *Attorney, Agent, or Firm* — Marshall, Gerstein & Borun LLP

(57) ABSTRACT

The invention relates to variants that predispose to risk of type 2 diabetes, basal cell carcinoma and breast cancer. It has been discovered that certain genetic variants confer risk of these diseases when inherited from one parent, but not the other. The invention provides methods of disease management, including diagnostic methods, utilizing such parental origin effects.

16 Claims, 5 Drawing Sheets

(56) References Cited

OTHER PUBLICATIONS

Chidambaram et al., Replication of recently described type 2 diabetes gene variants in a South Indian population, Metabolism, 59 12:1760-6 (2010).

Chistiakov et al., The carriage of risk variants of CDKAL1 impairs beta-cell function in both diabetic and non-diabetic patients and reduces response to non-sulfonylurea and sulfonylurea aqonists of the pancreatic KATP channel, Acta Diabetol., 48(3):227-35 (2011).

Cho et al., Type 2 diabetes-associated genetic variants discovered in the recent genome-wide association studies are related to gestational diabetes mellitus in the Korean population. Diabetologia, 52(2):253-61 (2009).

Cuddapah et al., Global analysis of the insulator binding protein CTCF in chromatin barrier regions reveals demarcation of active and repressive domains, Genome Res., 19(1):24-32 (2009).

Dehwah et al., CDKAL1 and type 2 diabetes: a global meta-analysis, Genet. Mol. Res., 9(2)1109-20 (2010).

Dobrikova et al., Relationship of the CDKAL1 and KCNQ1 gene polymorphisms to the age at diagnosis of type 2 diabetes in the Slovakian population], Vnitr. Lek., 57(2):155-8 (2011) Abstract Only.

Ekelund et al., Genetic prediction of postpartum diabetes in women with gestational diabetes mellitus, Diabetes Res. Clin. Pract. 97 3:394-8 (2012).

Filippova et al., Boundaries between chromosomal domains of X inactivation and escape bind CTCF and lack CpG methylation during early development, Dev. Cell, 8(1):31-42 (2005).

Florez, The new type 2 diabetes gene TCF7L2, Curr. Opin. Clin. Nutr. Metab Care, 10:391-6 (2007).

Genetic Information and Voluntary Life Insurance, Issue Brief: American Academy of Actuaries (Spring 1998).

Good Laboratory Practices for Molecular Genetic Testing for Heritable Diseases and Conditions, Morbidity and Mortality Weekly Report, 58(RR-6), US Department of Health & Human Services, Centers for Disease Control & Prevention (Jun. 12, 2009).

Grys, Actuarial considerations on genetic testing, Philos. Trans. R. Soc. Lond B. Biol. Sci., 352(1357):1057-61 (1997).

Gupta et al., Association analysis of 31 common polymorphisms with type 2 diabetes and its related traits in Indian sib pairs, Diabetologia, 55(2):349-57 (2012).

Hanson et al., Strong parent-of-origin effects in the association of KCNQ1 variants with type 2 diabetes mellitus in American Indians, Diabetes (Apr. 29, 2013) (E-pub ahead of print).

Hertel et al., Genetic analysis of recently identified type 2 diabetes loci in 1,638 unselected patients with type 2 diabetes and 1,858 control participants from a Norwegian population-based cohort (the HUNT study), Diabetologia, 51(6):971-7 (2008).

Horikawa at al., Replication of genome-wide association studies of type 2 diabetes susceptibility in Japan, J. Clin. Endocrinol. Metab., 93(8):3136-41 (2008).

Horikoshi et al:, Variations in the HHEX gene are associated with increased risk of type 2 diabetes in the Japanese population, Diabetologia, 50(12):2461-6 (2007).

Kim et al., Analysis of the vertebrate insulator protein CTCF-binding sites in the human genome, Cell, 128(6):1231-45 (2007).

Liu et al., Genetic variants of cyclin-dependent kinase 5 regulatory subunit associated protein 1-like 1 and transcription factor 7-like 2 are not associated with polycystic ovary syndrome in Chinese women, Gynecol. Endocrinol., 26(2):129-34 (2010).

Lu et al., Genetic variants on chromosome 6p21.1 and 6p22.3 are associated with type 2 diabetes risk: a case-control study in Han Chinese, J. Hum. Genet., 57(5):320-5 (2012).

Myers et al., Optimal alignments in linear space, CABIOS, 4(1):11-17 (1988).

National Human Genome Research Institute, A Catalog of Published Genome-Wide Association Studies, published online at http://www.genome.gov/gwastudies, (Feb. 12, 2013).

NCBI dbSNP Build 137 Summary, published online at http://www.ncbi.nlm.nih.gov/SNP/snp_summary.cgi (2012).

Nemr et al., Replication study of common variants in CDKAL1 and CDKN2A/2B genes associated with type 2 diabetes in Lebanese Arab population, Diabetes Res. Clin. Pract., 95(2):e37-40 (2012).

Omori et al., Association of CDKAL1, IGF2BP2, CDKN2A/B, HHEX, SLC30A8, and KCNJ11 with susceptibility to type 2 diabetes in a Japanese population, Diabetes, 57(3):791-5 (2008).

Pearson et al., Improved tools for biological sequence comparison, PNAS, 85:2444-8 (1988).

Qi et al., Diabetes genetic predisposition score and cardiovascular complications among patients with type 2 diabetes, Diabetes Care, 36(3):737-9 (2013).

Rich et al., Using a quantitative measure of diabetes risk in clinical practice to target and maximize diabetes prevention interventions, Clinical Diabetes, 31(2):82-9 (2013).

Ruchat et al., Improvements in glucose homeostasis in response to regular exercise are influenced by the PPARG Pro12Ala variant: results from the HERITAGE Family Study, Diabetologia, 53(4):679-89 (2010).

Ryoo et al., Heterogeneity of genetic associations of CDKAL1 and HHEX with susceptibility of type 2 diabetes mellitus by gender, Eur. J. Hum. Genet., 19(6):672-5 (2011).

Schoenherr et al., CTCF maintains differential methylation at the Igf2/H19 locus, Nat. Genet., 33(1):66-9 (2003).

Schroner et al., Variation in CDKAL1 gene is associated with therapeutic response to sulphonylureas, Physiol. Res., 61(2):177-83 (2012).

Silberberg, Definition of "natural law" IN: Chemistry: The Molecular Nature of Matter and Change, Fourth Edition, New York, NY: McGraw Hill (2006).

Sladek et al., A genome-wide association study identifies novel risk loci for type 2 diabetes, Nature, 445:828-30 (2007).

Tabara et al., Replication study of candidate genes associated with type 2 diabetes based on genome-wide screening, Diabetes, 58(2):493-8 (2009).

Thompson et al., Applications of antisense and siRNAs during preclinical drug development, Drug Discovery Today, 7:912-7 (2002).

Xu et al., Combined effects of 19 common variations on type 2 diabetes in Chinese: results from two community-based studies, PLoS One, 5(11):e14022 (2010).

Zhao et al., Examination of type 2 diabetes loci implicates CDKAL1 as a birth weight gene, Diabetes, 58(10):2414-8 (2009).

Zick et al., Genetic testing for Alzheimer's disease and its impact on insurance purchasing behavior, Health Affairs, 24(3):483-90 (2005).

Agami, RNAi and related mechanisms and their potential use for therapy, Curr. Opin. Chem. Biol., 6:829-34 (2002).

Altschul et al., Gapped BLAST and PSI-BLAST: a new generation of protein database search programs, Nucleic Acids Res., 25:3389-402 (1997).

Altshuler et al.,The common PPARgamma Pro12Ala polymorphism is associated with decreased risk of type 2 diabetes, Nat. Genet., 26(1):76-80 (2000).

Amarzguioui et al., Approaches for chemically synthesized siRNA and vector-mediated RNAi, FEBS Lett., 579:5974-81 (2005).

Amos et al., Genome-wide association scan of tag SNPs identifies a susceptibility locus for lung cancer at 15q25.1, Nat. Genet., 40:616-22 (2008).

Amos et al., The rising global burden of diabetes and its complications: estimates and projections to the year 2010, Diabet. Med., 14:27-S85 (1997).

Amundadottir et al., A common variant associated with prostate cancer in European and African populations, Nat. Genet., 38:652-8 (2006).

Asleh et al., In vivo and in vitro studies establishing haptoglobin as a major susceptibility gene for diabetic vascular disease, Vascular Health Risk Management, 1:19-28 (2005).

Authier at al., Endosomal proteolysis of internalized insulin at the C-terminal region of the B chain by cathepsin D. J. Biol. Chem., 277(11):9437-46 (2002).

Bennett, Efficiency of antisense oligonucleotide drug discovery, Antisense Nucleic Acid Drug Dev., 12:215-24 (2002).

Bier at al., DNA microarrays, Adv. Biochem. Eng. Biotechnol., 109:433-53 (2008).

(56) References Cited

OTHER PUBLICATIONS

Bosher et al., RNA Interference: genetic wand and genetic watchdog, Nat. Cell Biol., 2:E31-6 (2000).
Brummelkamp et al., A system for stable expression of short interfering RNAs in mammalian cells, Science, 296:550-3 (2002).
Carter et al., Methods and strategies for analyzing copy number variation using DNA microarrays, Nat. Genet., 39:516-21 (2007).
Cauchi et al., TCF7L2 is reproducibly associated with type 2 diabetes in various ethnic groups: a global meta-analysis, J. Mol. Med. (Berl), 85(7):777-82 (2007).
Chen et al., Fluorescence polarization in homogeneous nucleic acid analysis, Genome Res., 9:492-8 (1999).
Chen, Clinical development of antisense oligonucleotides as anticancer therapeutics, Methods Mol. Med., 75:621-36 (2003).
Chi et al., Genomewide view of gene silencing by small interfering RNAs, Proc. Natl. Acad. Sci. USA, 100:6343-6 (2003).
Chiarelli et al., Screening for vascular complications in children and adolescents with type 1 diabetes mellitus, Norm. Res., 57 Suppl 1:113-6 (2002).
Church et al., Genomic sequencing, Proc. Natl. Acad. Sci. USA, 81:1991-5 (1984).
Cotton et al., Reactivity of cytosine and thymine in single-base-pair mismatches with hydroxylamine and osmium tetroxide and its application to the study of mutations, Proc. Natl. Acad. Sci. USA, 85:4397-401 (1988).
Daly et al., High-resolution haplotype structure in the human genome, Nat. Genet., 29:229-32 (2001).
Dawson et al., A first-generation linkage disequilibrium map of human chromosome 22, Nature, 418:544-8 (2002).
Dempster et al., Manual likelihood from incomplete data via the EM algorithm, J. Royal Stat. Soc. B, 39:1-38 (1977).
Devlin et al., A comparison of linkage disequilibrium measures for fine-scale mapping, Genomics, 29(2):311-22 (1995).
Devlin et al., Genomic control for association studies, Biometrics, 55(4):997-1004 (1999).
Devlin et al., Genomic Control to the extreme, Nat. Genet., 36:1129-30 (2004).
Dias et al., Antisense oligonucleotides: basic concepts and mechanisms, Mol. Cancer Ther., 1:347-55 (2002).
Donnelly et al., ABC of arterial and venous disease: vascular complications of diabetes, BMJ, 320(7241):1062-6 (2000).
Easton et al., Genome-wide association study identifies novel breast cancer susceptibility loci, Nature, 447(7148)1 087-93 (2007).
Estivill et al., Copy number variants and common disorders: filling the gaps and exploring complexity in genome-wide association studies, PLoS Genet., 3:1787-99 (2007).
Falk et al., Haplotype relative risks: an easy reliable way to construct a proper control sample for risk calculations, Ann. Hum. Genet., 51:227-33 (1987).
Fan et al., Illumina universal bead arrays, Methods Enzymol., 410:57-73 (2006).
Fire et al., Potent and specific genetic interference by double-stranded RNA in *Caenorhabditis elegans*, Nature, 391:806-11 (1998).
Flavell et al., Analysis of the beta-delta-globin gene loci in normal and Hb Lepore DNA: direct determination of gene linkage and intergene distance, Cell, 15:25-41 (1978).
Florez et al., TCF7L2 polymorphisms and progression to diabetes in the Diabetes Prevention Program, N. Engl. J. Med., 355(3):241-50 (2006).
Frayling et al., Genome-wide association studies provide new insights into type 2 diabetes aetiology, Nat. Rev. Genet., 8:657-62 (2007).
Freimer et al., Human genetics: variants in common diseases, Nature, 445(7130):828-30 (2007).
Fuchs et al., Targeting recombinant antibodies to the surface of *Escherichia Coli*: fusion to a peptidoglycan associated lipoprotein, Bio/Technology, 9:1369-72 (1991).
Gabriel et al., The structure of haplotype blocks in the human genome, Science, 296:2225-9 (2002).
Galfre et al., Antibodies to major histocompatibility antigens produced by hybrid cell lines, Nature, 266:550-2 (1977).
Geever et al., Direct Identification of sickle cell anemia by blot hybridization, Proc. Natl. Acad. Sci. USA, 78:5081-5 (1981).
Gloyn et al., Large-scale association studies of variants in genes encoding the pancreatic beta-cell KATP channel subunits Kir6.2 (KCNJ11) and SUR1 (ABCC8) confirm that the KCNJ11 E23K variant is associated with type 2 diabetes. Diabetes, 52(2):568-72 (2003).
Gloyn, The search for type 2 diabetes genes, Ageing Res. Rev., 2(2):111-27 (2003).
Goldberg et al., Biallelic expression of HRAS and MUCDHL in human and mouse, Hum. Genet., 112(4):334-42 (2003).
Grant et al., Variant of transcription factor 7-like 2 (TCF7L2) gene confers risk of type 2 diabetes, Nat. Genet., 38:320-3 (2006).
Gretarsdottir et al., Risk variants for atrial fibrillation on chromosome 4q25 associate with ischemic stroke, Ann. Neurol., 64:402-9 2008.
Gretarsdottir et al., The gene encoding phosphodiesterase 4D confers risk of ischemic stroke, Nat. Genet., 35:131-8 (2003).
Griffiths et al., Human anti-self antibodies with high specificity from phage display libraries, EMBO J., 12:725-34 (1993).
Gudbjartsson et al., ASIP and TYR pigmentation variants associate with cutaneous melanoma and basal cell carcinoma, Nat. Genet., 40:886-91 (2008).
Gudmundsson et al., Common sequence variants on 2p15 and Xp11.22 confer susceptibility to prostate cancer, Nat. Genet., 40:281-3 (2008).
Gudmundsson et al., Genome-wide association study identifies a second prostate cancer susceptibility variant at 8.24, Nat. Genet., 39:631-7 (2007).
Gudmundsson et al., Two variants on chromosome 17 confer prostate cancer risk, and the one in TCF2 protects against type 2 diabetes, Nat. Genet., 39:977-83 (2007).
Haiman et al., Multiple regions within 8q24 independently affect risk for prostate cancer, Nat. Genet., 39:638-44 (2007).
Hay et al., Bacteriophage cloning and *Escherichia coli* expression of a human IgM Fab, Hum. Antibodies Hybridomas, 3:81-5 1992.
Helgadottir et al., A common variant on chromosome 9p21 affects the risk of myocardial infarction, Science, 316:1491-3 (2007).
Hill et al., Linkage disequilibrium in finite populations, Theor. Appl. Genet., 22:226-31 (1968).
Hindorff et al., Potential etiologic and functional implications of genome-wide association loci for human diseases and traits, Proc. Natl. Acad. Sci. USA, 106 (23):9362-7 (2009).
Hoheisel, Microarray technology: beyond transcript profiling and genotype analysis, Nat. Rev. Genet., 7:200-10 (2006).
Horenstein et al., Genetics of diabetes, Diabetes, 5(1):25-33 (2004).
Hunter, Genetics: a touch of elegance with RNAi, Curr. Biol., 9:R440-2 (1999).
Huse et al., Generation of a large combinatorial library of the immunoglobulin repertoire in phage lambda, Science, 246:1275-81 (1989).
International Search Report for corresponding international application No. PCT/IS2010/050007, mailing date Oct. 5, 2010.
Jeffreys et al., Intensely punctate meiotic recombination in the class II region of the major histocompatibility complex, Nat. Genet., 29:217-22 (2001).
Karlin et al., Applications and statistics for multiple high-scoring segments in molecular sequences, Proc. Natl. Acad. Sci. USA, 90:5873-7 (1993).
Kent, Blat—The BLAST-like alignment tool, Genome Res., 656-64 (2002).
Kim et al., Strategies for silencing human disease using RNA interference, Nat. Rev. Genet., 8:173-84 (2007).
Kim et al., Synthetic dsRNA Dicer substrates enhance RNAi potency and efficacy, Nat. Biotechnol., 23:222-6 (2005).
King et al., Global burden of diabetes, 1995-2025: prevalence, numerical estimates, and projections, Diabetes Care, 21(9):1414-31 (1998).
Kohler et al., Continuous cultures of fused cells secreting antibody of predefined specificity, Nature, 256:495-7 (1975).
Kong et al., Detection of sharing by descent, long-range phasing and haplotype imputation, Nat. Genet., 40(9):1068-75 (2008).

(56) References Cited

OTHER PUBLICATIONS

Kong et al., Parental origin of sequence variants associated with complex diseases, Nature, 462(7275):868-74 (2009).
Kozbor et al., The production of monoclonal antibodies from human lymphocytes, Immunol. Today, 4:72-9 (1983).
Kraus et al., Detection and isolation of novel protein-tyrosine kinase genes employing reduced stringency hybridization, Methods Enzymol., 200:546-56 (1991).
Krolewski et al, Epidemiologic approach to the etiology of type I diabetes mellitus and its complications, N. Eng. J. Med., 317(22):1390-8 (1987).
Kurreck, Antisense technologies. Improvement through novel chemical modifications, Eur. J. Biochem., 270:1628-44 (2003).
Kutyavin et al., A novel endonuclease IV post-PCR genotyping system, Nucleic Acids Res., 34:e128 (2006).
Lavery et al., Antisense and RNAi: powerful tools in drug target discovery and validation, Curr. Opin. Drug Discov. Devel., 6:561-9 (2003).
Lerner, How to make a hybridoma, Yale J. Biol. Med., 54:387-402 (1981).
Lewontin et al., The Interaction of Selection and Linkage. I. General Considerations: Heterotic Models, Genetics, 49(1):49-67 (1964).
Li et al., Hepatocellular carcinoma-associated gene 2 interacts with MAD2L2, Mol. Cell Biochem., 304(1-2):297-304 (2007).
Luedi et al., Computational and experimental identification of novel human imprinted genes, Genome Res. 17(12):1723-30 (2007).
Luedi et al., Genome-wide prediction of imprinted murine genes, Genome Res., 15(6):875-84 (2005).
Maniatis et al., The first linkage disequilibrium (LD) maps: delineation of hot and cold blocks by diplotype analysis, Proc. Natl. Acad. Sci USA, 99:2228-33 (2002).
Mantel et al., Statistical aspects of the analysis of data from retrospective studies of disease, J. Natl. Cancer Inst., 22:719-48 (1959).
Marques et al., A structural basis for discriminating between self and nonself double-stranded RNAs in mammalian cells, Nat. Biotechnol., 24:559-65 (2006).
Marshall et al., Prevention and early detection of vascular complications of diabetes, BMJ, 333(7566):475-80 (2006).
May et al., Crossover clustering and rapid decay of linkage disequilibrium in the Xp/Yp pseudoautosomal gene SHOX, Nat. Genet., 31:272-5 (2002).
McManus et al., Gene silencing in mammals by small interfering RNAs, Nat. Rev. Genet., 3:737-47 (2002).
Mockler et al., Applications of DNA tiling arrays for whole-genome analysis, Genomics, 85:1-15 (2005).
Myers et al., A fine-scale map of recombination rates and hotspots across the human genome, Science, 310(5746):321-4 (2005).
Myers et al., Detection of single base substitutions by ribonuclease cleavage at mismatches in RNA:DNA duplexes, Science, 230:1242-6 (1985).
Myers et al., The distribution and causes of meiotic recombination in the human genome, Biochem. Soc. Trans., 34:526-30 (2006).
Nicolae, Measuring the relative information in allele-sharing linkage studies, Biometrics, 60:368-75 (2004).
Nielsen et al., Peptide nucleic acid (PNA). A DNA mimic with a peptide backbone, Bioconjug. Chem., 5:3-7 (1994).
Nielsen et al., Sequence-selective recognition of DNA by strand displacement with a thymine-substituted polyamide, Science, 254:1497-500 (1991).
Nyren et al., Solid phase DNA minisequencing by an enzymatic luminometric inorganic pyrophosphate detection assay, Anal. Biochem., 208:171-5 (1993).
Orita et al., Detection of polymorphisms of human DNA by gel electrophoresis as single-strand conformation polymorphisms, Proc. Natl. Acad. Sci. USA, 86:2766-70 (1989).
Patil et al., Blocks of limited haplotype diversity revealed by high resolution scanning of human chromosome 21, Science, 294:1719-23 (2001).
Pearson et al., Variation in TCF7L2 influences therapeutic response to sulfonylureas: a GoDARTs study, Diabetes, 56(8):2178-82 (2007).

Phillips et al., Chromosome-wide distribution of haplotype blocks and the role of recombination hot spots, Nat. Genet., 33:382-7 (2003).
Plasterk et al., The silence of the genes, Curr. Opin. Genet. Dev., 10:562-7 (2000).
Rafnar et al., Sequence variants at the TERT-CLPTM1L locus associate with many cancer types, Nat. Genet., 41:221-7 (2009).
Ragoussis et al., Affymetrix GeneChip system: moving from research to the clinic, Expert Rev. Mol. Diagn., 6:145-52 (2006).
Redon et al., Global variation in copy number in the human genome, Nature, 444:444-54 (2006).
Reich et al., Linkage disequilibrium in the human genome, Nature, 411:199-204 (2001).
Reynisdottir et al., Localization of a susceptibility gene for type 2 diabetes to chromosome 5q34-q35.2, Am. J. Hum. Genet., 73(2):323-35 (2003).
Reynolds et al., Rational siRNA design for RNA interference, Nat. Biotechnol., 22:326-30 (2004).
Risch et al., The future of genetic studies of complex human diseases, Science, 273:1516-7 (1996).
Risch et al., The relative power of family-based and case-control designs for linkage disequilibrium studies of complex human diseases I. DNA pooling, Genome Res., 8:1273-88 (1998).
Ronaghi et al., Analyses of secondary structures in DNA by pyrosequencing, Anal. Biochem., 267:65-71 (1999).
Ronaghi et al., PCR-introduced loop structure as primer in DNA sequencing, Biotechniques, 25:876-8, 880-2, 884 (1998).
Sanger et al., DNA sequencing with chain-terminating inhibitors, Proc. Natl. Acad. Sci. USA, 74:5463-7 (1977).
Saxena et al., Genome-wide association analysis identifies loci for type 2 diabetes and triglyceride levels, Science, 316(5829):1331-6 (2007).
Scott et al., A genome-wide association study of type 2 diabetes in Finns detects multiple susce tibilit variants, Science 316(5829):1341-5 (2007).
Sheffield et al., Attachment of a 40-base-pair G + C-rich sequence (GC-clamp) to genomic DNA fragments by the polymerase chain reaction results in improved detection of single-base changes, Proc. Natl. Acad. Sci. USA, 86:232-6 (1989).
Shi, Mammalian RNAi for the masses, Trends Genet., 19:9-12 (2003).
Shuey et al., RNAi: gene-silencing in therapeutic intervention, Drug Discov. Today, 7:1040-6 (2002).
Siolas et al., Synthetic shRNAs as potent RNAi triggers, Nat. Biotechnol., 23:227-31 (2005).
Smith et al.. A high density admixture map for disease gene discovery in african americans, Am. J. Hum. Genet., 74;1001-13 (2004).
Stacey et al., Common variants on 1p36 and 1q42 are associated with cutaneous basal cell carcinoma but not with melanoma or pigmentation traits, Nat. Genet., 40:1313-8 (2008).
Stacey et al., Common variants on Chromosomes 2q35 and 16q12 confer susceptibility to estrogen receptor-positive breast cancer, Nat. Genet., 39:865-9 (2007).
Steinthorsdottir et al., A variant in CDKAL1 influences insulin response and risk of type 2 diabetes, Nat. Genet., 39:770-5 (2007).
Stephens et al., Antisense oligonucleotide therapy in cancer, Curr. Opin. Mol. Ther., 5:118-22 (2003).
Strausberg et al., Emerging DNA sequencing technologies for human genomic medicine, Drug Discov. Today, 13:569-77 (2008).
Stumpf et al., Demography, recombination hotspot intensity, and the block structure of linkage disequilibrium, Curr. Biol., 13:1-8 (2003).
Styrkarsdottir et al., Multiple genetic loci for bone mineral density and fractures, N. Engl. J. Med., 358:2355-65 (2008).
Sulem et al., Genome-wide association study identifies sequence variants on 6q21 associated with age at menarche, Nat. Genet., 41:734-8 (2009).
Terwilliger et al., A haplotype-based 'haplotype relative risk' approach to detecting allelic associations, Hum. Hered., 42:337-46 (1992).
Thorgeirsson et al., A variant associated with nicotine dependence, lung cancer and peripheral arterial disease, Nature, 452:638-42 (2008).

(56) References Cited

OTHER PUBLICATIONS

Torelli et al., Advance and Adam: two algorithms for the analysis of global similarity between homologous informational sequnces. CABIOS, 10:3-5 (1984).

Vickers et al., Efficient reduction of target RNAs by small interfering RNA and RNase H-dependent antisense agents. A comparative analysis, J. Biol. Chem., 278:7108-18 (2003).

Vilbergsson et al., Prevalence and incidence of NIDDM in Iceland: evidence for stable incidence among males and females 1967-1991—The Reykjavik Study, Diabet. Med., 14 6 :491-8 (1997).

Wagman et al., Discovery and development of GSK3 inhibitors for the treatment of type 2 diabetes, Curr. Pharm. Des., 10(10):1105-37 (2004).

Wall et al., Haplotype blocks and linkage disequilibrium in the human genome, Nat. Rev. Genet., 4:587-97 (2003).

Wang et al., Antisense anticancer oligonucleotide therapeutics, Curr. Cancer Drug Targets, 1:177-96 (2001).

Wang et al., Distribution of recombination crossovers and the origin of haplotype blocks: the interplay of population history, recombination, and mutation, Am. J. Hum. Genet., 71:1227-34 (2002).

Xia et al., siRNA-mediated gene silencing in vitro and in vivo, Nat. Biotechnol., 20:1006-10 (2002).

Yeager et al., Genome-wide association study of prostate cancer identifies a second risk locus at 8q24, Nat. Genet., 39:645-9 (2007).

Zeggini et al., Meta-analysis of genome-wide association data arid large-scale replication identifies additional susceptibility loci for type 2 diabetes, Nat. Genet., 40 (5):638-45 (2008).

Zeggini et al., Replication of genome-wide association signals in UK samples reveals risk loci for type 2 diabetes, Science, 316(5829):1336-41 (2007).

Zhang et al., A dynamic programming algorithm for haplotype block partitioning, Proc. Natl. Acad. Sci. USA, 99:7335-9 (2002).

Nonfinal office action from U.S. Appl. No. 12/456,381, dated Jul. 13, 2011.

Nonfinal office action from U.S. Appl. No. 12/442,233, dated Aug. 25, 2011.

Nonfinal office action from U.S. Appl. No. 12/442,233, dated Mar. 26, 2012.

Langdahl et al., Osteoorotic fractures are associated with an 86-base pair repeat polymorphism in the interleukin 1 receptor antagonist gene but not with polymorphisms in the interleukin 1β gene, J. Bone Mineral Res., 115:402-14 (2000).

Namkung et al., Whole genome association studies of alcoholism with loci linked to schizophrenia susceptibility, BMC Genetics, 6:S9 (2005).

GENETIC MARKERS ASSOCIATED WITH RISK OF DIABETES MELLITUS

CROSS-REFERENCE TO RELATED APPLICATIONS

This application is a 35 U.S.C. §371 National filing of International Application No. PCT/IS2010/050007, filed Jul. 9, 2010, incorporated herein by reference, which claims priority benefit of Iceland patent application No. 8836, filed Jul. 10, 2009.

BACKGROUND OF THE INVENTION

Genetic risk is conferred by subtle differences in the sequence of the genome among individuals in a population. The human genome differs between individuals most frequently due to single nucleotide polymorphisms (SNPs), although other variations are also important. SNPs are located on average every 500 base pairs in the human genome. Accordingly, a typical human gene containing 250,000 base pairs may contain approximately 500 different SNPs. Only a minor number of SNPs are located in exons and alter the amino acid sequence of the protein encoded by the gene. Most SNPs may have no known effect on gene function, while others are known to alter transcription, splicing, translation, or stability of the mRNA encoded by the gene. Additional genetic polymorphisms in the human genome are caused by insertions, deletions, translocations, or inversions of either short or long stretches of DNA.

Parent-of-origin effects (POE) are genetic effects that are transmitted from parents to offspring in such a manner that the expression of the phenotype in the offspring depends on whether the transmission originated from the mother or the father. The effect of a sequence variant in the nuclear genome on the phenotype may depend on its parental origin. In one scenario, the effect is due to imprinting, in which an allele is silenced via an epigenetic mechanism such as methylation when inherited from one parent and expressed when inherited from the other parent. In general, however, there are three parent-of-origin effects, i.e. those that arise from epigenetic regulation of gene expression (e.g., imprinting), those that arise from effects of intrauterine environment on the development of the fetus and those that arise from genetic variation in the maternally inherited mitochondrial genome.

Diabetes mellitus, often called diabetes, is a metabolic disease wherein carbohydrate utilization is reduced and lipid and protein utilization is enhanced, and is caused by an absolute or relative deficiency of insulin. In the more severe cases, diabetes is characterized by chronic hyperglycemia, glycosuria, water and electrolyte loss, ketoacidosis and coma. Long term complications can include development of both microvascular complications such as neuropathy, retinopathy and nephropathy and macrovascular complications such as myocardial infarction (MI), stroke and peripheral arterial disease (PAD), caused by generalized degenerative changes in large and small blood vessels. The most common form of diabetes is type 2 diabetes (T2D), (also called non-insulin-dependent diabetes) which is characterized by hyperglycemia due to impaired insulin secretion and insulin resistance in target tissues and increased glucose output by the liver. Both genetic and environmental factors contribute to T2D. For example, obesity plays a major role in the development of T2D. Type 1 diabetes is characterized by loss of insulin-producing beta cells in the islets of Langerhans, leading to insulin deficiency, and represents a majority of diabetes cases affecting children.

The prevalence of T2D worldwide is currently 6% but is projected to rise over the next decade (Amos, A. F., McCarty, D. J., Zimmet, P., *Diabet Med* 14 Suppl 5, S1 (1997)). This increase in prevalence of T2D is attributed to increasing age of the population and rise in obesity. The health implications of T2D are enormous. In 1995, there were 135 million adults with the disease worldwide. It is estimated that close to 300 million will have T2D in the year 2025 (King, H., et al., *Diabetes Care,* 21(9): 1414-1431 (1998)). The prevalence of T2D in the adult population in Iceland is 2.5% (Vilbergsson, S., et al., *Diabet. Med.,* 14(6): 491-498 (1997)), which means that approximately 5,000 people over the age of 34 in Iceland have T2D.

Many T2D patients suffer serious complications of chronic hyperglycemia including microvascular complications (nephropathy, neuropathy, retinopathy) and accelerated development of cardiovascular disease (including cerebrovascular disease (stroke), myocardial infarction, and peripheral arterial disease) through macrovascular complications.

In fact, the enormous public health burden of diabetes is largely due to the development of vascular complications of the disease. Cardiovascular disease (CVD) is a major complication and the leading cause of premature death among people with diabetes and accounts for over 75% of all deaths among diabetics. Adults with diabetes are two to four times more likely to have heart disease or suffer a stroke than people without diabetes. Approximately 35% of type 1 diabetes patients die from a cardiovascular disease before age 55, illustrating the devastating consequence of the disease through its cardiovascular complications (Krolewski, A. S. et al. *N Engl J Med* 317:1390-8 (1987)). The overall prevalence of cardiovascular disease is over 55% in adults with diabetes as compared with 2%-4% of the general population (Asley, R. Levy, A. P. *Vasc Health Risk Man* 1:19-28 (2005)).

Diabetic retinopathy is the cause of blindness in about 5% of blind people worldwide, and almost everyone with diabetes has some degree of retinopathy after 20 years with the disease (Marshall, S. M. Flyvbjerg, A. *British Med J* 333:475-80 (2006)). The prevalence of retinopathy is highest in young-onset patients, and steadily increase with duration of diabetes (Chiarelli, F., et al. *Horm Res* 57(suppl 1):113-6 (2002)).

Nephropathy is also common in diabetic patients, which confers increased risk of premature death due to end-stage renal failure and cardiovascular disease. About half of diabetic patients develop microalbuminuria, which is a marker for early nephropathy, at some point, and about one third will progress to proteinuria. Once present, proteinuria will inevitably lead to end stage renal disease; between 20% and 50% of patients who start renal replacement therapy have diabetes (Marshall, S. M. Flyvbjerg, A. *British Med J* 333:475-80 (2006)). Patients with diabetes have between 30% and 50% lifetime risk of developing chronic peripheral neuropathy, which can lead to severe symptoms such as foot ulcerations and amputation of lower limbs.

Many of the complications of diabetes have a prolonged subclinical asymptomatic phase. Thus, screening for presymptomatic complications, such as retinopathy and microalbuminuria is extremely important for effective disease management. For example, the micro- and macrovascular complications of diabetes are almost unknown in younger children and rare in adolescents and young adults, but can be detected as soon as 2-5 years after diagnosis during childhood and adolescence (Clarke B. F., in *Diabetes Mellitus in Children and Adolescents*, Kelnar, C. (ed); London, Chapman & Hall, pp 539-51 (1994)).

As genetic polymorphisms conferring risk of common diseases, such as Type 1 and Type 2 diabetes mellitus, are uncovered, genetic testing for such risk factors is becoming important for clinical medicine. Established examples include apolipoprotein E testing to identify genetic carriers of the apoE4 polymorphism in dementia patients for the differential diagnosis of Alzheimer's T2D, and of Factor V Leiden testing for predisposition to deep venous thrombosis. More importantly, in the treatment of cancer, diagnosis of genetic variants in tumor cells is used for the selection of the most appropriate treatment regime for the individual patient. In breast cancer, genetic variation in estrogen receptor expression or heregulin type 2 (Her2) receptor tyrosine kinase expression determine if anti-estrogenic drugs (tamoxifen) or anti-Her2 antibody (Herceptin) will be incorporated into the treatment plan. In chronic myeloid leukemia (CML) diagnosis of the Philadelphia chromosome genetic translocation fusing the genes encoding the Bcr and Abl receptor tyrosine kinases indicates that Gleevec (STI571), a specific inhibitor of the Bcr-Abl kinase should be used for treatment of the cancer. For CML patients with such a genetic alteration, inhibition of the Bcr-Abl kinase leads to rapid elimination of the tumor cells and remission from leukemia.

Until recently, two approaches were mainly used to search for genes associated with T2D. Single nucleotide polymorphisms (SNPs) within candidate genes have been tested for association and two variants conferring a modest risk of T2D were identified by this method; a protective Pro12Ala polymorphism in the peroxisome proliferator activated receptor gamma gene (PPARG2) (Altshuler, D. et al., *Nat Genet.* 26, 76 (2000)) and a polymorphism in the potassium inwardly-rectifying channel, subfamily J, member 11 gene (KCNJ11) (Gloyn A. L. et al., *Diabetes* 52, 568 (2003)). Genome-wide linkage scans in families with the common form of T2D have yielded several loci but the responsible genes within these loci have mostly yet to be uncovered. The rare Mendelian forms of T2D, namely maturity-onset diabetes of the young (MODY), have yielded six genes by positional cloning (Gloyn, A. L., *Ageing Res Rev* 2, 111 (2003)).

Genome-wide linkage scan for T2D in the Icelandic population showed suggestive evidence of linkage to chromosome 10q (Reynisdottir, I. et al., *Am J Hum Genet.* 73, 323 (2003)). Fine mapping of this locus revealed the transcription factor 7-like 2 gene (TCF7L2; formerly TCF4) as being associated with T2D (P=2.1×10(−9)) (Grant, S. F. et al., *Nat Genet.* 38, 320 (2006)). Compared with non-carriers, heterozygous and homozygous carriers of the at-risk alleles (38% and 7% of the population, respectively) have relative risks of 1.45 and 2.41. This corresponds to a population attributable risk of 21%. Association of the TCF7L2 variant has now been replicated in a large number of independent studies with similar relative risk found in the different populations studied. The TCF7L2 gene product is a high mobility group box-containing transcription factor previously implicated in blood glucose homeostasis. It is thought to act through regulation of proglucagon gene expression in enteroendocrine cells via the Wnt signaling pathway.

Recently, genome wide association studies using a large number (300,000-1,000,000) of SNPs have been applied to T2D (Sladek, R et al. Nature. 2007; 445:828-30; Steinthorsdottir V et al. Nat. Gen. 2007; 39:770-5; Saxena, R et al. Science 2007; 316:1331-6; Zeggini, E et al. Science 2007; 316:1336-41; Scott, L J et al. Science 2007; 316:1341-5; Zeggini, E et al. Nat. Gen. 40:638-45 (2008). In addition to confirming the three previously identified variants (PPARG, KCNJ11 and TCF7L2) these studies have thus far identified 11 additional genetic variants conferring risk of T2D. All the variants have a modest risk with TCF7L2 conferring the highest risk. Most, if not all, genome wide studies published to date treat the paternal and maternal alleles as interchangeable. This is likely due to the fact that unless the parents of a proband have been genotyped, the information required to determine the parental origin of alleles is unavailable.

Despite the advances in unraveling the genetics of T2D, the pathophysiology of the T2D remains elusive. However, with the current genetic information we are in a better position to test the effect of different treatment options in relation to the genetic background. It has already been shown that the TCF7L2 at-risk genotype affects the treatment outcome both from lifestyle changes and medication (Florez J C et al. *N Engl J Med* 2006; 355:241-50; Pearson E R et al. *Diabetes* 2007; 2178-82).

While our understanding of the genetic bases of developing T2D has increased, the genetics of the disease are still not fully explained. There is therefore an unmet medical need to define additional genetic risk factors affecting the development of T2D. Such information could then be used for diagnostic applications, including applications for identifying those at particularly high risk of developing T2D, development of risk management methods, and for risk stratification where individuals at high risk would be targeted for stringent treatment of other risk factors such as glycemia, high cholesterol and hypertension.

SUMMARY OF THE INVENTION

The present invention relates to materials and methods for predicting disease risk, by determining the parental origin of particular alleles at polymorphic sites. Certain markers have been found to be predictive of risk of certain diseases, including type 2 diabetes, breast cancer and basal cell carcinoma. Such markers are useful in various diagnostic applications, as described further herein.

In a general sense, the invention provides methods of determining susceptibility to a medical condition for a human subject. To determine such susceptibility, sequence information about particular polymorphic markers is obtained. Preferably, the information includes parental origin of particular alleles, and susceptibility to the condition determined based on such information.

In a first aspect the invention provides a method of determining a susceptibility to type 2 diabetes in a human individual, the method comprising (i) obtaining nucleic acid sequence data about a human individual identifying at least one allele of at least one polymorphic marker, and (ii) determining a susceptibility to type 2 diabetes from the sequence data, wherein the at least one polymorphic marker is selected from the group consisting of rs2334499, and markers in linkage disequilibrium therewith.

Another aspect provides a method of determining a susceptibility to type 2 diabetes in a human individual, the method comprising (i) analyzing nucleic acid sequence data from a human individual for at least one polymorphic marker selected from the group consisting of rs2334499, and markers in linkage disequilibrium therewith, and (ii) determining a susceptibility to type 2 diabetes from the nucleic acid sequence data.

The method may include a further step of determining the parental origin of the at least one allele of the at least one polymorphic marker, wherein different parental origins of the at least one allele are associated with different susceptibilities to type 2 diabetes in humans, and determining a susceptibility to type 2 diabetes based on the parental origin of said at least one allele.

In certain embodiments, the at least one polymorphic marker is selected from the group consisting of rs2334499, rs1038727, rs7131362, rs748541, rs4752779, rs4752780, rs4752781, rs4417225, rs10769560, rs17245346, rs11607954, rs10839220, and rs11600502.

In one embodiment, determination of a paternal origin of the T allele of rs2334499, or a marker allele in linkage disequilibrium therewith, is indicative of increased susceptibility of type 2 diabetes in the individual. Further, determination of a maternal origin of the T allele of rs2334499, or a marker allele in linkage disequilibrium therewith, is indicative of a decreased susceptibility of type 2 diabetes in the individual.

Some embodiments include a further step comprising determining whether at least one additional at-risk variant of type 2 diabetes is present in the individual. The at least one at-risk variant is in some embodiments selected from the group consisting of allele T of rs7903146, allele C of rs1801282, allele G of rs7756992, allele T of rs10811661, allele C of rs1111875, allele T of rs4402960, allele T of rs5219, allele C of rs9300039, allele A of rs8050136, allele C of rs13266634, allele T of rs7836388, allele A of rs11775310, allele C of rs1515018, allele C of rs1470579, and allele C of rs7754840.

Certain embodiments further include a step of determining at least one biomarker in the human individual.

Another aspect of the invention relates to a method of determining a susceptibility to type 2 diabetes in a human individual, the method comprising (i) obtaining sequence data about a human individual identifying at least one allele of at least one polymorphic marker, wherein different parental origins of the at least one allele are associated with different susceptibilities to type 2 diabetes in humans; (ii) determining the parental origin of said at least one allele; and (iii) determining a susceptibility to type 2 diabetes for the individual based on the parental origin of said at least one allele; wherein the at least one polymorphic marker is selected from the group consisting of rs2237892, rs231362, rs4731702 and rs2334499, and markers in linkage disequilibrium therewith.

In certain embodiments, determination of a maternal origin of the C allele of rs2237892, a maternal origin of the C allele of rs231362, a maternal origin of the C allele of rs4731702, or a paternal origin of the T allele of rs2334499, or a marker allele in linkage disequilibrium therewith, is indicative of increased susceptibility of type 2 diabetes in the individual.

Also provided is a method of determining a susceptibility to breast cancer in a human individual, the method comprising (i) obtaining sequence data about a human individual identifying at least one allele of at least one polymorphic marker, wherein different parental origins of the at least one allele are associated with different susceptibilities to breast cancer in humans; (ii) determining the parental origin of said at least one allele; and (iii) determining a susceptibility to breast cancer for the individual based on the parental origin of said at least one allele; wherein the at least one polymorphic marker is selected from the group consisting of rs3817198, and markers in linkage disequilibrium therewith. In one embodiment, determination of a paternal origin of the C allele of rs3817198, or a marker allele in linkage disequilibrium therewith, is indicative of increased susceptibility to breast cancer in the individual.

The invention also provides a method of determining a susceptibility to basal cell carcinoma in a human individual, the method comprising (i) obtaining sequence data about a human individual identifying at least one allele of at least one polymorphic marker, wherein different parental origins of the at least one allele are associated with different susceptibilities to basal cell carcinoma in humans; (ii) determining the parental origin of said at least one allele; and (iii) determining a susceptibility to basal cell carcinoma for the individual based on the parental origin of said at least one allele; wherein the at least one polymorphic marker is selected from the group consisting of rs157935, and markers in linkage disequilibrium therewith. In one embodiment, determination of a paternal origin of the T allele of rs157935 is indicative of increased susceptibility to basal cell carcinoma in the individual.

Another aspect of the invention relates to a method of identification of a marker for use in assessing susceptibility to type 2 diabetes, the method comprising (i) identifying at least one polymorphic marker in linkage disequilibrium with at least one of the markers rs2237892, rs231362, rs4731702 and rs2334499; (ii) determining the genotype status of a sample of individuals diagnosed with, or having a susceptibility to, type 2 diabetes; and (iii) determining the genotype status of a sample of control individuals; wherein a significant difference in frequency of at least one allele in at least one polymorphism in individuals diagnosed with, or having a susceptibility to, type 2 diabetes, as compared with the frequency of the at least one allele in the control sample is indicative of the at least one polymorphism being useful for assessing susceptibility to type 2 diabetes.

Determination of an increase in frequency of the at least one allele in the at least one polymorphism in individuals diagnosed with, or having a susceptibility to, type 2 diabetes, as compared with the frequency of the at least one allele in the control sample is in certain embodiments, indicative of the at least one polymorphism being useful for assessing increased susceptibility to type 2 diabetes; and a decrease in frequency of the at least one allele in the at least one polymorphism in individuals diagnosed with, or having a susceptibility to, type 2 diabetes, as compared with the frequency of the at least one allele in the control sample is indicative of the at least one polymorphism being useful for assessing decreased susceptibility to, or protection against, type 2 diabetes.

Also provided is a method of predicting prognosis of a human individual experiencing symptoms associated with, or an individual diagnosed with, type 2 diabetes, the method comprising (i) obtaining sequence information about the human individual identifying at least one allele of at least one polymorphic marker selected from the group consisting of rs2237892, rs231362, rs4731702 and rs2334499, and markers in linkage disequilibrium therewith, wherein different alleles of the at least one polymorphic marker are associated with different susceptibilities to type 2 diabetes in humans, and predicting prognosis of type 2 diabetes of the human individual from the sequence data.

Further provided is a method of assessing an individual for probability of response to a therapeutic agent for preventing, treating and/or ameliorating symptoms associated with type 2 diabetes, comprising (i) obtaining sequence information about the human individual identifying at least one allele of at least one polymorphic marker selected from the group consisting of rs2237892, rs231362, rs4731702 and rs2334499, and markers in linkage disequilibrium therewith, wherein the at least one allele is associated with a probability of a positive response to the therapeutic agent in humans, and determining the probability of a positive response to the therapeutic agent from the sequence data. In certain embodiments, the therapeutic agent is selected from the group consisting of the agents set forth in Agent Table 1 and Agent Table 2.

The invention also provides kits. In one such aspect, a kit for assessing susceptibility to type 2 diabetes in a human individual is provided, the kit comprising (i) reagents for selectively detecting at least one allele of at least one polymorphic marker in the genome of the individual, wherein the polymorphic marker is selected from the group consisting of rs2237892, rs231362, rs4731702 and rs2334499, and markers in linkage disequilibrium therewith, and (ii) a collection of data comprising correlation data between the polymorphic markers assessed by the kit and susceptibility to type 2 diabetes.

Yet another aspect of the invention relates to the use of an oligonucleotide probe in the manufacture of a diagnostic reagent for diagnosing and/or assessing susceptibility to type 2 diabetes in a human individual, wherein the probe is capable of hybridizing to a segment of a nucleic acid whose sequence is given by any one of SEQ ID NO:1-7, wherein the segment is 15-500 nucleotides in length. In a preferred embodiment, the segment of the nucleic acid to which the probe hybridizes comprises a polymorphic site.

Computer-implemented aspects are also provided. One such aspect relates to a computer-readable medium having computer executable instructions for determining susceptibility to type 2 diabetes in a human individual, the computer readable medium comprising (i) data indicative of at least one polymorphic marker; and (ii) a routine stored on the computer readable medium and adapted to be executed by a processor to determine risk of developing type 2 diabetes in an individual for the at least one polymorphic marker; wherein the at least one polymorphic marker is selected from the group consisting of rs2237892, rs231362, rs4731702 and rs2334499, and markers in linkage disequilibrium therewith.

Another such aspect relates to an apparatus for determining a genetic indicator for type 2 diabetes in a human individual, comprising (i) a processor; and (ii) a computer readable memory having computer executable instructions adapted to be executed on the processor to analyze marker and/or haplotype information for at least one human individual with respect to at least one polymorphic marker selected from the group consisting of rs2237892, rs231362, rs4731702 and rs2334499, and markers in linkage disequilibrium therewith, and generate an output based on the marker or haplotype information, wherein the output comprises a risk measure of the at least one marker or haplotype as a genetic indicator of type 2 diabetes for the human individual.

In one embodiment, the computer readable memory further comprises data indicative of the risk of developing diabetes mellitus associated with at least one allele of at least one polymorphic marker or at least one haplotype, and wherein a risk measure for the human individual is based on a comparison of the at least one marker and/or haplotype status for the human individual to the risk of diabetes mellitus associated with the at least one allele of the at least one polymorphic marker or the at least one haplotype.

In another embodiment, the computer readable memory further comprises data indicative_of the frequency of at least one allele of at least one polymorphic marker or at least one haplotype in a plurality of individuals diagnosed with diabetes mellitus, and data indicative of the frequency of at the least one allele of at least one polymorphic marker or at least one haplotype in a plurality of reference individuals, and wherein risk of developing diabetes mellitus is based on a comparison of the frequency of the at least one allele or haplotype in individuals diagnosed with diabetes mellitus and reference individuals.

It should be understood that all combinations of features described herein are contemplated, even if the combination of feature is not specifically found in the same sentence or paragraph herein. This includes in particular the use of all markers disclosed herein, alone or in combination, for analysis individually or in haplotypes, in all aspects of the invention as described herein.

BRIEF DESCRIPTION OF THE DRAWINGS

The foregoing and other objects, features and advantages of the invention will be apparent from the following more particular description of preferred embodiments of the invention.

DETAILED DESCRIPTION

Definitions

Figure 1:
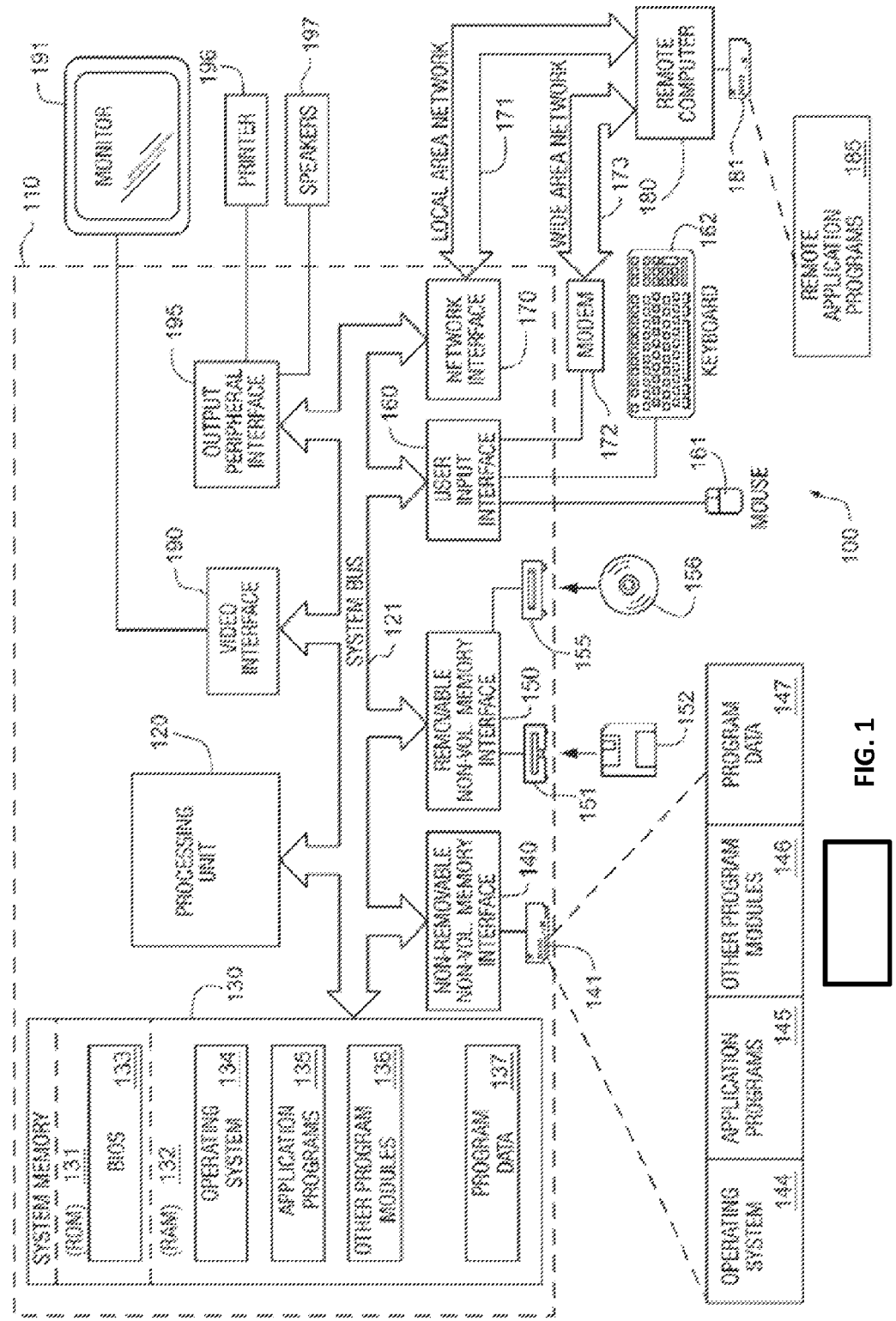
FIG. 1 provides a diagram illustrating a computer-implemented system utilizing risk variants as described herein.

Unless otherwise indicated, nucleic acid sequences are written left to right in a 5' to 3' orientation. Numeric ranges recited within the specification are inclusive of the numbers defining the range and include each integer or any non-integer fraction within the defined range. Unless defined otherwise, all technical and scientific terms used herein have the same meaning as commonly understood by the ordinary person skilled in the art to which the invention pertains.

The following terms shall, in the present context, have the meaning as indicated:

A "polymorphic marker", sometime referred to as a "marker", as described herein, refers to a genomic polymorphic site. Each polymorphic marker has at least two sequence variations characteristic of particular alleles at the polymorphic site. Thus, genetic association to a polymorphic marker implies that there is association to at least one specific allele of that particular polymorphic marker. The marker can comprise any allele of any variant type found in the genome, including SNPs, mini- or microsatellites, translocations and copy number variations (insertions, deletions, duplications). Polymorphic markers can be of any measurable frequency in the population. For mapping of disease genes, polymorphic markers with population frequency higher than 5-10% are in general most useful. However, polymorphic markers may also have lower population frequencies, such as 1-5% frequency, or even lower frequency, in particular copy number variations (CNV5). The term shall, in the present context, be taken to include polymorphic markers with any population frequency.

An "allele" refers to the nucleotide sequence of a given locus (position) on a chromosome. A polymorphic marker allele thus refers to the composition (i.e., sequence) of the marker on a chromosome. Genomic DNA from an individual contains two alleles (e.g., allele-specific sequences) for any given polymorphic marker, representative of each copy of the marker on each chromosome. Sequence codes for nucleotides used herein are: A=1, C=2, G=3, T=4. For microsatellite alleles, the CEPH sample (Centre d'Etudes du Polymorphisme Humain, genomics repository, CEPH sample 1347-02) is used as a reference, the shorter allele of each microsatellite in this sample is set as 0 and all other alleles in other samples are numbered in relation to this reference. Thus, e.g., allele 1 is 1 bp longer than the shorter allele in the CEPH sample, allele 2 is 2 bp longer than the shorter allele in the CEPH sample, allele 3 is 3 bp longer than the lower allele in the CEPH sample, etc., and allele −1 is 1 bp shorter than the shorter allele in the CEPH sample, allele −2 is 2 bp shorter than the shorter allele in the CEPH sample, etc.

Sequence conucleotide ambiguity as described herein and in the accompanying sequence listing is as proposed by IUPAC-IUB. These codes are compatible with the codes used by the EMBL, GenBank, and PIR databases.

| IUB code | Meaning |
| --- | --- |
| A | Adenosine |
| C | Cytidine |
| G | Guanine |
| T | Thymidine |
| R | G or A |
| Y | T or C |
| K | G or T |
| M | A or C |
| S | G or C |
| W | A or T |
| B | C, G or T |
| D | A, G or T |
| H | A, C or T |
| V | A, C or G |
| N | A, C, G or T (Any base) |

A nucleotide position at which more than one sequence is possible in a population (either a natural population or a synthetic population, e.g., a library of synthetic molecules) is referred to herein as a "polymorphic site".

A "Single Nucleotide Polymorphism" or "SNP" is a DNA sequence variation occurring when a single nucleotide at a specific location in the genome differs between members of a species or between paired chromosomes in an individual. Most SNP polymorphisms have two alleles. Each individual is in this instance either homozygous for one allele of the polymorphism (i.e. both chromosomal copies of the individual have the same nucleotide at the SNP location), or the individual is heterozygous (i.e. the two sister chromosomes of the individual contain different nucleotides). The SNP nomenclature as reported herein refers to the official Reference SNP (rs) ID identification tag as assigned to each unique SNP by the National Center for Biotechnological Information (NCBI).

A "variant", as described herein, refers to a segment of DNA that differs from the reference DNA. A "marker" or a "polymorphic marker", as defined herein, is a variant. Alleles that differ from the reference are referred to as "variant" alleles.

A "microsatellite" is a polymorphic marker that has multiple small repeats of bases that are 2-8 nucleotides in length (such as CA repeats) at a particular site, in which the number of repeat lengths varies in the general population. An "indel" is a common form of polymorphism comprising a small insertion or deletion that is typically only a few nucleotides long.

A "haplotype," as described herein, refers to a segment of genomic DNA that is characterized by a specific combination of alleles arranged along the segment. For diploid organisms such as humans, a haplotype comprises one member of the pair of alleles for each polymorphic marker or locus along the segment. In a certain embodiment, the haplotype can comprise two or more alleles, three or more alleles, four or more alleles, or five or more alleles. Haplotypes are described herein in the context of the marker name and the allele of the marker in that haplotype, e.g., "T rs2334499" refers to the 4 allele of marker rs2334499 being in the haplotype, and is equivalent to "rs2334499 allele 4". Furthermore, allelic codes in haplotypes are as for individual markers, i.e. 1=A, 2=C, 3=G and 4=T.

The term "susceptibility", as described herein, refers to the proneness of an individual towards the development of a certain state (e.g., a certain trait, phenotype or disease), or towards being less able to resist a particular state than the average individual. The term encompasses both increased susceptibility and decreased susceptibility. Thus, particular alleles at polymorphic markers and/or haplotypes of the invention as described herein may be characteristic of increased susceptibility (i.e., increased risk) of type 2 diabetes, as characterized by a relative risk (RR) or odds ratio (OR) of greater than one for the particular allele or haplotype. Alternatively, the markers and/or haplotypes of the invention are characteristic of decreased susceptibility (i.e., decreased risk) of type 2 diabetes, as characterized by a relative risk of less than one.

The term "and/or" shall in the present context be understood to indicate that either or both of the items connected by it are involved. In other words, the term herein shall be taken to mean "one or the other or both".

The term "look-up table", as described herein, is a table that correlates one form of data to another form, or one or more forms of data to a predicted outcome to which the data is relevant, such as phenotype or trait. For example, a look-up table can comprise a correlation between allelic data for at least one polymorphic marker and a particular trait or phenotype, such as a particular disease diagnosis, that an individual who comprises the particular allelic data is likely to display, or is more likely to display than individuals who do not comprise the particular allelic data. Look-up tables can be multidimensional, i.e. they can contain information about multiple alleles for single markers simultaneously, or they can contain information about multiple markers, and they may also comprise other factors, such as particulars about diseases, diagnoses, racial information, biomarkers, biochemical measurements, therapeutic methods or drugs, etc.

A "computer-readable medium", is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

A "nucleic acid sample" as described herein, refers to a sample obtained from an individual that contains nucleic acid (DNA or RNA). In certain embodiments, i.e. the detection of specific polymorphic markers and/or haplotypes, the nucleic acid sample comprises genomic DNA. Such a nucleic acid sample can be obtained from any source that contains genomic DNA, including a blood sample, sample of amniotic fluid, sample of cerebrospinal fluid, or tissue sample from skin, muscle, buccal or conjunctival mucosa, placenta, gastrointestinal tract or other organs.

The term "therapeutic agent for type 2 diabetes" refers to an agent that can be used to ameliorate or prevent symptoms associated with type 2 diabetes.

The term "type 2 diabetes-associated nucleic acid", as described herein, refers to a nucleic acid that has been found to be associated to type 2 diabetes. This includes, but is not limited to, the markers and haplotypes described herein and markers and haplotypes in strong linkage disequilibrium (LD) therewith. In one embodiment, a type 2 diabetes-associated nucleic acid refers to an LD-block found to be associated with Type 2 diabetes through at least one polymorphic marker located within the LD block.

The term "antisense agent" or "antisense oligonucleotide" refers, as described herein, to molecules, or compositions comprising molecules, which include a sequence of purine an pyrimidine heterocyclic bases, supported by a backbone, which are effective to hydrogen bond to a corresponding contiguous bases in a target nucleic acid sequence. The backbone is composed of subunit backbone moieties supporting the purine and pyrimidine heterocyclic bases at positions which allow such hydrogen bonding. These backbone moieties are cyclic moieties of 5 to 7 atoms in size, linked together by phosphorous-containing linkage units of one to three atoms in length. In certain preferred embodiments, the antisense agent comprises an oligonucleotide molecule.

The term "LD Block C11", as described herein, refers to the genomic segment on chromosome 11 between position 1,625,434 and 1,672,208 (inclusive) in the human genome assembly Build 36. The segment has sequence as set forth in SEQ ID NO:7 herein.

Identification of Susceptibility Variants for Type 2 Diabetes

The present inventors have discovered that certain genetic variants confer increased risk of type 2 diabetes. A search for variants associated with type 2 diabetes has revealed that markers in several genomic locations are associated with risk of type 2 diabetes. The inventors have also discovered that certain variants confer risk of breast cancer and basal cell carcinoma. In all cases, the effect of the associated markers is through a mechanism that depends on the parental origin of the associated allele. In other words, the effect is dependent on the parental origin of the associated allele.

Chromosome 11p15 Locus

An association with type 2 diabetes was observed in two distinct regions of chromosome 11p15. Marker rs231362 has previously been reported to be associated with type 2 diabetes. The present inventors have surprisingly found that maternal transmission of the C allele of this marker is associated with increased risk of type 2 diabetes. The present inventors have also surprisingly discovered another variant, rs2334499, in the chromosome 11p15 region that is associated with risk of type 2 diabetes. The association of this marker is striking in that a paternal transmission of the T allele is associated with increased risk of type 2 diabetes, while a maternal transmission of the same allele is associated with a decreased risk of type 2 diabetes. The observed overall risk for the marker, ignoring these parent-of-origin effects, is thus an average of these underlying effects.

The effects of rs231362 and rs2334499 on risk of type 2 diabetes appear to be independent. Thus, both of these markers, and surrogate markers in linkage disequilibrium therewith, can be used to detect an association to diabetes. Surrogate markers for rs2334499, which can also be used to detect the association observed for this marker to type 2 diabetes, are listed in Table 1 (A and B) below. Such surrogate markers are useful in the methods, apparatus and kits of the invention, as further described herein. Thus, in certain embodiments, markers useful for detecting a susceptibility to type 2 diabetes are selected from the group consisting of rs2334499, rs1038727, rs7131362, rs748541, rs4752779, rs4752780, rs4752781, rs4417225, rs10769560, rs17245346, rs11607954, rs10839220, rs11600502, s.1625734, s.1638067, s.1638081, s.1643366, rs28526166, rs7109305, rs12360952, rs7112918, s.1648379, s.1648786, s.1648802, s.1649074, s.1650392, rs12283736, rs10838695, rs10769275, s.1657176, s.1659505, s.1660547, s.1662049, s.1662089, s.1662163, s.1662228, s.1662252, s.1663159, s.1663161, rs7102894, s.1663762, s.1664515, s.1664655, s.1667464, s.1667475, s.1667517, s.1668164, rs35944603, s.1669681, s.1669874, s.1669942, s.1670552, and s.1671908.

TABLE 1 (A)

Surrogate markers for rs2334499 (SEQ ID NO: 1), obtained using the Caucasian HapMap dataset (http://www.hapmap.org). Shown is the marker, position on chromosome 11 in NCBI Build 36 of the human genome assembly, associated allele to allele T of rs2334499, LD measures and position of the marker in SEQ ID NO: 7.
Surrogates for rs2334499 allele T

| SNP | Pos B36 | Allele | D' | r² | p-value | Pos in Seq ID No 7 |
|---|---|---|---|---|---|---|
| rs1038727 | 1637577 | T | 0.74 | 0.21 | 1.5E−06 | 12144 |
| rs7131362 | 1645901 | G | 0.66 | 0.24 | 8.1E−08 | 20468 |
| rs748541 | 1652592 | A | 1.00 | 0.35 | 6.8E−14 | 27159 |
| rs2334499 | 1653425 | T | 1 | 1 | | 27992 |
| rs4752779 | 1658046 | G | 1.00 | 0.31 | 4.8E−12 | 32613 |
| rs4752780 | 1658460 | C | 0.97 | 0.90 | 8.5E−31 | 33027 |
| rs4752781 | 1658631 | T | 0.97 | 0.87 | 9.5E−30 | 33198 |
| rs4417225 | 1660140 | A | 0.97 | 0.93 | 1.0E−31 | 34707 |
| rs10769560 | 1670637 | G | 0.94 | 0.33 | 1.0E−10 | 45204 |
| rs17245346 | 1671223 | T | 0.91 | 0.68 | 7.3E−19 | 45790 |
| rs11607954 | 1671264 | C | 0.96 | 0.59 | 4.0E−19 | 45831 |
| rs10839220 | 1671312 | C | 0.95 | 0.55 | 7.7E−18 | 45879 |
| rs11600502 | 1671560 | A | 0.63 | 0.20 | 2.3E−06 | 46127 |

TABLE 1 (B)

Surrogate markers for rs2334499, obtained using the publically available 1000 Genomes project (http://www.1000genomes.org). Markers that have not been assigned rs names are identified by their position in NCBI Build 36 of the human genome assembly. Shown is the marker, position on chromosome 11 in NCBI Build 36 of the human genome assembly, associated allele to allele T of rs2334499, LD measures and position of the marker in SEQ ID NO: 7.

| SNP | Pos. in NCBI B36 | Allele | D' | r2 | P-value | Pos in Seq ID NO 7. |
|---|---|---|---|---|---|---|
| s.1625734 | 1625734 | G | 0.88 | 0.22 | 0.000063 | 301 |
| rs1038727 | 1637577 | A | 0.67 | 0.2 | 0.00048 | 12144 |
| s.1638067 | 1638067 | T | 0.67 | 0.2 | 0.00048 | 12634 |
| s.1638081 | 1638081 | T | 0.67 | 0.2 | 0.00048 | 12648 |
| s.1643366 | 1643366 | A | 0.68 | 0.21 | 0.00025 | 17933 |
| rs28526166 | 1643383 | G | 0.85 | 0.3 | 0.00000062 | 17950 |
| rs7131362 | 1645901 | G | 0.86 | 0.33 | 0.000000096 | 20468 |
| rs7109305 | 1647042 | C | 1 | 0.2 | 0.000000012 | 21609 |
| rs12360952 | 1647463 | C | 0.6 | 0.3 | 0.0000017 | 22030 |
| rs7112918 | 1647545 | C | 0.68 | 0.37 | 0.00000026 | 22112 |
| s.1648379 | 1648379 | T | 0.81 | 0.38 | 0.000000066 | 22946 |
| s.1648786 | 1648786 | A | 1 | 0.31 | 1.2E−10 | 23353 |
| s.1648802 | 1648802 | T | 1 | 0.39 | 4.8E−13 | 23369 |
| s.1649074 | 1649074 | C | 0.88 | 0.69 | 1.3E−14 | 23641 |
| s.1650392 | 1650392 | T | 1 | 0.2 | 0.000000012 | 24959 |
| rs12283736 | 1651997 | A | 1 | 0.93 | 3.8E−31 | 26564 |
| rs748541 | 1652592 | A | 1 | 0.3 | 8.4E−12 | 27159 |
| rs10838695 | 1653790 | A | 1 | 0.25 | 2.5E−10 | 28357 |
| rs10769275 | 1655721 | C | 1 | 0.27 | 1.1E−10 | 30288 |
| s.1657176 | 1657176 | C | 0.89 | 0.22 | 0.000093 | 31743 |
| rs4752779 | 1658046 | G | 1 | 0.25 | 2.5E−10 | 32613 |
| rs4752780 | 1658460 | C | 0.92 | 0.82 | 1.2E−19 | 33027 |
| rs4752781 | 1658631 | T | 0.92 | 0.82 | 1.2E−19 | 33198 |
| s.1659505 | 1659505 | A | 0.92 | 0.82 | 3.5E−19 | 34072 |
| rs4417225 | 1660140 | T | 0.92 | 0.82 | 3.5E−19 | 34707 |
| s.1660547 | 1660547 | T | 1 | 0.57 | 1.2E−18 | 35114 |
| s.1662049 | 1662049 | T | 0.89 | 0.79 | 3E−18 | 36616 |
| s.1662089 | 1662089 | C | 0.85 | 0.32 | 0.0000029 | 36656 |
| s.1662163 | 1662163 | A | 0.92 | 0.82 | 3.5E−19 | 36730 |
| s.1662228 | 1662228 | G | 0.87 | 0.64 | 1.4E−13 | 36795 |

TABLE 1 (B)-continued

Surrogate markers for rs2334499, obtained using the publically available 1000 Genomes project (http://www.1000genomes.org). Markers that have not been assigned rs names are identified by their position in NCBI Build 36 of the human genome assembly. Shown is the marker, position on chromosome 11 in NCBI Build 36 of the human genome assembly, associated allele to allele T of rs2334499, LD measures and position of the marker in SEQ ID NO: 7.

| SNP | Pos. in NCBI B36 | Allele | D' | r2 | P-value | Pos in Seq ID NO 7. |
|---|---|---|---|---|---|---|
| s.1662252 | 1662252 | C | 1 | 0.27 | 1.1E−10 | 36819 |
| s.1663159 | 1663159 | T | 0.96 | 0.82 | 2.5E−19 | 37726 |
| s.1663161 | 1663161 | T | 0.96 | 0.82 | 2.5E−19 | 37728 |
| rs7102894 | 1663514 | C | 0.92 | 0.82 | 3.5E−19 | 38081 |
| s.1663762 | 1663762 | T | 0.88 | 0.75 | 1.9E−17 | 38329 |
| s.1664515 | 1664515 | G | 0.92 | 0.41 | 0.000000045 | 39082 |
| s.1664655 | 1664655 | C | 0.86 | 0.56 | 9.7E−12 | 39222 |
| s.1667464 | 1667464 | T | 0.88 | 0.75 | 2.8E−17 | 42031 |
| s.1667475 | 1667475 | G | 0.88 | 0.75 | 2.8E−17 | 42042 |
| s.1667517 | 1667517 | T | 0.89 | 0.79 | 3E−18 | 42084 |
| s.1668164 | 1668164 | G | 0.88 | 0.75 | 1.9E−17 | 42731 |
| rs35944603 | 1668394 | C | 1 | 0.28 | 4.7E−11 | 42961 |
| s.1669681 | 1669681 | A | 0.92 | 0.28 | 0.000000056 | 44248 |
| s.1669874 | 1669874 | T | 0.92 | 0.28 | 0.000000056 | 44441 |
| s.1669942 | 1669942 | A | 0.92 | 0.41 | 0.000000045 | 44509 |
| s.1670552 | 1670552 | T | 0.89 | 0.79 | 3E−18 | 45119 |
| rs10769560 | 1670637 | G | 0.92 | 0.28 | 0.00000011 | 45204 |
| rs17245346 | 1671223 | T | 0.88 | 0.69 | 1.6E−15 | 45790 |
| rs11607954 | 1671264 | C | 0.9 | 0.51 | 1E−11 | 45831 |
| rs10839220 | 1671312 | C | 0.89 | 0.45 | 5.5E−11 | 45879 |
| s.1671908 | 1671908 | C | 0.65 | 0.35 | 0.00000021 | 46475 |

On chromosome 11p15, marker rs3817198 (seq ID NO: 5) was also surprisingly found to exhibit a parent-of-origin effect. The paternally inherited C allele of this marker was found to be significantly associated with breast cancer, illustrating that the observed association for this marker is due to a paternal transmission of the risk allele.

As illustrated herein in Example 1, the present inventors have also shown that rs2334499 T is correlated with increased methylation of differentially methylated CpGs at a CTCF binding site. This correlation is independent of parent of origin of the T allele. Given the well established role of CTCF in imprinting regulation that has been studied extensively at the nearby H19/IGF2 locus, and the differential methylation demonstrated here, we propose that this site is in fact an imprinting control region. The following model could account for the opposite effect of the T allele on risk of T2D, dependent on parent of origin. The model assumes that monoallelic expression of hitherto unidentified genes is dependent on hypomethylation of the paternal allele and hypermethylation of the maternal allele at this proposed imprinting control region. When the T allele is on the maternal chromosome, methylation of the already methylated maternal chromosome is enhanced while the paternally transmitted T allele increases methylation of the hypomethylated paternal allele. The paternally and maternally transmitted alleles would thereby affect monoallelic expression of the regulated genes in very different ways. As a consequence, it is contemplated that through determination of the methylation status of individuals, susceptibility of type 2 diabetes may be determined, in the absence of a determination of the parental origin of particular alleles. In other words, determination of the methylation status at particular sites, in combination of the determination of the allelic status of particular polymorphic markers, such as rs2334499, determination of susceptibility may be made, which indirectly is representative of the parental origin of the particular alleles.

Chromosome 7q32 Locus

The inventors have found that the C allele of marker rs4731702 (seq ID NO 4) is associated with risk of type 2 diabetes when maternally inherited. No association was observed for the allele when paternally inherited.

Likewise, the association of the T allele of rs157935 (seq ID NO:6) to basal cell carcinoma was found to be parent-of-origin specific. Thus, the risk for the paternally inherited T allele was highly significant (OR=1.40, p=1.5×10$^{-6}$), while the maternally inherited allele, while in the same direction, was not significant (OR=1.09, p=0.19).

Methods of Determining Susceptibility to Type 2 Diabetes

Accordingly, the present invention provides materials and methods for determining a susceptibility to type 2 diabetes in human individuals, as further described in the following.

In one aspect the invention provides a method of determining a susceptibility to type 2 diabetes in a human individual, the method comprising (i) obtaining nucleic acid sequence data about a human individual identifying at least one allele of at least one polymorphic marker, wherein different alleles of the at least one polymorphic marker are associated with different susceptibilities to type 2 diabetes in humans, and (ii) determining a susceptibility to type 2 diabetes from the sequence data, wherein the at least one polymorphic marker is selected from the group consisting of rs2334499, and markers in linkage disequilibrium therewith.

Another aspect provides a method of determining a susceptibility to type 2 diabetes in a human individual, the method comprising (i) analyzing nucleic acid sequence data from a human individual for at least one polymorphic marker selected from the group consisting of rs2334499, and markers in linkage disequilibrium therewith, wherein different alleles of the at least one polymorphic marker are associated with different susceptibilities to type 2 diabetes in humans, and (ii) determining a susceptibility to type 2 diabetes from the nucleic acid sequence data.

Certain aspects relate to determination of susceptibility based on a particular parental origin og inherited alleles. Thus, one aspect of the invention relates to a method of determining a susceptibility to type 2 diabetes in a human individual, the method comprising (i) analyzing nucleic acid sequence data identifying the parental origin of at least one allele of at least one polymorphic marker in the genome of the individual, wherein different parental origins of the at least one allele are indicative of different susceptibilities to type 2 diabetes in humans; and (ii) determining a susceptibility to type 2 diabetes from the sequence data; wherein the at least one polymorphic marker is selected from the group consisting of rs2237892, rs231362, rs4731702 and rs2334499, and markers in linkage disequilibrium therewith.

In certain embodiments, determination of a paternal origin of allele T of rs2334499, or an allele in linkage disequilibrium therewith, is indicative of increased susceptibility of type 2 diabetes in the human individual. Determination of a maternal origin of the T allele of rs2334499, or an allele in linkage disequilibrium therewith, is in certain embodiments indicative of a decreased susceptibility of, or a protection against, type 2 diabetes.

In certain embodiments, determination of a maternal origin of an allele selected from the group consisting of allele C of rs2237892, allele C of rs231362 and allele C of rs4731702, or alleles in linkage disequilibrium therewith, is indicative of an increased susceptibility of type 2 diabetes.

Methods of Determining Susceptibility to Breast Cancer

Certain aspects of the invention relate to methods of determining susceptibility to breast cancer. In one such aspect, the invention provides a method of determining a susceptibility to breast cancer in a human individual, the method comprising (i) analyzing nucleic acid sequence data identifying the parental origin of at least one allele of at least one polymorphic marker in the genome of the individual, wherein different parental origins of the at least one allele are indicative of different susceptibilities to breast cancer in humans; and (ii) determining a susceptibility to breast cancer from the sequence data; wherein the at least one polymorphic marker is selected from the group consisting of rs3817198, and markers in linkage disequilibrium therewith.

In certain embodiments, determination of a paternal origin of allele C of rs3817198, or a marker allele in linkage disequilibrium therewith, is indicative of increased susceptibility to breast cancer in the individual.

Methods of Determining Susceptibility to Basal Cell Carcinoma

The invention also relates to methods of determining susceptibility to basal cell carcinoma. In one such aspect, the invention provides a method of determining a susceptibility to basal cell carcinoma in a human individual, the method comprising (i) analyzing nucleic acid sequence data identifying the parental origin of at least one allele of at least one polymorphic marker in the genome of the individual, wherein different parental origins of the at least one allele are indicative of different susceptibilities to basal cell carcinoma in humans; and (ii) determining a susceptibility to basal cell carcinoma from the sequence data; wherein the at least one polymorphic marker is selected from the group consisting of rs157935, and markers in linkage disequilibrium therewith.

In certain embodiments, determination of a paternal origin of allele T of rs157935, or a marker allele in linkage disequilibrium therewith, is indicative of increased susceptibility to breast cancer in the individual.

The invention thus provides methods of determining susceptibility of these diseases in a human individual, through obtaining sequence data about a human individual identifying at least one allele of at least one polymorphic marker, wherein different alleles of the marker are associated with different susceptibilities to the disease in humans, and determining a susceptibility to the disease from the sequence data. Certain embodiments relate to analyzing sequence data about a human individual identifying at least one allele of at least one polymorphic marker, wherein different alleles of the marker are associated with different susceptibilities to the disease in humans, and determining a susceptibility to the disease from the sequence data. In certain embodiments, the methods include a further step of determining the parental origin of the at least one allele, where different parental origins are associated with different risk of the disease in humans.

Determination of parental origin may be performed using techniques known in the art. For example, methods as outlined in Kong et al (*Nature* 462:868-875 (2009)) and also described in Example 1 herein may be used.

In certain embodiments, the sequence data is nucleic acid sequence data. Nucleic acid sequence data identifying particular alleles of polymorphic markers is sometimes also referred to as genotype data. Nucleic acid sequence data can be obtained for example by analyzing sequence of the at least one polymorphic marker in a biological sample from the individual. Alternatively, nucleic acid sequence data can be obtained in a genotype dataset from the human individual and analyzing sequence of the at least one polymorphic marker in the dataset. Such analysis in certain embodiments comprises determining the presence or absence of a particular allele of specific polymorphic markers. Identification of particular alleles in general terms should be taken to mean that determination of the presence or absence of the allele(s) is made.

Usually, determination of both allelic copies in the genome of an individual is performed, by determining the occurrence of all possible alleles of the particular polymorphism in a particular individual (for SNPs, each of the two possible nucleotides possible for the allelic site). It is also possible to determine whether only particular alleles are present or not. For example, in certain embodiments, determination of the presence or absence of certain alleles that have been shown to associate with risk of glaucoma is made, but not necessarily other alleles of the particular marker, and a determination of susceptibility is made based on such determination. In certain embodiments, sequence data about at least two polymorphic markers is obtained.

Surrogate markers in linkage disequilibrium with particular key markers can be selected based on certain values of the linkage disequilibrium measures D' and $r^2$, as described further herein. For example, markers that are in linkage disequilibrium with rs2334499 are exemplified by the markers listed in Table 1 herein, but the skilled person will appreciate that other markers in linkage disequilibrium with this marker may also be used in the diagnostic applications described herein. Further, as also described in more detail herein, the skilled person will appreciate that since linkage disequilibrium is a continuous measure, certain values of the LD measures D' and $r^2$ may be suitably chosen to define markers that are useful as surrogate markers in LD with the markers described herein. Numeric values of D' and $r^2$ may thus in certain embodiments be used to define marker subsets that fulfill certain numerical cutoff values of D' and/or $r^2$. In one embodiment, markers in linkage disequilibrium with a particular anchor marker (e.g., rs2334499) are in LD with the anchor marker characterized by numerical values of D' of greater than 0.8 and/or numerical values of $r^2$ of greater than 0.2. In one embodiment, markers in linkage disequilibrium with a particular anchor marker are in LD with the anchor marker characterized by numerical values of $r^2$ of greater than 0.2. The markers provided in Table 1 provide exemplary markers that fulfill this criterion. In other embodiments, markers in linkage disequilibrium with a particular anchor marker are in LD with the anchor marker characterized by numerical values of $r^2$ of greater than 0.3, greater than 0.4, greater than 0.5, greater than 0.6, greater than 0.7, greater than 0.8, greater than 0.9, greater than 0.95. Other numerical values of $r^2$ and/or D' may also be suitably selected to select markers that are in LD with the anchor marker. The stronger the LD, the more similar the association signal and/or the predictive risk by the surrogate marker will be to that of the anchor marker. Markers with values of $r^2=1$ to the anchor marker are perfect surrogates of the anchor marker and will provide identical association and risk prediction data.

In certain embodiments, markers alleles that are in linkage disequilibrium with allele T of rs2334499 are suitably selected from the group consisting of rs1038727 allele T, rs7131362 allele G, rs748541 allele A, rs4752779 allele G, rs4752780 allele C, rs4752781 allele T, rs4417225 allele A, rs10769560 allele G, rs17245346 allele T, rs11607954 allele C, rs10839220 allele C, rs11600502 allele A, s.1625734 allele G, s.1638067 allele T, s.1638081 allele T, s.1643366 allele A, rs28526166 allele G, rs7109305 allele C, rs12360952 allele C, rs7112918 allele C, s.1648379 allele T, s.1648786 allele A, s.1648802 allele T, s.1649074 allele C, s.1650392 allele T, rs12283736 allele A, rs10838695 allele A, rs10769275 allele C, s.1657176 allele C, s.1659505 allele A, s.1660547 allele T, s.1662049 allele T, s.1662089 allele C, s.1662163 allele A, s.1662228 allele G, s.1662252 allele C, s.1663159 allele T, s.1663161 allele T, rs7102894 allele C, s.1663762 allele T, s.1664515 allele G, s.1664655 allele C, s.1667464 allele T, s.1667475 allele G, s.1667517 allele T, s.1668164 allele G, rs35944603 allele C, s.1669681 allele A, s.1669874 allele T, s.1669942 allele A, s.1670552 allele T, and s.1671908 allele C. Such marker alleles are thus surrogates of rs2334499 allele T. Paternal transmission of these alleles is predicted to be indicative of increased risk of type 2 diabetes, while a maternal transmission of these alleles is predicted to be indicative of decreased risk of type 2 diabetes.

Association data presented in Table 4 illustrate that surrogate markers of rs2334499 are indeed associated with type 2 diabetes. More particularly, paternal transmission of particular at-risk alleles of surrogate markers of rs2334499 is indicative of risk of type 2 diabetes. Surrogate markers give different association signals depending on how strongly they are correlated with the underlying signal. Consider, for example, the markers rs28526166, rs4417225 and rs17245346, which are all surrogate markers of rs4236601. For all of these markers, paternal transmission of the effect allele is indicative of increased risk of type 2 diabetes (i.e. it is an at-risk allele), while a maternal transmission of the effect allele is indicative of a decreased risk of type 2 diabetes (i.e., it is a protective allele when maternally inherited). The strongest association signal is observed for rs4417225 (OR1.31 for paternal transmission of T allele, P-value 3.1E-7; see Table 4), while slightly weaker association is observed for rs17245346 (OR for paternal transmission of T allele 1.30, P-value 3.3E-6) and rs28526166 (OR1.18 for paternal transmission of G allele, P-value 0.0011). All three are useful surrogates of rs2334499, but capture the underlying association signal to a varying degree-values of the LD measure $r^2$ to rs2334499 are 0.93, 0.68 and 0.30, respectively, for rs4417225, rs17245346 and rs28526166. It should also be noted that sample size also has an effect of the power to detect an underlying association. This power is exemplified by the apparent P-value of association determined using the particular sample. This does not mean that the inherent strength of each surrogate marker is affected, but is rather a manifestation of the relative strength of such markers in capturing the underlying association. The weaker the correlation to the anchor marker, the large a sample size will be needed to capture the underlying association with a particular statistical certainty.

Thus, in certain embodiments, markers in linkage disequilibrium with rs4236601 are selected from the group consisting of rs4752781, s.1649074, rs12283736, s.1663159, s.1663161, s.1667464, s.1663762, rs7102894, rs4752780, s.1668164, s.1667475, s.1667517, s.1670552, s.1659505, rs4417225, s.1662049, s.1662163, rs17245346, rs10839220, s.1662089, s.1671908, s.1669942, rs11607954, s.1662228, rs7112918, rs4752779, rs10838695, rs748541, s.1657176, rs7131362, rs28526166, rs10769560, rs12360952, rs10769275, rs11600502, s.1662252, rs35944603, s.1669681, s.1669874, which are the markers in Table 4 for which a statistically significant (p<0.05) association of the paternally transmitted effect allele with type 2 diabetes has been shown.

The sequence data that is obtained may in certain embodiments be amino acid sequence data. Polymorphic markers can result in alterations in the amino acid sequence of encoded polypeptide or protein sequence. In certain embodiments, the analysis of amino acid sequence data comprises determining the presence or absence of an amino acid substitution in the amino acid encoded by the at least one polymorphic marker. Sequence data can in certain embodiments be obtained by analyzing the amino acid sequence encoded by the at least one polymorphic marker in a biological sample obtained from the individual. In certain embodiments, the at least one polymorphic marker that is assessed is an amino acid substitution in a polypeptide encoded by the human HCCA2 gene. In other words, the marker may be an amino acid substitution in a human HCCA2 polypeptide.

Measures of susceptibility or risk include measures such as relative risk (RR), odds ratio (OR), and absolute risk (AR), as described in more detail herein.

In certain embodiments, increased susceptibility is reported as a risk of at least 1.10, at least 1.11, at least 1.12, at least 1.13, at least 1.14, at least 1.15, at least 1.16, at least 1.17, at least 1.18, at least 1.19, at least 1.20, at least 1.21, at least 1.22, at least 1.23, at least 1.24, at least 1.25, at least 1.26, at least 1.27, at least 1.28, at least 1.29, at least 1.30, at least 1.35, at least 1.40, and at least 1.50. Other numerical non-integer values are also possible to characterize the risk, and such numerical values are also within scope of the invention. Certain embodiments relate to homozygous individuals for a particular markers, i.e. individuals who carry two copies of the same allele in their genome. One embodiment relates to individuals who are homozygous carriers of allele T of rs2334499, or a marker allele in linkage disequilibrium therewith.

In certain other embodiments, determination of the presence of particular marker alleles or particular haplotypes is predictive of a decreased susceptibility of a disease in humans. For SNP markers with two alleles, the alternate allele to an at-risk allele will be in decreased frequency in patients compared with controls. For alleles with parental origin effects, one allelic origin (paternal or maternal) may confer risk, while the other is neutral (i.e., does not confer risk and is also not protective). In certain embodiments, one allelic origin confers a risk, while the other allelic origin confers a protection against the disease. For example, allele T of rs2334499 is at risk when paternally inherited, but is protective when maternally inherited.

To identify markers that are useful for assessing susceptibility to a disease, it may be useful to compare the frequency of markers alleles in individuals with glaucoma to control individuals. The control individuals may be a random sample from the general population, i.e. a population cohort. The control individuals may also be a sample from individuals that do are disease-free, e.g. individuals who have been confirmed not to have glaucoma. In one embodiment, an increase in frequency of at least one allele in at least one polymorphism in individuals diagnosed with the disease, as compared with the frequency of the at least one allele in the control group is indicative of the at least one allele being useful for assessing increased susceptibility to the disease. In another embodiment, a decrease in frequency of at least one allele in at least one polymorphism in individuals diagnosed with the disease, as compared with the frequency of the at least one allele in the control sample is indicative of the at least one allele being useful for assessing decreased susceptibility to, or protection against, the disease. In certain embodiments, a further step of determining the parental origin of the at least one allele is performed, wherein a particular parental origin confers risk of the disease, i.e. individuals with the disease tend to have inherited the allele from either their father or their mother more often than individuals who do not have the disease.

In general, sequence data can be obtained by analyzing a sample from an individual, or by analyzing information about specific markers in a database, for example a genotype database or a sequence database. The sample is in certain embodiments a nucleic acid sample. Analyzing a sample from an individual may in certain embodiments include steps of isolating genomic nucleic acid from the sample, amplifying a segment of the genomic nucleic acid that contains at least one polymorphic marker, and determine sequence information about the at least one polymorphic marker. Amplification is preferably performed by Polymerase Chain Reaction (PCR) techniques. In certain embodiments, sequence data can be obtained through nucleic acid sequence information or amino acid sequence information from a preexisting record. Such a preexisting record can be any documentation, database or other form of data storage containing such information.

Determination of a susceptibility or risk of a particular individual in general comprises comparison of the genotype information (sequence information, optionally also including information on parental origin) to a record or database providing a correlation about particular polymorphic marker(s) and susceptibility to the disease. Thus, in specific embodiments, determining a susceptibility comprises comparing the sequence data to a database containing correlation data between the at least one polymorphic marker and susceptibility to the disease. In certain embodiments, the database comprises at least one measure of susceptibility to the disease for the at least one polymorphic marker. In certain embodiments, the database comprises a look-up table comprising at least one measure of susceptibility to the disease for the at least one polymorphic marker. The measure of susceptibility may in the form of relative risk (RR), absolute risk (AR), percentage (%) or other convenient measure for describing genetic susceptibility of individuals.

Certain embodiments of the invention relate to markers associated with the human HCCA2 gene as predictive of risk of type 2 diabetes. Markers that are associated with these genes are in certain embodiments markers that are in linkage disequilibrium (LD) with at least one genetic marker within the genes. In certain embodiments, the markers are located within the genomic segment with sequence as set forth in SEQ ID NO:7. In certain embodiments, markers associated with the HCCA2 gene are selected from the markers within the human HCCA2 gene.

In certain embodiments of the invention, more than one polymorphic marker is analyzed. In certain embodiments, at least two polymorphic markers are analyzed. Thus, in certain embodiments, nucleic acid data about at least two polymorphic markers is obtained.

In certain embodiments, a further step of analyzing at least one haplotype comprising two or more polymorphic markers is included.

Individuals who are homozygous for risk alleles (in the absence of parental origin effects) are particularly susceptible to a disease. On the other hand, individuals who do not carry such at-risk alleles are at a decreased susceptibility of developing glaucoma. For SNPs, such individuals will be homozygous for the alternate (protective) allele of the polymorphism.

Determination of susceptibility is in some embodiments reported by a comparison with non-carriers of the at-risk allele(s) of polymorphic markers, or by comparison with individuals who have inherited the allele from the alternate parent. In certain embodiments, susceptibility is reported based on a comparison with the general population, e.g. compared with a random selection of individuals from the population.

In certain embodiments, polymorphic markers are detected by sequencing technologies. Obtaining sequence information about an individual identifies particular nucleotides in the context of a nucleic acid sequence. For SNPs, sequence information about a single unique sequence site is sufficient to identify alleles at that particular SNP. For markers comprising more than one nucleotide, sequence information about the genomic region of the individual that contains the polymorphic site identifies the alleles of the individual for the particular site. The sequence information can be obtained from a sample from the individual. In certain embodiments, the sample is a nucleic acid sample. In certain other embodiments, the sample is a protein sample.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information. These include pyrosequencing technology (Ronaghi, M. et al. *Anal Biochem* 267:65-71 (1999); Ronaghi, et al. *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLiD) technology (Applied Biosystems, http://www.appliedbiosystems.com); Strausberg, R L, et al *Drug Disc Today* 13:569-577 (2008).

Assessment for Markers and Haplotypes

The genomic sequence within populations is not identical when individuals are compared. Rather, the genome exhibits sequence variability between individuals at many locations in the genome. Such variations in sequence are commonly referred to as polymorphisms, and there are many such sites within each genome. For example, the human genome exhibits sequence variations which occur on average every 500 base pairs. The most common sequence variant consists of base variations at a single base position in the genome, and such sequence variants, or polymorphisms, are commonly called Single Nucleotide Polymorphisms ("SNPs"). These SNPs are believed to have occurred in a single mutational event, and therefore there are usually two possible alleles possible at each SNP site; the original allele and the mutated allele. Due to natural genetic drift and possibly also selective pressure, the original mutation has resulted in a polymorphism characterized by a particular frequency of its alleles in any given population. Many other types of sequence variants are found in the human genome, including mini- and microsatellites, and insertions, deletions and inversions (also called copy number variations (CNVs)). A polymorphic microsatellite has multiple small repeats of bases (such as CA repeats, TG on the complimentary strand) at a particular site in which the number of repeat lengths varies in the general population. In general terms, each version of the sequence with respect to the polymorphic site represents a specific allele of the polymorphic site. These sequence variants can all be referred to as polymorphisms, occurring at specific polymorphic sites characteristic of the sequence variant in question. In general terms, polymorphisms can comprise any number of specific alleles. Thus in one embodiment of the invention, the polymorphism is characterized by the presence of two or more alleles in any given population. In another embodiment, the polymorphism is characterized by the presence of three or more alleles. In other embodiments, the polymorphism is characterized by four or more alleles, five or more alleles, six or more alleles, seven or more alleles, nine or more alleles, or ten or more alleles. All such polymorphisms can be utilized in the methods and kits of the present invention, and are thus within the scope of the invention.

Due to their abundance, SNPs account for a majority of sequence variation in the human genome. Over 6 million SNPs have been validated to date (http://www.ncbi.nlm.nih.gov/projects/SNP/snp_summary.cgi). However, CNVs are receiving increased attention. These large-scale polymorphisms (typically 1 kb or larger) account for polymorphic variation affecting a substantial proportion of the assembled human genome; known CNVs covery over 15% of the human genome sequence (Estivill, X Armengol; L., *PloS Genetics* 3:1787-99 (2007); http://projects.tcag.ca/variation/). Most of these polymorphisms are however very rare, and on average affect only a fraction of the genomic sequence of each individual. CNVs are known to affect gene expression, phenotypic variation and adaptation by disrupting gene dosage, and are also known to cause disease (microdeletion and microduplication disorders) and confer risk of common complex diseases, including HIV-1 infection and glomerulonephritis (Redon, R., et al. *Nature* 23:444-454 (2006)). It is thus possible that either previously described or unknown CNVs represent causative variants in linkage disequilibrium with the markers described herein to be associated with type 2 diabetes. Methods for detecting CNVs include comparative genomic hybridization (CGH) and genotyping, including use of genotyping arrays, as described by Carter (*Nature Genetics* 39:S16-S21 (2007)). The Database of Genomic Variants (http://projects.tcag.ca/variation/) contains updated information about the location, type and size of described CNVs. The database currently contains data for over 15,000 CNVs.

In some instances, reference is made to different alleles at a polymorphic site without choosing a reference allele. Alternatively, a reference sequence can be referred to for a particular polymorphic site. The reference allele is sometimes referred to as the "wild-type" allele and it usually is chosen as either the first sequenced allele or as the allele from a "non-affected" individual (e.g., an individual that does not display a trait or disease phenotype).

Alleles for SNP markers as referred to herein refer to the bases A, C, G or T as they occur at the polymorphic site in the SNP assay employed. The allele codes for SNPs used herein are as follows: 1=A, 2=C, 3=G, 4=T. The person skilled in the art will however realise that by assaying or reading the opposite DNA strand, the complementary allele can in each case be measured. Thus, for a polymorphic site (polymorphic marker) characterized by an A/G polymorphism, the assay employed may be designed to specifically detect the presence of one or both of the two bases possible, i.e. A and G. Alternatively, by designing an assay that is designed to detect the complimentary strand on the DNA template, the presence of the complementary bases T and C can be measured. Quantitatively (for example, in terms of risk estimates), identical results would be obtained from measurement of either DNA strand (+strand or −strand).

Typically, a reference sequence is referred to for a particular sequence. Alleles that differ from the reference are sometimes referred to as "variant" alleles. A variant sequence, as used herein, refers to a sequence that differs from the reference sequence but is otherwise substantially similar. Alleles at the polymorphic genetic markers described herein are variants. Variants can include changes that affect a polypeptide. Sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid. For example, if the change in the nucleic acid sequence causes a frame shift, the frame shift can result in a change in the encoded amino acids, and/or can result in the generation of a premature stop codon, causing generation of a truncated polypeptide. Alternatively, a polymorphism associated with a disease or trait can be a synonymous change in one or more nucleotides (i.e., a change that does not result in a change in the amino acid sequence). Such a polymorphism can, for example, alter splice sites, affect the stability or transport of mRNA, or otherwise affect the transcription or translation of an encoded polypeptide. It can also alter DNA to increase the possibility that structural changes, such as amplifications or deletions, occur at the somatic level. The polypeptide encoded by the reference nucleotide sequence is the "reference" polypeptide with a particular reference amino acid sequence, and polypeptides encoded by variant alleles are referred to as "variant" polypeptides with variant amino acid sequences.

A haplotype refers to a segment of DNA that is characterized by a specific combination of alleles arranged along the segment. For diploid organisms such as humans, a haplotype comprises one member of the pair of alleles for each polymorphic marker or locus. In a certain embodiment, the haplotype can comprise two or more alleles, three or more alleles, four or more alleles, or five or more alleles, each allele corresponding to a specific polymorphic marker along the segment. Haplotypes can comprise a combination of various polymorphic markers, e.g., SNPs and microsatellites, having particular alleles at the polymorphic sites. The haplotypes thus comprise a combination of alleles at various genetic markers.

Detecting specific polymorphic markers and/or haplotypes can be accomplished by methods known in the art for detecting sequences at polymorphic sites. For example, standard techniques for genotyping for the presence of SNPs and/or microsatellite markers can be used, such as fluorescence-based techniques (e.g., Chen, X. et al., *Genome Res.* 9(5): 492-98 (1999); Kutyavin et al., *Nucleic Acid Res.* 34:e128 (2006)), utilizing PCR, LCR, Nested PCR and other techniques for nucleic acid amplification. Specific commercial methodologies available for SNP genotyping include, but are not limited to, TaqMan genotyping assays and SNPlex platforms (Applied Biosystems), gel electrophoresis (Applied Biosystems), mass spectrometry (e.g., MassARRAY system from Sequenomi), minisequencing methods, real-time PCR, Bio-Plex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader; Third Wave). Some of the available array platforms, including Affymetrix SNP Array 6.0 and Illumina CNV370-Duo and 1M BeadChips, include SNPs that tag certain CNVs. This allows detection of CNVs via surrogate SNPs included in these platforms. Thus, by use of these or other methods available to the person skilled in the art, one or more alleles at polymorphic markers, including microsatellites, SNPs or other types of polymorphic markers, can be identified.

In certain embodiments, polymorphic markers are detected by sequencing technologies. Obtaining sequence information about an individual identifies particular nucleotides in the context of a sequence. For SNPs, sequence information about a single unique sequence site is sufficient to identify alleles at that particular SNP. For markers comprising more than one nucleotide, sequence information about the nucleotides of the individual that contain the polymorphic site identifies the alleles of the individual for the particular site. The sequence information can be obtained from a sample from the individual. In certain embodiments, the sample is a nucleic acid sample. In certain other embodiments, the sample is a protein sample.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information. These include pyrosequencing technology (Ronaghi, M. et al. *Anal Biochem* 267:65-71 (1999); Ronaghi, et al. *Biotechniques* 25:876-878 (1998)), e.g. 454 pyrosequencing (Nyren, P., et al. *Anal Biochem* 208:171-175 (1993)), Illumina/Solexa sequencing technology (http://www.illumina.com; see also Strausberg, R L, et al *Drug Disc Today* 13:569-577 (2008)), and Supported Oligonucleotide Ligation and Detection Platform (SOLiD) technology (Applied Biosystems, http://www.appliedbiosystems.com); Strausberg, R L, et al *Drug Disc Today* 13:569-577 (2008).

It is possible to impute or predict genotypes for un-genotyped relatives of genotyped individuals. For every un-genotyped case, it is possible to calculate the probability of the genotypes of its relatives given its four possible phased genotypes. In practice it may be preferable to include only the genotypes of the case's parents, children, siblings, half-siblings (and the half-sibling's parents), grand-parents, grand-children (and the grand-children's parents) and spouses. It will be assumed, that the individuals in the small sub-pedigrees created around each case are not related through any path not included in the pedigree. It is also assumed that alleles that are not transmitted to the case have the same frequency—the population allele frequency. The probability of the genotypes of the case's relatives can then be computed by:

$$Pr(\text{genotypes of relatives}; \theta) = \sum_{h \in \{AA, AG, GA, GG\}} Pr(h; \theta) Pr(\text{genotypes of relatives} | h),$$

where $\theta$ denotes the A allele's frequency in the cases. Assuming the genotypes of each set of relatives are independent, this allows us to write down a likelihood function for $\theta$:

$$L(\theta) = \prod_i Pr(\text{genotypes of relatives of case } i; \theta). \quad (*)$$

This assumption of independence is usually not correct. Accounting for the dependence between individuals is a difficult and potentially prohibitively expensive computational task. The likelihood function in (*) may be thought of as a pseudolikelihood approximation of the full likelihood function for $\theta$ which properly accounts for all dependencies. In general, the genotyped cases and controls in a case-control association study are not independent and applying the case-control method to related cases and controls is an analogous approximation. The method of genomic control (Devlin, B. et al., *Nat Genet.* 36, 1129-30; author reply 1131 (2004)) has proven to be successful at adjusting case-control test statistics for relatedness. We therefore apply the method of genomic control to account for the dependence between the terms in our pseudolikelihood and produce a valid test statistic.

Fisher's information can be used to estimate the effective sample size of the part of the pseudolikelihood due to un-genotyped cases. Breaking the total Fisher information, I, into the part due to genotyped cases, $I_g$, and the part due to ungenotyped cases, $I_u$, $I=I_g+I_u$, and denoting the number of genotyped cases with N, the effective sample size due to the un-genotyped cases is estimated by $$\frac{I_u}{I_g} N.$$

Determining Parental Origin of Alleles

In a general sense, determining the parental origin of particular segments in the genome requires the determination of whether an individual (proband) has inherited any particular segment from his father or from his mother. Polymorphic markers are useful for such determination, since it may be possible to determine whether particular alleles of a marker are inherited from an individual's father or mother. In the former case, the allele is said to be paternally inherited, while in the latter case, the allele is maternally inherited. Let's consider the case where an individual has the genotype g1 g2 for a marker M. His father has the genotype g1 g1 for the same marker, while his mother has the genotype g2 g2. In this case, the individual must have inherited the g1 allele from his father, while the g2 allele must be inherited from his mother.

Extending information from individual markers, a method for determining the parental origin of the entire genome of an individual can be developed. The method utilizes information that is obtained using SNP arrays, which provide information on a dense set of SNPs througout the genome (on average every 10,000 nucleotides for arrays containing approximately 300,000 SNPs). By determining haplotypes over small segments (tiles) in the genome, utilizing genotype information from about 40,000 Icelanders that have been genotyped using a SNP chip, as well as an extensive genealogy that extends back several centuries, the parental origin of each segment of the genome of a particular individual (proband) can be assigned, as described in the following:

The genome was covered with 6 cM long tiles, with 3 cM overlap between adjacent tiles. Each tile was then phased using long range phasing (LRP; Kong, A. et al. *Nature Genet.* 40:1068-75 (2008)).

For a tile T and a proband P with a haplotype A over the tile T, the numbers f(P,T,A) and m(P,T,A) were defined as the meiotic distance to the closest relative on the father's side and the mother's side, respectively, having haplotype A, excluding all descendants of the parents. If no such relative could be found, the number was set to 10,000. Then the father origin score of A was defined as $$F(P,T,A) = (1-2^{-m(P,T,A)})/(1-2^{-f(P,T,A)}).$$

M(P,T,A) was defined in a corresponding way. Note that M(P,T,A)=1/F(P,T,A).

For every pair of overlapping tiles, the LRP phasing results for a proband P were stitched together if the two overlapping haplotype pairs were compatible in one way but not the other. In this way stretches of overlapping tiles were merged together into contigs for each proband.

For each contig formed in this way, say for proband P and consisting of the tiles $T_1, \ldots, T_n$ with compatible haplotypes $A=(A_1, \ldots, A_n)$ on one hand and $B=(B_1, \ldots, B_n)$ on the other hand (one on each strand), the parental origin orientation score was defined as the product $$[F(P,T_1,A_1)* \ldots *F(P,T_n,A_n)]*[M(P,T_2,B_1)* \ldots *M(P,T_n,B_n)]$$

If this was >1, A was assigned to the father and B to the mother and vice versa if the result was <1.

One advantage of this method is that it does not require genotype information from the parents of a proband, since an extensive genealogy is available.

Assessing Genetic Risk

In the present context, and individual who is at an increased susceptibility (i.e., increased risk) for a disease, is an individual in whom at least one specific allele at one or more polymorphic marker or haplotype conferring increased susceptibility (increased risk) for the disease is identified (i.e., at-risk marker alleles or haplotypes). In certain embodiments, determination of the parental origin of the at-risk allele is performed to establish risk. The at-risk marker or haplotype is one that confers an increased risk (increased susceptibility) of the disease. In one embodiment, significance associated with a marker or haplotype is measured by a relative risk (RR). In another embodiment, significance associated with a marker or haplotye is measured by an odds ratio (OR). In a further embodiment, the significance is measured by a percentage. In one embodiment, a significant increased risk is measured as a risk (relative risk and/or odds ratio) of at least 1.1, including but not limited to: at least 1.2, at least 1.3, at least 1.4, at least 1.5, at least 1.6, at least 1.7, at least 1.8, at least 1.9, at least 2.0, at least 2.5, at least 3.0, at least 4.0, and at least 5.0. In a particular embodiment, a risk (relative risk and/or odds ratio) of at least 1.2 is significant. In another particular embodiment, a risk of at least 1.3 is significant. In yet another embodiment, a risk of at least 1.4 is significant. In a further embodiment, a relative risk of at least 1.5 is significant. In another further embodiment, a significant increase in risk is at least 1.7 is significant. However, other cutoffs are also contemplated, e.g., at least 1.15, 1.25, 1.35, and so on, and such cutoffs are also within scope of the present invention. In other embodiments, a significant increase in risk is at least about 20%, including but not limited to about 25%, 30%, 35%, 40%, 45%, 50%, 55%, 60%, 65%, 70%, 75%, 80%, 85%, 90%, 95%, 100%, 150%, 200%, 300%, and 500%. In one particular embodiment, a significant increase in risk is at least 20%. In other embodiments, a significant increase in risk is at least 30%, at least 40%, at least 50%, at least 60%, at least 70%, at least 80%, at least 90% and at least 100%. Other cutoffs or ranges as deemed suitable by the person skilled in the art to characterize the invention are however also contemplated, and those are also within scope of the present invention. In certain embodiments, a significant increase in risk is characterized by a p-value, such as a p-value of less than 0.05, less than 0.01, less than 0.001, less than 0.0001, less than 0.00001, less than 0.000001, less than 0.0000001, less than 0.00000001, or less than 0.000000001.

An at-risk polymorphic marker or haplotype as described herein is one where at least one allele of at least one marker or haplotype is more frequently present in an individual at risk for the disease (or trait) (affected), or diagnosed with the disease, compared to the frequency of its presence in a comparison group (control), such that the presence of the marker or haplotype is indicative of susceptibility to the disease. In certain embodiments, alleles or haplotypes with a particular parental origin are present more frequently in individuals at risk for the disease (affecteds) than controls. The control group may in one embodiment be a population sample, i.e. a random sample from the general population. In another embodiment, the control group is represented by a group of individuals who are disease-free. Such disease-free controls may in one embodiment be characterized by the absence of one or more specific disease-associated symptoms. Alternatively, the disease-free controls are those that have not been diagnosed with the disease. In another embodiment, the disease-free control group is characterized by the absence of one or more disease-specific risk factors. Such risk factors are in one embodiment at least one environmental risk factor. Representative environmental factors are natural products, minerals or other chemicals which are known to affect, or contemplated to affect, the risk of developing the specific disease or trait. Other environmental risk factors are risk factors related to lifestyle, including but not limited to food and drink habits, geographical location of main habitat, and occupational risk factors. In another embodiment, the risk factors comprise at least one additional genetic risk factor.

As an example of a simple test for correlation would be a Fisher-exact test on a two by two table. Given a cohort of chromosomes, the two by two table is constructed out of the number of chromosomes that include both of the markers or haplotypes, one of the markers or haplotypes but not the other and neither of the markers or haplotypes. Other statistical tests of association known to the skilled person are also contemplated and are also within scope of the invention.

In other embodiments of the invention, an individual who is at a decreased susceptibility (i.e., at a decreased risk) for a disease is an individual in whom at least one specific allele at one or more polymorphic marker or haplotype conferring decreased susceptibility for the disease is identified. The marker alleles and/or haplotypes conferring decreased risk are also said to be protective. In one aspect, the protective marker or haplotype is one that confers a significant decreased risk (or susceptibility) of the disease or trait. In one embodiment, significant decreased risk is measured as a relative risk (or odds ratio) of less than 0.9, including but not limited to less than 0.9, less than 0.8, less than 0.7, less than 0.6, less than 0.5, less than 0.4, less than 0.3, less than 0.2 and less than 0.1. In one particular embodiment, significant decreased risk is less than 0.7. In another embodiment, significant decreased risk is less than 0.5. In yet another embodiment, significant decreased risk is less than 0.3. In another embodiment, the decrease in risk (or susceptibility) is at least 20%, including but not limited to at least 25%, at least 30%, at least 35%, at least 40%, at least 45%, at least 50%, at least 55%, at least 60%, at least 65%, at least 70%, at least 75%, at least 80%, at least 85%, at least 90%, at least 95% and at least 98%. In one particular embodiment, a significant decrease in risk is at least about 30%. In another embodiment, a significant decrease in risk is at least about 50%. In another embodiment, the decrease in risk is at least about 70%. Other cutoffs or ranges as deemed suitable by the person skilled in the art to characterize the invention are however also contemplated, and those are also within scope of the present invention.

The person skilled in the art will appreciate that for markers with two alleles present in the population being studied (such as SNPs), and wherein one allele is found in increased frequency in a group of individuals with a trait or disease in the population, compared with controls, the other allele of the marker will be found in decreased frequency in the group of individuals with the trait or disease, compared with controls. In such a case, one allele of the marker (the one found in increased frequency in individuals with the trait or disease) will be the at-risk allele, while the other allele will be a protective allele.

A genetic variant associated with a disease or a trait can be used alone to predict the risk of the disease for a given genotype. For a biallelic marker, such as a SNP, there are 3 possible genotypes: homozygote for the at risk variant, heterozygote, and non carrier of the at risk variant. Risk associated with variants at multiple loci can be used to estimate overall risk. For multiple SNP variants, there are k possible genotypes $k=3^n \times 2^p$; where n is the number autosomal loci and p the number of gonosomal (sex chromosomal) loci. Overall risk assessment calculations for a plurality of risk variants usually assume that the relative risks of different genetic variants multiply, i.e. the overall risk (e.g., RR or OR) associated with a particular genotype combination is the product of the risk values for the genotype at each locus. If the risk presented is the relative risk for a person, or a specific genotype for a person, compared to a reference population with matched gender and ethnicity, then the combined risk—is the product of the locus specific risk values—and which also corresponds to an overall risk estimate compared with the population. If the risk for a person is based on a comparison to non-carriers of the at risk allele, then the combined risk corresponds to an estimate that compares the person with a given combination of genotypes at all loci to a group of individuals who do not carry risk variants at any of those loci. The group of non-carriers of any at risk variant has the lowest estimated risk and has a combined risk, compared with itself (i.e., non-carriers) of 1.0, but has an overall risk, compare with the population, of less than 1.0. It should be noted that the group of non-carriers can potentially be very small, especially for large number of loci, and in that case, its relevance is correspondingly small.

The multiplicative model is a parsimonious model that usually fits the data of complex traits reasonably well. Deviations from multiplicity have been rarely described in the context of common variants for common diseases, and if reported are usually only suggestive since very large sample sizes are usually required to be able to demonstrate statistical interactions between loci.

By way of an example, let us consider the case where a total of eight variants have been described to associate with a disease. One such example is provided by prostate cancer (Gudmundsson, J., et al., *Nat Genet.* 39:631-7 (2007), Gudmundsson, J., et al., *Nat Genet.* 39:977-83 (2007); Yeager, M., et al, *Nat Genet.* 39:645-49 (2007), Amundadottir, L., et al., *Nat Genet.* 38:652-8 (2006); Haiman, C. A., et al., *Nat Genet.* 39:638-44 (2007)). Seven of these loci are on autosomes, and the remaining locus is on chromosome X. The total number of theoretical genotypic combinations is then $3^7 \times 2^1 = 4374$. Some of those genotypic classes are very rare, but are still possible, and should be considered for overall risk assessment. It is likely that the multiplicative model applied in the case of multiple genetic variant will also be valid in conjugation with non-genetic risk variants assuming that the genetic variant does not clearly correlate with the "environmental" factor. In other words, genetic and non-genetic at-risk variants can be assessed under the multiplicative model to estimate combined risk, assuming that the non-genetic and genetic risk factors do not interact.

Using the same quantitative approach, the combined or overall risk associated with a plurality of variants associated with type 2 diabetes may be assessed. For example, a number of genetic variants have been identified as associated with risk of type 2 diabetes, (Frayling *Nature Reviews Genetics* 8:657-662 (2007); Zeggini, E. et al. *Science* 316:1336-1341 (2007); Diabetes Genetic Initiative (DGI) of Broad Institute of Harvard and MIT, Lund University and Novartis Institute for Biomedical Research, Science 316:1331-1336 (2007); Scott L J, et al. *Science* 316:1341-1345 (2007)), including rs1801282 (in the PPARG gene), rs5215 (KCNJ11), rs7901695 and rs7903146 (in TCF7L2), rs7756992 (CDKAL1), rs4430796 (TCF2), rs10010131 (WFS1), rs1111875 (HHEX-IDE), rs13266634 (SLC30A8), rs10946398 (CDKAL1), rs10811661 (CDKN2A-CDKN28), rs4402960 and rs1470589 (IGF28P2), rs8050136 (FTO), rs864745 (JAZF1), rs12779790 (CDC123-CAMK1D), rs7961581 (TSPAN8-LGR5), rs7578597 (THADA), rs4607103 (ADAMTS9), rs10923931 (NTCH2-ADAM30), and rs9300039. Any one, or a combination of, these markers, or surrogate markers in linkage disequilibrium therewith, can be used in combination with the markers disclosed herein for risk assessment of type 2 diabetes, and such combinations are all contemplated and within scope of the present invention.

Linkage Disequilibrium

The natural phenomenon of recombination, which occurs on average once for each chromosomal pair during each meiotic event, represents one way in which nature provides variations in sequence (and biological function by consequence). It has been discovered that recombination does not occur randomly in the genome; rather, there are large variations in the frequency of recombination rates, resulting in small regions of high recombination frequency (also called recombination hotspots) and larger regions of low recombination frequency, which are commonly referred to as Linkage Disequilibrium (LD) blocks (Myers, S. et al., *Biochem Soc Trans* 34:526-530 (2006); Jeffreys, A. J., et al., *Nature Genet.* 29:217-222 (2001); May, C. A., et al., *Nature Genet.* 31:272-275 (2002)).

Linkage Disequilibrium (LD) refers to a non-random assortment of two genetic elements. For example, if a particular genetic element (e.g., an allele of a polymorphic marker, or a haplotype) occurs in a population at a frequency of 0.50 (50%) and another element occurs at a frequency of 0.50 (50%), then the predicted occurrance of a person's having both elements is 0.25 (25%), assuming a random distribution of the elements. However, if it is discovered that the two elements occur together at a frequency higher than 0.25, then the elements are said to be in linkage disequilibrium, since they tend to be inherited together at a higher rate than what their independent frequencies of occurrence (e.g., allele or haplotype frequencies) would predict. Roughly speaking, LD is generally correlated with the frequency of recombination events between the two elements. Allele or haplotype frequencies can be determined in a population by genotyping individuals in a population and determining the frequency of the occurrence of each allele or haplotype in the population. For populations of diploids, e.g., human populations, individuals will typically have two alleles or allelic combinations for each genetic element (e.g., a marker, haplotype or gene).

Many different measures have been proposed for assessing the strength of linkage disequilibrium (LD; reviewed in Devlin, B. & Risch, N., *Genomics* 29:311-22 (1995))). Most capture the strength of association between pairs of biallelic sites. Two important pairwise measures of LD are $r^2$ (sometimes denoted $\Delta^2$) and |D'| (Lewontin, R., *Genetics* 49:49-67 (1964); Hill, W. G. & Robertson, A. *Theor. Appl. Genet.* 22:226-231 (1968)). Both measures range from 0 (no disequilibrium) to 1 ('complete' disequilibrium), but their interpretation is slightly different. |D'| is defined in such a way that it is equal to 1 if just two or three of the possible haplotypes are present, and it is <1 if all four possible haplotypes are present. Therefore, a value of |D'| that is <1 indicates that historical recombination may have occurred between two sites (recurrent mutation can also cause |D'| to be <1, but for single nucleotide polymorphisms (SNPs) this is usually regarded as being less likely than recombination). The measure $r^2$ represents the statistical correlation between two sites, and takes the value of 1 if only two haplotypes are present.

The $r^2$ measure is arguably the most relevant measure for association mapping, because there is a simple inverse relationship between $r^2$ and the sample size required to detect association between susceptibility loci and SNPs. These measures are defined for pairs of sites, but for some applications a determination of how strong LD is across an entire region that contains many polymorphic sites might be desirable (e.g., testing whether the strength of LD differs significantly among loci or across populations, or whether there is more or less LD in a region than predicted under a particular model). Measuring LD across a region is not straightforward, but one approach is to use the measure r, which was developed in population genetics. Roughly speaking, r measures how much recombination would be required under a particular population model to generate the LD that is seen in the data. This type of method can potentially also provide a statistically rigorous approach to the problem of determining whether LD data provide evidence for the presence of recombination hotspots. For the methods described herein, a significant $r^2$ value can be at least 0.1 such as at least 0.1, 0.15, 0.2, 0.25, 0.3, 0.35, 0.4, 0.45, 0.5, 0.55, 0.6, 0.65, 0.7, 0.75, 0.8, 0.85, 0.9, 0.91, 0.92, 0.93, 0.94, 0.95, 0.96, 0.97, 0.98, or at least 0.99. In one preferred embodiment, the significant $r^2$ value can be at least 0.2. Alternatively, linkage disequilibrium as described herein, refers to linkage disequilibrium characterized by values of |D'| of at least 0.2, such as 0.3, 0.4, 0.5, 0.6, 0.7, 0.8, 0.85, 0.9, 0.95, 0.96, 0.97, 0.98, or at least 0.99. Thus, linkage disequilibrium represents a correlation between alleles of distinct markers. It is measured by correlation coefficient or |D'| ($r^2$ up to 1.0 and |D'| up to 1.0). In certain embodiments, linkage disequilibrium is defined in terms of values for both the $r^2$ and |D'| measures. In one such embodiment, a significant linkage disequilibrium is defined as $r^2 > 0.1$ and |D'| > 0.8. In another embodiment, a significant linkage disequilibrium is defined as $r^2 > 0.2$ and |D'| > 0.9. Other combinations and permutations of values of $r^2$ and |D'| for determining linkage disequilibrium are also contemplated, and are also within the scope of the invention. Linkage disequilibrium can be determined in a single human population, as defined herein, or it can be determined in a collection of samples comprising individuals from more than one human population. In one embodiment of the invention, LD is determined in a sample from one or more of the HapMap populations (caucasian, african, japanese, chinese), as defined (http://www.hapmap.org). In one such embodiment, LD is determined in the CEU population of the HapMap samples. In another embodiment, LD is determined in the YRI population. In yet another embodiment, LD is determined in samples from the Icelandic population.

If all polymorphisms in the genome were independent at the population level (i.e., no LD), then every single one of them would need to be investigated in association studies, to assess all the different polymorphic states. However, due to linkage disequilibrium between polymorphisms, tightly linked polymorphisms are strongly correlated, which reduces the number of polymorphisms that need to be investigated in an association study to observe a significant association. Another consequence of LD is that many polymorphisms may give an association signal due to the fact that these polymorphisms are strongly correlated.

Genomic LD maps have been generated across the genome, and such LD maps have been proposed to serve as framework for mapping disease-genes (Risch, N. & Merkiangas, K, Science 273:1516-1517 (1996); Maniatis, N., et al., Proc Natl Acad Sci USA 99:2228-2233 (2002); Reich, D E et al, Nature 411:199-204 (2001)).

It is now established that many portions of the human genome can be broken into series of discrete haplotype blocks containing a few common haplotypes; for these blocks, linkage disequilibrium data provides little evidence indicating recombination (see, e.g., Wall., J. D. and Pritchard, J. K., Nature Reviews Genetics 4:587-597 (2003); Daly, M. et al., Nature Genet. 29:229-232 (2001); Gabriel, S. B. et al., Science 296:2225-2229 (2002); Patil, N. et al., Science 294: 1719-1723 (2001); Dawson, E. et al., Nature 418:544-548 (2002); Phillips, M. S. et al., Nature Genet. 33:382-387 (2003)).

There are two main methods for defining these haplotype blocks: blocks can be defined as regions of DNA that have limited haplotype diversity (see, e.g., Daly, M. et al., Nature Genet. 29:229-232 (2001); Patil, N. et al., Science 294:1719-1723 (2001); Dawson, E. et al., Nature 418:544-548 (2002); Zhang, K. et al., Proc. Natl. Acad. Sci. USA 99:7335-7339 (2002)), or as regions between transition zones having extensive historical recombination, identified using linkage disequilibrium (see, e.g., Gabriel, S. B. et al., Science 296:2225-2229 (2002); Phillips, M. S. et al., Nature Genet. 33:382-387 (2003); Wang, N. et al., Am. J. Hum. Genet. 71:1227-1234 (2002); Stumpf, M. P., and Goldstein, D. B., Curr. Biol. 13:1-8 (2003)). More recently, a fine-scale map of recombination rates and corresponding hotspots across the human genome has been generated (Myers, S., et al., Science 310: 321-32324 (2005); Myers, S. et al., Biochem Soc Trans 34:526530 (2006)). The map reveals the enormous variation in recombination across the genome, with recombination rates as high as 10-60 cM/Mb in hotspots, while closer to 0 in intervening regions, which thus represent regions of limited haplotype diversity and high LD. The map can therefore be used to define haplotype blocks/LD blocks as regions flanked by recombination hotspots. As used herein, the terms "haplotype block" or "LD block" includes blocks defined by any of the above described characteristics, or other alternative methods used by the person skilled in the art to define such regions.

Haplotype blocks (LD blocks) can be used to map associations between phenotype and haplotype status, using single markers or haplotypes comprising a plurality of markers. The main haplotypes can be identified in each haplotype block, and then a set of "tagging" SNPs or markers (the smallest set of SNPs or markers needed to distinguish among the haplotypes) can then be identified. These tagging SNPs or markers can then be used in assessment of samples from groups of individuals, in order to identify association between phenotype and haplotype. If desired, neighboring haplotype blocks can be assessed concurrently, as there may also exist linkage disequilibrium among the haplotype blocks.

It has thus become apparent that for any given observed association to a polymorphic marker in the genome, it is likely that additional markers in the genome also show association. This is a natural consequence of the uneven distribution of LD across the genome, as observed by the large variation in recombination rates. The markers used to detect association thus in a sense represent "tags" for a genomic region (i.e., a haplotype block or LD block) that is associating with a given disease or trait, and as such are useful for use in the methods and kits of the present invention. One or more causative (functional) variants or mutations may reside within the region found to be associating to the disease or trait. The functional variant may be another SNP, a tandem repeat polymorphism (such as a minisatellite or a microsatellite), a transposable element, or a copy number variation, such as an inversion, deletion or insertion. Such variants in LD with the variants described herein may confer a higher relative risk (RR) or odds ratio (OR) than observed for the tagging markers used to detect the association. The present invention thus refers to the markers used for detecting association to the disease, as described herein, as well as markers in linkage disequilibrium with the markers. Thus, in certain embodiments of the invention, markers that are in LD with the markers and/or haplotypes of the invention, as described herein, may be used as surrogate markers. The surrogate markers have in one embodiment relative risk (RR) and/or odds ratio (OR) values smaller than for the markers or haplotypes initially found to be associating with the disease, as described herein. In other embodiments, the surrogate markers have RR or OR values greater than those initially determined for the markers initially found to be associating with the disease, as described herein. An example of such an embodiment would be a rare, or relatively rare (such as <10% allelic population frequency) variant in LD with a more common variant (>10% population frequency) initially found to be associating with the disease, such as the variants described herein. Identifying and using such markers for detecting the association discovered by the inventors as described herein can be performed by routine methods well known to the person skilled in the art, and are therefore within the scope of the present invention.

Determination of Haplotype Frequency

The frequencies of haplotypes in patient and control groups can be estimated using an expectation-maximization algorithm (Dempster A. et al., *J. R. Stat. Soc. B*, 39:1-38 (1977)). An implementation of this algorithm that can handle missing genotypes and uncertainty with the phase can be used. Under the null hypothesis, the patients and the controls are assumed to have identical frequencies. Using a likelihood approach, an alternative hypothesis is tested, where a candidate at-risk-haplotype, which can include the markers described herein, is allowed to have a higher frequency in patients than controls, while the ratios of the frequencies of other haplotypes are assumed to be the same in both groups. Likelihoods are maximized separately under both hypotheses and a corresponding 1-df likelihood ratio statistic is used to evaluate the statistical significance.

To look for at-risk and protective markers and haplotypes within a susceptibility region, for example within an LD block, association of all possible combinations of genotyped markers within the region is studied. The combined patient and control groups can be randomly divided into two sets, equal in size to the original group of patients and controls. The marker and haplotype analysis is then repeated and the most significant p-value registered is determined. This randomization scheme can be repeated, for example, over 100 times to construct an empirical distribution of p-values. In a preferred embodiment, a p-value of <0.05 is indicative of a significant marker and/or haplotype association.

Haplotype Analysis

One general approach to haplotype analysis involves using likelihood-based inference applied to NEsted MOdels (Gretarsdottir S., et al., *Nat. Genet.* 35:131-38 (2003)). The method is implemented in the program NEMO, which allows for many polymorphic markers, SNPs and microsatellites. The method and software are specifically designed for case-control studies where the purpose is to identify haplotype groups that confer different risks. It is also a tool for studying LD structures. In NEMO, maximum likelihood estimates, likelihood ratios and p-values are calculated directly, with the aid of the EM algorithm, for the observed data treating it as a missing-data problem.

Even though likelihood ratio tests based on likelihoods computed directly for the observed data, which have captured the information loss due to uncertainty in phase and missing genotypes, can be relied on to give valid p-values, it would still be of interest to know how much information had been lost due to the information being incomplete. The information measure for haplotype analysis is described in Nicolae and Kong (Technical Report 537, Department of Statistics, University of Statistics, University of Chicago; *Biometrics*, 60(2):368-75 (2004)) as a natural extension of information measures defined for linkage analysis, and is implemented in NEMO.

For single marker association to a disease, the Fisher exact test can be used to calculate two-sided p-values for each individual allele. Usually, all p-values are presented unadjusted for multiple comparisons unless specifically indicated. The presented frequencies (for microsatellites, SNPs and haplotypes) are allelic frequencies as opposed to carrier frequencies. To minimize any bias due the relatedness of the patients who were recruited as families to the study, first and second-degree relatives can be eliminated from the patient list. Furthermore, the test can be repeated for association correcting for any remaining relatedness among the patients, by extending a variance adjustment procedure previously described (Risch, N. & Teng, J. *Genome Res.*, 8:1273-1288 (1998)) for sibships so that it can be applied to general familial relationships, and present both adjusted and unadjusted p-values for comparison. The method of genomic controls (Devlin, B. & Roeder, K. *Biometrics* 55:997 (1999)) can also be used to adjust for the relatedness of the individuals and possible stratification. The differences are in general very small as expected. To assess the significance of single-marker association corrected for multiple testing we can carry out a randomization test using the same genotype data. Cohorts of patients and controls can be randomized and the association analysis redone multiple times (e.g., up to 500,000 times) and the p-value is the fraction of replications that produced a p-value for some marker allele that is lower than or equal to the p-value we observed using the original patient and control cohorts.

For both single-marker and haplotype analyses, relative risk (RR) and the population attributable risk (PAR) can be calculated assuming a multiplicative model (haplotype relative risk model) (Terwilliger, J. D. & Ott, J., *Hum. Hered.* 42:337-46 (1992) and Falk, C. T. & Rubinstein, P, *Ann. Hum. Genet.* 51 (Pt 3):227-33 (1987)), i.e., that the risks of the two alleles/haplotypes a person carries multiply. For example, if RR is the risk of A relative to a, then the risk of a person homozygote AA will be RR times that of a heterozygote Aa and $RR^2$ times that of a homozygote aa. The multiplicative model has a nice property that simplifies analysis and computations—haplotypes are independent, i.e., in Hardy-Weinberg equilibrium, within the affected population as well as within the control population. As a consequence, haplotype counts of the affecteds and controls each have multinomial distributions, but with different haplotype frequencies under the alternative hypothesis. Specifically, for two haplotypes, $h_i$ and $h_j$, $risk(h_i)/risk(h_j)=(f_i/p_i)/(f_j/p_j)$, where f and p denote, respectively, frequencies in the affected population and in the control population. While there is some power loss if the true model is not multiplicative, the loss tends to be mild except for extreme cases. Most importantly, p-values are always valid since they are computed with respect to null hypothesis.

An association signal detected in one association study may be replicated in a second cohort, ideally from a different population (e.g., different region of same country, or a different country) of the same or different ethnicity. The advantage of replication studies is that the number of tests performed in the replication study is usually quite small, and hence the less stringent the statistical measure that needs to be applied. For example, for a genome-wide search for susceptibility variants for a particular disease or trait using 300,000 SNPs, a correction for the 300,000 tests performed (one for each SNP) can be performed. Since many SNPs on the arrays typically used are correlated (i.e., in LD), they are not independent. Thus, the correction is conservative. Nevertheless, applying this correction factor requires an observed P-value of less than $0.05/300,000=1.7 \times 10^{-7}$ for the signal to be considered significant applying this conservative test on results from a single study cohort. Obviously, signals found in a genome-wide association study with P-values less than this conservative threshold are a measure of a true genetic effect, and replication in additional cohorts is not necessarily from a statistical point of view. Importantly, however, signals with P-values that are greater than this threshold may also be due to a true genetic effect. Thus, since the correction factor depends on the number of statistical tests performed, if one signal (one SNP) from an initial study is replicated in a second case-control cohort, the appropriate statistical test for significance is that for a single statistical test, i.e., P-value less than 0.05. Replication studies in one or even several additional case-control cohorts have the added advantage of providing assessment of the association signal in additional populations, thus simultaneously confirming the initial finding and providing an assessment of the overall significance of the genetic variant(s) being tested in human populations in general.

The results from several case-control cohorts can also be combined to provide an overall assessment of the underlying effect. The methodology commonly used to combine results from multiple genetic association studies is the Mantel-Haenszel model (Mantel and Haenszel, *J Nat/Cancer Inst* 22:719-48 (1959)). The model is designed to deal with the situation where association results from different populations, with each possibly having a different population frequency of the genetic variant, are combined. The model combines the results assuming that the effect of the variant on the risk of the disease, a measured by the OR or RR, is the same in all populations, while the frequency of the variant may differ between the populations. Combining the results from several populations has the added advantage that the overall power to detect a real underlying association signal is increased, due to the increased statistical power provided by the combined cohorts. Furthermore, any deficiencies in individual studies, for example due to unequal matching of cases and controls or population stratification will tend to balance out when results from multiple cohorts are combined, again providing a better estimate of the true underlying genetic effect.

Risk Assessment and Diagnostics

Within any given population, there is an absolute risk of developing a disease or trait, defined as the chance of a person developing the specific disease or trait over a specified time-period. For example, a woman's lifetime absolute risk of breast cancer is one in nine. That is to say, one woman in every nine will develop breast cancer at some point in their lives. Risk is typically measured by looking at very large numbers of people, rather than at a particular individual. Risk is often presented in terms of Absolute Risk (AR) and Relative Risk (RR). Relative Risk is used to compare risks associating with two variants or the risks of two different groups of people. For example, it can be used to compare a group of people with a certain genotype with another group having a different genotype. For a disease, a relative risk of 2 means that one group has twice the chance of developing a disease as the other group. The risk presented is usually the relative risk for a person, or a specific genotype of a person, compared to the population with matched gender and ethnicity. Risks of two individuals of the same gender and ethnicity could be compared in a simple manner. For example, if, compared to the population, the first individual has relative risk 1.5 and the second has relative risk 0.5, then the risk of the first individual compared to the second individual is 1.5/0.5=3.

As described herein, certain polymorphic markers and haplotypes comprising such markers are found to be useful for risk assessment of certain disease conditions (type 2 diabetes, breast cancer, basal cell carcinoma). Risk assessment can involve the use of the markers for determining disease susceptibility. Particular alleles of polymorphic markers (e.g., SNP5) are found more frequently in individuals with a particular disease, than in individuals without diagnosis of the disease. In particular, risk alleles of such markers with a particular parental origin are found to confer risk of the disease. Therefore, these marker alleles have predictive value for detecting a susceptibility to the disease in an individual. Tagging markers in linkage disequilibrium with at-risk variants (or protective variants) described herein can be used as surrogates for these markers (and/or haplotypes). Such surrogate markers can be located within a particular haplotype block or LD block. Such surrogate markers can also sometimes be located outside the physical boundaries of such a haplotype block or LD block, either in close vicinity of the LD block/haplotype block, but possibly also located in a more distant genomic location.

Long-distance LD can for example arise if particular genomic regions (e.g., genes) are in a functional relationship. For example, if two genes encode proteins that play a role in a shared metabolic pathway, then particular variants in one gene may have a direct impact on observed variants for the other gene. Let us consider the case where a variant in one gene leads to increased expression of the gene product. To counteract this effect and preserve overall flux of the particular pathway, this variant may have led to selection of one (or more) variants at a second gene that conferes decreased expression levels of that gene. These two genes may be located in different genomic locations, possibly on different chromosomes, but variants within the genes are in apparent LD, not because of their shared physical location within a region of high LD, but rather due to evolutionary forces. Such LD is also contemplated and within scope of the present invention. The skilled person will appreciate that many other scenarios of functional gene-gene interaction are possible, and the particular example discussed here represents only one such possible scenario.

Markers with values of $r^2$ equal to 1 are perfect surrogates for the at-risk variants, i.e. genotypes for one marker perfectly predicts genotypes for the other. Markers with smaller values of $r^2$ than 1 can also be surrogates for the at-risk variant, or alternatively represent variants with relative risk values as high as or possibly even higher than the at-risk variant. The at-risk variant identified may not be the functional variant itself, but is in this instance in linkage disequilibrium with the true functional variant. The functional variant may for example be a tandem repeat, such as a minisatellite or a microsatellite, a transposable element (e.g., an Alu element), or a structural alteration, such as a deletion, insertion or inversion (sometimes also called copy number variations, or CNVs). The present invention encompasses the assessment of such surrogate markers for the markers as disclosed herein. Such markers are annotated, mapped and listed in public databases, as well known to the skilled person, or can alternatively be readily identified by sequencing the region or a part of the region identified by the markers of the present invention in a group of individuals, and identify polymorphisms in the resulting group of sequences. As a consequence, the person skilled in the art can readily and without undue experimentation identify and genotype surrogate markers in linkage disequilibrium with the markers and/or haplotypes as described herein. The tagging or surrogate markers in LD with the at-risk variants detected, also have predictive value for detecting association to the disease, or a susceptibility to the disease, in an individual. These tagging or surrogate markers that are in LD with the markers of the present invention can also include other markers that distinguish among haplotypes, as these similarly have predictive value for detecting susceptibility to the particular disease.

The present invention can in certain embodiments be practiced by assessing a sample comprising genomic DNA from an individual for the presence of disease-associated variants. Such assessment typically steps that of obtaining sequence data to detect the presence or absence of at least one allele of at least one polymorphic marker, using methods well known to the skilled person and further described herein, and based on the outcome of such assessment, determine whether the individual from whom the sample is derived is at increased or decreased risk (increased or decreased susceptibility) of the particular disease condition. Detecting particular alleles of polymorphic markers can in certain embodiments be done by obtaining nucleic acid sequence data about a particular human individual, that identifies at least one allele of at least one polymorphic marker. Different alleles of the at least one marker are associated with different susceptibility to the disease in humans. Obtaining nucleic acid sequence data can comprise nucleic acid sequence at a single nucleotide position, which is sufficient to identify alleles at SNPs. The nucleic acid sequence data can also comprise sequence at any other number of nucleotide positions, in particular for genetic markers that comprise multiple nucleotide positions, and can be anywhere from two to hundreds of thousands, possibly even millions, of nucleotides (in particular, in the case of copy number variations (CNVs)).

In certain embodiments, the invention can be practiced utilizing a dataset comprising information about the genotype status of at least one polymorphic marker associated with a disease (or markers in linkage disequilibrium with at least one marker associated with the disease), optionally also including information about the parental origin of particular alleles of the marker. In other words, a dataset containing information about such genetic status, for example in the form of genotype counts at a certain polymorphic marker, or a plurality of markers (e.g., an indication of the presence or absence of certain at-risk alleles), or actual genotypes for one or more markers, can be queried for the presence or absence of certain at-risk alleles at certain polymorphic markers shown by the present inventors to be associated with the disease. In certain embodiments, a query for alleles with a particular parental origin is made. A positive result for a variant (e.g., marker allele) associated with the disease, or a variant with a particular parental orgin, is indicative of the individual from which the dataset is derived is at increased susceptibility (increased risk) of the disease.

In certain embodiments of the invention, a polymorphic marker is correlated to a disease by referencing genotype data for the polymorphic marker to a look-up table that comprises correlations between at least one allele of the polymorphism and the disease. In some embodiments, the table comprises a correlation for one polymorphism. In other embodiments, the table comprises a correlation for a plurality of polymorphisms. In both scenarios, by referencing to a look-up table that gives an indication of a correlation between a marker and the disease, a risk for the disease, or a susceptibility to the disease, can be identified in the individual from whom the sample is derived. In some embodiments, the correlation is reported as a statistical measure. The statistical measure may be reported as a risk measure, such as a relative risk (RR), an absolute risk (AR) or an odds ratio (OR).

The markers described herein may be useful for risk assessment and diagnostic purposes, either alone or in combination. Results of disease risk based on the markers described herein can also be combined with data for other genetic markers or risk factors for type 2 diabetes, to establish overall risk. Thus, even in cases where the increase in risk by individual markers is relatively modest, e.g. on the order of 10-30%, the association may have significant implications. Thus, relatively common variants may have significant contribution to the overall risk (Population Attributable Risk is high), or combination of markers can be used to define groups of individual who, based on the combined risk of the markers, is at significant combined risk of developing the disease. In particular, a number of polymorphic markers have been found to be associated with risk of type 2 diabetes, for example as summarized in Frayling (*Nature Rev Genet.* 8:657-662 (2007)) and described further herein.

Thus, in certain embodiments of the invention, a plurality of variants (genetic markers, biomarkers and/or haplotypes) is used for overall risk assessment. These variants are in one embodiment selected from the variants as disclosed herein. Other embodiments include the use of the variants of the present invention in combination with other variants known to be useful for diagnosing a susceptibility to a particular disease (e.g., type 2 diabetes, breast cancer, basal cell carcinoma). In such embodiments, the genotype status of a plurality of markers and/or haplotypes is determined in an individual, and the status of the individual compared with the population frequency of the associated variants, or the frequency of the variants in clinically healthy subjects, such as age-matched and sex-matched subjects. Methods known in the art, such as multivariate analyses or joint risk analyses or other methods known to the skilled person, may subsequently be used to determine the overall risk conferred based on the genotype status at the multiple loci. Assessment of risk based on such analysis may subsequently be used in the methods, uses and kits of the invention, as described herein.

As described in the above, the haplotype block structure of the human genome has the effect that a large number of variants (markers and/or haplotypes) in linkage disequilibrium with the variant originally associated with a disease or trait may be used as surrogate markers for assessing association to the disease or trait. The number of such surrogate markers will depend on factors such as the historical recombination rate in the region, the mutational frequency in the region (i.e., the number of polymorphic sites or markers in the region), and the extent of LD (size of the LD block) in the region. These markers are usually located within the physical boundaries of the LD block or haplotype block in question as defined using the methods described herein, or by other methods known to the person skilled in the art. However, sometimes marker and haplotype association is found to extend beyond the physical boundaries of the haplotype block as defined, as discussed in the above. Such markers and/or haplotypes may in those cases be also used as surrogate markers and/or haplotypes for the markers and/or haplotypes physically residing within the haplotype block as defined. As a consequence, markers and haplotypes in LD (typically characterized by inter-marker $r^2$ values of greater than 0.1, such as $r^2$ greater than 0.2, including $r^2$ greater than 0.3, also including markers correlated by values for $r^2$ greater than 0.4) with the markers described herein are also within the scope of the invention, even if they are physically located beyond the boundaries of the haplotype block as defined.

In general, for markers with two possible alleles, such as most SNPs, the opposite allele to the allele found to be in excess in patients (at-risk allele) is found in decreased frequency in patients. Such marker alleles are thus protective for the disease, i.e. they confer a decreased risk or susceptibility of individuals carrying these markers will develop the disease. Markers with risk that is associated with a particular parental origin Study Population In a general sense, the methods and kits of the invention can be utilized from samples containing nucleic acid material (DNA or RNA) from any source and from any individual, or from genotype data derived from such samples. In preferred embodiments, the individual is a human individual. The individual can be an adult, child, or fetus. The nucleic acid source may be any sample comprising nucleic acid material, including biological samples, or a sample comprising nucleic acid material derived therefrom. The present invention also provides for assessing markers and/or haplotypes in individuals who are members of a target population. Such a target population is in one embodiment a population or group of individuals at risk of developing the disease, based on other genetic factors, biomarkers, biophysical parameters, or general health and/or lifestyle parameters (e.g., history of the disease, e.g., type 2 diabetes, breast cancer, basal cell carcinoma), previous diagnosis of the disease, family history of the disease).

The invention provides for embodiments that include individuals from specific age subgroups, such as those over the age of 40, over age of 45, or over age of 50, 55, 60, 65, 70, 75, 80, or 85. Other embodiments of the invention pertain to other age groups, such as individuals aged less than 85, such as less than age 80, less than age 75, or less than age 70, 65, 60, 55, 50, 45, 40, 35, or less than age 30. Other embodiments relate to individuals with age at onset of the disease condition (e.g., type 2 diabetes, breast cancer, basal cell carcinoma) in a particular age group, including age groups bracketed by any age as listed above. The invention furthermore relates to individuals of either gender, males or females.

The Icelandic population is a Caucasian population of Northern European ancestry. A large number of studies reporting results of genetic linkage and association in the Icelandic population have been published in the last few years. Many of those studies show replication of variants, originally identified in the Icelandic population as being associating with a particular disease, in other populations (Sulem, P., et al. *Nat Genet May* 17, 2009 (Epub ahead of print); Rafnar, T., et al. *Nat Genet.* 41:221-7 (2009); Gretarsdottir, S., et al. *Ann Neurol* 64:402-9 (2008); Stacey, S. N., et al. *Nat Genet.* 40:1313-18 (2008); Gudbjartsson, D. F., et al. *Nat Genet.* 40:886-91 (2008); Styrkarsdottir, U., et al. *N Engl J Med* 358:2355-65 (2008); Thorgeirsson, T., et al. *Nature* 452: 638-42 (2008); Gudmundsson, J., et al. *Nat. Genet.* 40:281-3 (2008); Stacey, S, N., et al., *Nat. Genet.* 39:865-69 (2007); Helgadottir, A., et al., *Science* 316:1491-93 (2007); Steinthorsdottir, V., et al., *Nat. Genet.* 39:770-75 (2007); Gudmundsson, J., et al., *Nat. Genet.* 39:631-37 (2007); Frayling, T M, *Nature Reviews Genet.* 8:657-662 (2007); Amundadottir, L. T., et al., *Nat. Genet.* 38:652-58 (2006); Grant, S. F., et al., *Nat. Genet.* 38:320-23 (2006)). Thus, genetic findings in the Icelandic population have in general been replicated in other populations, including populations from Africa and Asia. In particular, variants previously described as associated with risk of type 2 diabetes have been found to be associated with risk across many populations and ethnicities (Florez, J C, *Curr Opin Clin Nutr Metab Care* 10:391-396 (2007); Cauchi, S et al. *J Mol Med* 85:777-782 (2007); Frayling, T M *Nature Rev Genet.* 8:657-662 (2007), Zeggini, E. et al. *Science* 316:1336-1341 (2007); Diabetes Genetic Initiative (DGI) of Broad Institute of Harvard and MIT, Lund University and Novartis Institute for Biomedical Research, *Science* 316:1331-1336 (2007); Scott L J, et al. Science 316:1341-1345 (2007)), illustrating that the underlying disease association is applicable across different human populations.

It is thus believed that the markers of the present invention will show similar association in other human populations. Particular embodiments comprising individual human populations are thus also contemplated and within the scope of the invention. Such embodiments relate to human subjects that are from one or more human population including, but not limited to, Caucasian populations, European populations, American populations, Eurasian populations, Asian populations, Central/South Asian populations, East Asian populations, Middle Eastern populations, African populations, Hispanic populations, and Oceanian populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Czech, Greek and Turkish populations.

The racial contribution in individual subjects may also be determined by genetic analysis. Genetic analysis of ancestry may be carried out using unlinked microsatellite markers such as those set out in Smith et al. (*Am J Hum Genet.* 74, 1001-13 (2004)).

In certain embodiments, the invention relates to markers and/or haplotypes identified in specific populations, as described in the above. The person skilled in the art will appreciate that measures of linkage disequilibrium (LD) may give different results when applied to different populations. This is due to different population history of different human populations as well as differential selective pressures that may have led to differences in LD in specific genomic regions. It is also well known to the person skilled in the art that certain markers, e.g. SNP markers, have different population frequency in different populations, or are polymorphic in one population but not in another. The person skilled in the art will however apply the methods available and as thought herein to practice the present invention in any given human population. This may include assessment of polymorphic markers in the LD region of the present invention, so as to identify those markers that give strongest association within the specific population. Thus, the at-risk variants of the present invention may reside on different haplotype background and in different frequencies in various human populations. However, utilizing methods known in the art and the markers of the present invention, the invention can be practiced in any given human population.

Utility of Genetic Testing

The person skilled in the art will appreciate and understand that the variants described herein in general do not, by themselves, provide an absolute identification of individuals who will develop a particular disease condition, such as type 2 diabetes, breast cancer or basal cell carcinoma. The variants described herein are however useful for identifying those individuals who are at increased risk of developing the condition. This information is extremely valuable in itself, as outlined in more detail in the below, as it can be used to, for example, initiate preventive measures at an early stage, perform regular examinations to monitor the progress and/or appearance of symptoms, or to schedule exams at a regular interval to identify early symptoms, so as to be able to apply treatment at an early stage. In general terms, the knowledge about genetic variants that confers disease risk offers the opportunity to apply a genetic test to distinguish between individuals with increased risk of developing the disease (i.e. carriers of at-risk variants) and those with decreased risk of developing the disease (i.e. carriers of protective variants, or non-carries of at-risk variants). The core values of genetic testing, for individuals belonging to both of these groups, are the possibilities of being able to determine a predisposition to the condition at an early stage and provide information to the clinician about suscepbility, prognosis and/or aggressiveness of the disease in order to be able to apply the most appropriate treatment and/or preventive measure at an early stage.

The enormous public health burden of type 2 diabetes is largely due to the development of vascular complications, and vascular complications of type 1 diabetes severely reduce the quality of life of affected individuals. Overall, diabetes reduces life expectancy by 5-10 years, primarily due to these complications. The importance of genetic variants predisposing diabetes patients to these complications is therefore profound. Up to half of people with type 2 diabetes have vascular complications due to the disease at the time of diagnosis, and one fifth have retinopathy (Donnelly, R., et al., *British Med J* 320:1062-66 (2000)). Early detection of diabetes is therefore critical. In particular, the identification of individuals with increased risk of vascular complications of diabetes is important, since early identification facilitates earlier intervention, thus delaying and reducing the impact of the disease, and its vascular complications.

Cardiovascular disease risk can be reduced in patients with diabetes. While controlling hyperglycemia remains important, the identification and treatment of other CVD risk factors is also vital. Interventions that have been shown to decrease CVD events in diabetics include the treatment of hypertension and hyperlipidemia, aspirin therapy, use of ACE inhibitors, and smoking cessation. The United Kingdom Prospective Diabetes Study demonstrated that lowering blood pressure significantly reduces strokes, diabetes-related deaths, heart failure, and microvascular complications in patients with type 2 diabetes. Lipid management aimed at lowering LDL cholesterol, raising HDL cholesterol, and reducing triglycerides has been shown to decrease macrovascular disease and mortality in patients with type 2 diabetes, particularly those who have had prior cardiovascular events. The benefits of cholesterol lowering with statin medication in reducing CVD events also has been demonstrated in diabetic patients with average cholesterol levels and in individuals with impaired fasting glucose. ACE inhibitors have been shown to decrease cardiovascular events in type 2 diabetes patients with or without hypertension. Studies have documented the benefits of aspirin therapy and smoking cessation in reducing CVD.

Tight control of blood glucose and blood pressure are important treatments for kidney disease. Blood pressure has a dramatic effect on the rate at which the disease progresses. Even a mild rise in blood pressure can be harmful for the kidney. ACE inhibitors are recommended for most people with diabetes, high blood pressure, and kidney disease. Recent studies suggest that ACE inhibitors slow kidney disease in addition to lowering blood pressure and are helpful even in people who do not have high blood pressure. Accumulating evidence shows that diabetic vascular disease develops in individuals who are genetically susceptible and that hyperglycemia in itself is not sufficient to cause vascular complications. Since diabetic retinopathy is an unevitable and well known consequence of type 2 diabetes, with its devastating consequences, its detection at the very early stages is of utmost importance. Early intervention, through attention to glycaemic control together with other risk factors such as smoking and hypertension, may modify the further progress of this complication (Clarke, B. F., in *Type 2 diabetes in Children and Adolescents*, Kelnar, C. (ed); London, Chapman & Hall, pp 539-51 (1994)).

The discovery of genetic markers that predispose individuals to type 2 diabetes facilitates prospective identification of those individuals who are at greatest risk of developing this devastating disease. This information can then be used for risk stratification. Those individuals that have higher genetic risk of developing type 2 diabetes may be subjected to more stringent medical and lifestyle intervention as well as careful monitoring of other risk factors and more aggressive treatment, as failure to reach treatment target may be of much more drastic consequences for this part of the population.

Diagnostic and Screening Methods

In certain embodiments, the present invention pertains to methods of diagnosing, or aiding in the diagnosis of, particular disease conditions, including type 2 diabetes, breast cancer and basal cell carcinoma, or methods of determining a susceptibility to such conditions, by detecting particular alleles at genetic markers that appear more frequently in subjects diagnosed with these conditions. In certain embodiments, the invention provides methods that utilize determination of the parental origin of risk alleles, wherein a particular parental origin is associated with disease risk. Particular embodiments relate to the determination of a susceptibility to type 2 diabetes. The present invention describes methods whereby detection of particular alleles of particular markers or haplotypes is indicative of a susceptibility to type 2 diabetes. Such prognostic or predictive assays can also be used to determine prophylactic treatment of a subject prior to the onset of symptoms of type 2 diabetes.

The present invention pertains in some embodiments to methods of clinical applications of diagnosis, e.g., diagnosis performed by a medical professional. In other embodiments, the invention pertains to methods of diagnosis or determination of a susceptibility performed by a layman. The layman can be the customer of a genotyping service. The layman may also be a genotype service provider, who performs genotype analysis on a DNA sample from an individual, in order to provide service related to genetic risk factors for particular traits or diseases, based on the genotype status of the individual (i.e., the customer). Recent technological advances in genotyping technologies, including high-throughput genotyping of SNP markers, such as Molecular Inversion Probe array technology (e.g., Affymetrix GeneChip), and BeadArray Technologies (e.g., Illumina GoldenGate and Infinium assays) have made it possible for individuals to have their own genome assessed for up to one million SNPs simultaneously, at relatively little cost. The resulting genotype information, which can be made available to the individual, can be compared to information about disease or trait risk associated with various SNPs, including information from public literature and scientific publications. The diagnostic application of disease-associated alleles as described herein, can thus for example be performed by the individual, through analysis of his/her genotype data, by a health professional based on results of a clinical test, or by a third party, including the genotype service provider. The third party may also be service provider who interprets genotype information from the customer to provide service related to specific genetic risk factors, including the genetic markers described herein. In other words, the diagnosis or determination of a susceptibility of genetic risk can be made by health professionals, genetic counselors, third parties providing genotyping service, third parties providing risk assessment service or by the layman (e.g., the individual), based on information about the genotype status of an individual and knowledge about the risk conferred by particular genetic risk factors (e.g., particular SNPs). In the present context, the term "diagnosing", "diagnose a susceptibility" and "determine a susceptibility" is meant to refer to any available diagnostic method, including those mentioned above.

In certain embodiments, a sample containing genomic DNA from an individual is collected. Such sample can for example be a buccal swab, a saliva sample, a blood sample, or other suitable samples containing genomic DNA, as described further herein. The genomic DNA is then analyzed using any common technique available to the skilled person, such as high-throughput array technologies. Results from such genotyping are stored in a convenient data storage unit, such as a data carrier, including computer databases, data storage disks, or by other convenient data storage means. In certain embodiments, the computer database is an object database, a relational database or a post-relational database. The genotype data is subsequently analyzed for the presence of certain variants known to be susceptibility variants for a particular human conditions, such as the genetic variants described herein. Genotype data can be retrieved from the data storage unit using any convenient data query method. Calculating risk conferred by a particular genotype for the individual can be based on comparing the genotype of the individual to previously determined risk (expressed as a relative risk (RR) or and odds ratio (OR), for example) for the genotype, for example for a heterozygous carrier of an at-risk variant for a particular disease or trait (such as type 2 diabetes). The calculated risk for the individual can be the relative risk for a person, or for a specific genotype of a person, compared to the average population with matched gender and ethnicity. The average population risk can be expressed as a weighted average of the risks of different genotypes, using results from a reference population, and the appropriate calculations to calculate the risk of a genotype group relative to the population can then be performed. Alternatively, the risk for an individual is based on a comparison of particular genotypes, for example heterozygous carriers of an at-risk allele of a marker compared with non-carriers of the at-risk allele. Using the population average may in certain embodiments be more convenient, since it provides a measure which is easy to interpret for the user, i.e. a measure that gives the risk for the individual, based on his/her genotype, compared with the average in the population. The calculated risk estimated can be made available to the customer via a website, preferably a secure website.

In certain embodiments, a service provider will include in the provided service all of the steps of isolating genomic DNA from a sample provided by the customer, performing genotyping of the isolated DNA, calculating genetic risk based on the genotype data, and report the risk to the customer. In some other embodiments, the service provider will include in the service the interpretation of genotype data for the individual, i.e., risk estimates for particular genetic variants based on the genotype data for the individual. In some other embodiments, the service provider may include service that includes genotyping service and interpretation of the genotype data, starting from a sample of isolated DNA from the individual (the customer).

Overall risk for multiple risk variants can be performed using standard methodology. For example, assuming a multiplicative model, i.e. assuming that the risk of individual risk variants multiply to establish the overall effect, allows for a straight-forward calculation of the overall risk for multiple markers.

In addition, in certain other embodiments, the present invention pertains to methods of determining a decreased susceptibility to a disease, by detecting particular genetic marker alleles or haplotypes that appear less frequently in patients than in individuals not diagnosed with the disease or in the general population.

As described and exemplified herein, particular marker alleles are associated with risk of certain disease conditions, including type 2 diabetes, breast cancer and basal cell carcinoma. In one embodiment, the marker allele or haplotype is one that confers a significant risk or susceptibility to type 2 diabetes. In certain embodiments, a particular parental origin of the marker allele is the one that confers a risk of the disease condition. In certain embodiments, the significance of association of the at least one marker allele or haplotype is characterized by a p value<0.05. In other embodiments, the significance of association is characterized by smaller p-values, such as <0.01, <0.001, <0.0001, <0.00001, <0.000001, <0.0000001, <0.00000001 or <0.000000001.

In these embodiments, the presence of the at least one marker allele or haplotype is indicative of a susceptibility to the disease condition. Diagnostic methods involve determining whether particular alleles or haplotypes that are associated with the disease are present in the genomic sequence of particular individuals. In certain embodiments, the methods include a determination of whether the particular allele or haplotype originate from a particular parent (mother or father). The detection of the particular genetic marker alleles that make up particular haplotypes can be performed by a variety of methods described herein and/or known in the art. The marker alleles or haplotypes of the present invention correspond to fragments of genomic segments associated with a particular disease. Such fragments encompass the DNA sequence of the polymorphic marker or haplotype in question, but also include DNA segments in strong LD (linkage disequilibrium) with the marker or haplotype. In one embodiment, such segments comprises segments in LD with the marker or haplotype as determined by a value of $r^2$ greater than 0.2 and/or |D'|>0.8).

In one embodiment, determination of a susceptibility is accomplished using hybridization methods. (see Current Protocols in Molecular Biology, Ausubel, F. et al., eds., John Wiley & Sons, including all supplements). The presence of a specific marker allele can be indicated by sequence-specific hybridization of a nucleic acid probe specific for the particular allele. The presence of more than one specific marker allele or a specific haplotype can be indicated by using several sequence-specific nucleic acid probes, each being specific for a particular allele. A sequence-specific probe can be directed to hybridize to genomic DNA, RNA, or cDNA. A "nucleic acid probe", as used herein, can be a DNA probe or an RNA probe that hybridizes to a complementary sequence. One of skill in the art would know how to design such a probe so that sequence specific hybridization will occur only if a particular allele is present in a genomic sequence from a test sample. The invention can also be reduced to practice using any convenient genotyping method, including commercially available technologies and methods for genotyping particular polymorphic markers.

To determine a susceptibility to a hybridization sample can be formed by contacting the test sample, such as a genomic DNA sample, with at least one nucleic acid probe. A non-limiting example of a probe for detecting mRNA or genomic DNA is a labeled nucleic acid probe that is capable of hybridizing to mRNA or genomic DNA sequences described herein. The nucleic acid probe can be, for example, a full-length nucleic acid molecule, or a portion thereof, such as an oligonucleotide of at least 15, 30, 50, 100, 250 or 500 nucleotides in length that is sufficient to specifically hybridize under stringent conditions to appropriate mRNA or genomic DNA. For example, the nucleic acid probe can comprise all or a portion of the nucleotide sequence of any one of SEQ ID NO:1-7, as described herein, optionally comprising at least one allele of a marker described herein, or the probe can be the complementary sequence of such a sequence. Other suitable probes for use in the diagnostic assays of the invention are described herein. Hybridization can be performed by methods well known to the person skilled in the art (see, e.g., Current Protocols in Molecular Biology, Ausubel, F. et al., eds., John Wiley & Sons, including all supplements). In one embodiment, hybridization refers to specific hybridization, i.e., hybridization with no mismatches (exact hybridization). In one embodiment, the hybridization conditions for specific hybridization are high stringency.

Specific hybridization, if present, is detected using standard methods. If specific hybridization occurs between the nucleic acid probe and the nucleic acid in the test sample, then the sample contains the allele that is complementary to the nucleotide that is present in the nucleic acid probe. The process can be repeated for any markers of the present invention, or markers that make up a haplotype of the present invention, or multiple probes can be used concurrently to detect more than one marker alleles at a time.

In one preferred embodiment, a method utilizing a detection oligonucleotide probe comprising a fluorescent moiety or group at its 3' terminus and a quencher at its 5' terminus, and an enhancer oligonucleotide, is employed, as described by Kutyavin et al. (*Nucleic Acid Res.* 34:e128 (2006)). The fluorescent moiety can be Gig Harbor Green or Yakima Yellow, or other suitable fluorescent moieties. The detection probe is designed to hybridize to a short nucleotide sequence that includes the SNP polymorphism to be detected. Preferably, the SNP is anywhere from the terminal residue to −6 residues from the 3' end of the detection probe. The enhancer is a short oligonucleotide probe which hybridizes to the DNA template 3' relative to the detection probe. The probes are designed such that a single nucleotide gap exists between the detection probe and the enhancer nucleotide probe when both are bound to the template. The gap creates a synthetic abasic site that is recognized by an endonuclease, such as Endonuclease IV. The enzyme cleaves the dye off the fully complementary detection probe, but cannot cleave a detection probe containing a mismatch. Thus, by measuring the fluorescence of the released fluorescent moiety, assessment of the presence of a particular allele defined by nucleotide sequence of the detection probe can be performed.

The detection probe can be of any suitable size, although preferably the probe is relatively short. In one embodiment, the probe is from 5-100 nucleotides in length. In another embodiment, the probe is from 10-50 nucleotides in length, and in another embodiment, the probe is from 12-30 nucleotides in length. Other lengths of the probe are possible and within scope of the skill of the average person skilled in the art.

In a preferred embodiment, the DNA template containing the SNP polymorphism is amplified by Polymerase Chain Reaction (PCR) prior to detection. In such an embodiment, the amplified DNA serves as the template for the detection probe and the enhancer probe.

Certain embodiments of the detection probe, the enhancer probe, and/or the primers used for amplification of the template by PCR include the use of modified bases, including modified A and modified G. The use of modified bases can be useful for adjusting the melting temperature of the nucleotide molecule (probe and/or primer) to the template DNA, for example for increasing the melting temperature in regions containing a low percentage of G or C bases, in which modified A with the capability of forming three hydrogen bonds to its complementary T can be used, or for decreasing the melting temperature in regions containing a high percentage of G or C bases, for example by using modified G bases that form only two hydrogen bonds to their complementary C base in a double stranded DNA molecule. In a preferred embodiment, modified bases are used in the design of the detection nucleotide probe. Any modified base known to the skilled person can be selected in these methods, and the selection of suitable bases is well within the scope of the skilled person based on the teachings herein and known bases available from commercial sources as known to the skilled person.

Alternatively, a peptide nucleic acid (PNA) probe can be used in addition to, or instead of, a nucleic acid probe in the hybridization methods described herein. A PNA is a DNA mimic having a peptide-like, inorganic backbone, such as N-(2-aminoethyl)glycine units, with an organic base (A, G, C, T or U) attached to the glycine nitrogen via a methylene carbonyl linker (see, for example, Nielsen, P., et al., *Bioconjug. Chem.* 5:3-7 (1994)). The PNA probe can be designed to specifically hybridize to a molecule in a sample suspected of containing one or more particular marker alleles or haplotypes that are associated with type 2 diabetes. Hybridization of the PNA probe is thus diagnostic for type 2 diabetes or a susceptibility to type 2 diabetes In one embodiment of the invention, a test sample containing genomic DNA obtained from the subject is collected and the polymerase chain reaction (PCR) is used to amplify a fragment comprising one or more markers or haplotypes of the present invention. As described herein, identification of a particular marker allele or haplotype can be accomplished using a variety of methods (e.g., sequence analysis, analysis by restriction digestion, specific hybridization, single stranded conformation polymorphism assays (SSCP), electrophoretic analysis, etc.). In another embodiment, diagnosis is accomplished by expression analysis, for example by using quantitative PCR (kinetic thermal cycling). This technique can, for example, utilize commercially available technologies, such as TaqMan® (Applied Biosystems, Foster City, Calif.). The technique can assess the presence of an alteration in the expression or composition of a polypeptide or splicing variant(s). Further, the expression of the variant(s) can be quantified as physically or functionally different.

In another embodiment of the methods of the invention, analysis by restriction digestion can be used to detect a particular allele if the allele results in the creation or elimination of a restriction site relative to a reference sequence. Restriction fragment length polymorphism (RFLP) analysis can be conducted, e.g., as described in Current Protocols in Molecular Biology, supra. The digestion pattern of the relevant DNA fragment indicates the presence or absence of the particular allele in the sample.

Sequence analysis can also be used to detect specific alleles or haplotypes. Therefore, in one embodiment, determination of the presence or absence of a particular marker alleles or haplotypes comprises sequence analysis of a test sample of DNA or RNA obtained from a subject or individual. PCR or other appropriate methods can be used to amplify a portion of a nucleic acid that contains a polymorphic marker or haplotype, and the presence of specific alleles can then be detected directly by sequencing the polymorphic site (or multiple polymorphic sites in a haplotype) of the genomic DNA in the sample.

In another embodiment, arrays of oligonucleotide probes that are complementary to target nucleic acid sequence segments from a subject, can be used to identify particular alleles at polymorphic sites. For example, an oligonucleotide array can be used. Oligonucleotide arrays typically comprise a plurality of different oligonucleotide probes that are coupled to a surface of a substrate in different known locations. These arrays can generally be produced using mechanical synthesis methods or light directed synthesis methods that incorporate a combination of photolithographic methods and solid phase oligonucleotide synthesis methods, or by other methods known to the person skilled in the art (see, e.g., Bier, F. F., et al. *Adv Biochem Eng Biotechnol* 109:433-53 (2008); Hoheisel, J. D., *Nat Rev Genet.* 7:200-10 (2006); Fan, J. B., et al. *Methods Enzymol* 410:57-73 (2006); Raqoussis, J. & Elvidge, G., *Expert Rev Mol Diagn* 6:145-52 (2006); Mockler, T. C., et al *Genomics* 85:1-15 (2005), and references cited therein, the entire teachings of each of which are incorporated by reference herein). Many additional descriptions of the preparation and use of oligonucleotide arrays for detection of polymorphisms can be found, for example, in U.S. Pat. No. 6,858,394, U.S. Pat. No. 6,429,027, U.S. Pat. No. 5,445,934, U.S. Pat. No. 5,700,637, U.S. Pat. No. 5,744,305, U.S. Pat. No. 5,945,334, U.S. Pat. No. 6,054,270, U.S. Pat. No. 6,300, 063, U.S. Pat. No. 6,733,977, U.S. Pat. No. 7,364,858, EP 619 321, and EP 373 203, the entire teachings of which are incorporated by reference herein.

Other methods of nucleic acid analysis that are available to those skilled in the art can be used to detect a particular allele at a polymorphic site. Representative methods include, for example, direct manual sequencing (Church and Gilbert, *Proc. Natl. Acad. Sci. USA*, 81: 1991-1995 (1988); Sanger, F., et al., *Proc. Natl. Acad. Sci. USA*, 74:5463-5467 (1977); Beavis, et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield, V., et al., *Proc. Natl. Acad. Sci. USA*, 86:232-236 (1989)), mobility shift analysis (Orita, M., et al., *Proc. Natl. Acad. Sci. USA*, 86:2766-2770 (1989)), restriction enzyme analysis (Flavell, R., et al., *Cell*, 15:25-41 (1978); Geever, R., et al., *Proc. Natl. Acad. Sci. USA*, 78:5081-5085 (1981)); heteroduplex analysis; chemical mismatch cleavage (CMC) (Cotton, R., et al., *Proc. Natl. Acad. Sci. USA*, 85:4397-4401 (1985)); RNase protection assays (Myers, R., et al., *Science*, 230:1242-1246 (1985); use of polypeptides that recognize nucleotide mismatches, such as *E. coli* mutS protein; and allele-specific PCR.

In another embodiment of the invention, determination of disease susceptibility can be made by examining expression and/or composition of a polypeptide encoded by a nucleic acid associated with, or in linkage disequilibrium with, a marker associated with the disease, in those instances where the genetic marker(s) or haplotype(s) of the present invention result in a change in the composition or expression of the polypeptide. In certain embodiments, the polypeptide is encoded by a gene selected from the group consisting of HCCA2, KRTAP1, KRTAP2, KRTAP3, KRTAP4, KRTAP5 (keratin associated proteins 1-5), DUSP8 (dual specificity phosphatase 8) and CTSD (cathepsin D). Thus, determination of a susceptibility to the disease can be made by examining expression and/or composition of such polypeptides, in those instances where the genetic marker or haplotype of the present invention results in a change in the composition or expression of the polypeptide. Possible mechanisms affecting such nearby genes include, e.g., effects on transcription, effects on RNA splicing, alterations in relative amounts of alternative splice forms of mRNA, effects on RNA stability, effects on transport from the nucleus to cytoplasm, and effects on the efficiency and accuracy of translation.

Thus, in another embodiment, the variants (markers or haplotypes) presented herein affect the expression of a gene selected from the group consistinf of HCCA2, KRTAP1, KRTAP2, KRTAP3, KRTAP4, KRTAP5, DUSP8 and CTSD. It is well known that regulatory element affecting gene expression may be located far away, even as far as tenths or hundreds of kilobases away, from the promoter region of a gene. By assaying for the presence or absence of a particular marker allele, it is may thus possible to assess the expression level of a nearby gene. It is thus contemplated that the detection of the markers or haplotypes of the present invention can be used for assessing expression levels of a gene selected from the group consistinf of HCCA2, KRTAP1, KRTAP2, KRTAP3, KRTAP4, KRTAP5, DUSP8 and CTSD.

A variety of methods can be used for detecting protein expression levels, including enzyme linked immunosorbent assays (ELISA), Western blots, immunoprecipitations and immunofluorescence. A test sample from a subject is assessed for the presence of an alteration in the expression and/or an alteration in composition of the polypeptide encoded by a particular nucleic acid. An alteration in expression of a polypeptide encoded by the nucleic acid can be, for example, an alteration in the quantitative polypeptide expression (i.e., the amount of polypeptide produced). An alteration in the composition of a polypeptide encoded by the nucleic acid is an alteration in the qualitative polypeptide expression (e.g., expression of a mutant polypeptide or of a different splicing variant). In one embodiment, diagnosis of a susceptibility to is made by detecting a particular splicing variant, or a particular pattern of splicing variants.

Both such alterations (quantitative and qualitative) can also be present. An "alteration" in the polypeptide expression or composition, as used herein, refers to an alteration in expression or composition in a test sample, as compared to the expression or composition of the polypeptide in a control sample. A control sample is a sample that corresponds to the test sample (e.g., is from the same type of cells), and is from a subject who is not affected by, and/or who does not have a susceptibility to, a particular disease (e.g., type 2 diabetes, breast cancer, basal cell carcinoma). In one embodiment, the control sample is from a subject that does not possess a marker allele or haplotype associated with the disease, as described herein. Similarly, the presence of one or more different splicing variants in the test sample, or the presence of significantly different amounts of different splicing variants in the test sample, as compared with the control sample, can be indicative of a susceptibility to the disease. An alteration in the expression or composition of the polypeptide in the test sample, as compared with the control sample, can be indicative of a specific allele in the instance where the allele alters a splice site relative to the reference in the control sample. Various means of examining expression or composition of a polypeptide encoded by a nucleic acid are known to the person skilled in the art and can be used, including spectroscopy, colorimetry, electrophoresis, isoelectric focusing, and immunoassays (e.g., David et al., U.S. Pat. No. 4,376,110) such as immunoblotting (see, e.g., Current Protocols in Molecular Biology, particularly chapter 10, supra).

For example, in one embodiment, an antibody (e.g., an antibody with a detectable label) that is capable of binding to a polypeptide encoded by a nucleic acid associated with a particular disease can be used. Antibodies can be polyclonal or monoclonal. An intact antibody, or a fragment thereof (e.g., Fv, Fab, Fab', F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a labeled secondary antibody (e.g., a fluorescently-labeled secondary antibody) and end-labeling of a DNA probe with biotin such that it can be detected with fluorescently-labeled streptavidin.

In one embodiment of this method, the level or amount of a polypeptide in a test sample is compared with the level or amount of the polypeptide in a control sample. A level or amount of the polypeptide in the test sample that is higher or lower than the level or amount of the polypeptide in the control sample, such that the difference is statistically significant, is indicative of an alteration in the expression of the polypeptide encoded by the nucleic acid, and is diagnostic for a particular allele or haplotype responsible for causing the difference in expression. Alternatively, the composition of the polypeptide in a test sample is compared with the composition of the polypeptide in a control sample. In another embodiment, both the level or amount and the composition of the polypeptide can be assessed in the test sample and in the control sample.

In another embodiment, determination of a susceptibility to a disease is made by detecting at least one marker or haplotype as described herein, in combination with an additional protein-based, RNA-based or DNA-based assay.

Kits

Kits useful in the methods of the invention comprise components useful in any of the methods described herein, including for example, primers for nucleic acid amplification, hybridization probes, restriction enzymes (e.g., for RFLP analysis), allele-specific oligonucleotides, antibodies that bind to an altered polypeptide encoded by a nucleic acid of the invention as described herein (e.g., a genomic segment comprising at least one polymorphic marker and/or haplotype of the present invention) or to a non-altered (native) polypeptide encoded by a nucleic acid of the invention as described herein, means for amplification of a nucleic acid associated with a particular disease (e.g., type 2 diabetes, breast cancer, basal cell carcinoma), means for analyzing the nucleic acid sequence of a nucleic acid associated with the disease, means for analyzing the amino acid sequence of a polypeptide encoded by a nucleic acid associated with the disease, etc. The kits can for example include necessary buffers, nucleic acid primers for amplifying nucleic acids of the invention (e.g., a nucleic acid segment comprising one or more of the polymorphic markers as described herein), and reagents for allele-specific detection of the fragments amplified using such primers and necessary enzymes (e.g., DNA polymerase).

Additionally, kits can provide reagents for assays to be used in combination with the methods of the present invention, e.g., reagents for use with other diagnostic assays.

In one embodiment, the invention pertains to a kit for assaying a sample from a subject to detect a susceptibility to a disease condition selected from the group consisting of type 2 diabetes, breast cancer and basal cell carcinoma in a subject, wherein the kit comprises reagents necessary for selectively detecting at least one allele of at least one polymorphism of the present invention in the genome of the individual. In a particular embodiment, the reagents comprise at least one contiguous oligonucleotide that hybridizes to a fragment of the genome of the individual comprising at least one polymorphism of the present invention. In another embodiment, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one polymorphism associated with the disease. In one embodiment, the polymorphism is selected from the group consisting of the polymorphisms rs2237892, rs231362, rs4731702, rs233449, rs3817198, and rs157935 and polymorphic markers in linkage disequilibrium therewith. In another embodiment, the polymorphism is selected from the group consisting of rs2334499, rs1038727, rs7131362, rs748541, rs4752779, rs4752780, rs4752781, rs4417225, rs10769560, rs17245346, rs11607954, rs10839220, and rs11600502. In yet another embodiment the fragment is at least 20 base pairs in size. Such oligonucleotides or nucleic acids (e.g., oligonucleotide primers) can be designed using portions of the nucleic acid sequence flanking polymorphisms (e.g., SNPs or microsatellites) that are associated with the disease. In another embodiment, the kit comprises one or more labeled nucleic acids capable of allele-specific detection of one or more specific polymorphic markers or haplotypes, and reagents for detection of the label. Suitable labels include, e.g., a radioisotope, a fluorescent label, an enzyme label, an enzyme co-factor label, a magnetic label, a spin label, an epitope label.

In a preferred embodiment, the DNA template containing the SNP polymorphism is amplified by Polymerase Chain Reaction (PCR) prior to detection, and primers for such amplification are included in the reagent kit. In such an embodiment, the amplified DNA serves as the template for the detection probe and the enhancer probe.

In one embodiment, the DNA template is amplified by means of Whole Genome Amplification (WGA) methods, prior to assessment for the presence of specific polymorphic markers as described herein. Standard methods well known to the skilled person for performing WGA may be utilized, and are within scope of the invention. In one such embodiment, reagents for performing WGA are included in the reagent kit.

In certain embodiments, determination of the presence of the marker or haplotype is indicative of a susceptibility (increased susceptibility or decreased susceptibility) to type 2 diabetes. In another embodiment, determination of the presence of the marker or haplotype is indicative of response to a therapeutic agent for type 2 diabetes. In another embodiment, the presence of the marker or haplotype is indicative of prognosis type 2 diabetes. In yet another embodiment, the presence of the marker or haplotype is indicative of progress of treatment of type 2 diabetes. Such treatment may include intervention by surgery, medication or by other means (e.g., lifestyle changes).

In a further aspect of the present invention, a pharmaceutical pack (kit) is provided, the pack comprising a therapeutic agent and a set of instructions for administration of the therapeutic agent to humans diagnostically tested for one or more variants of the present invention, as disclosed herein. The therapeutic agent can be a small molecule drug, an antibody, a peptide, an antisense or RNAi molecule, or other therapeutic molecules. In one embodiment, an individual identified as a carrier of at least one variant of the present invention is instructed to take a prescribed dose of the therapeutic agent. In one such embodiment, an individual identified as a homozygous carrier of at least one variant of the present invention is instructed to take a prescribed dose of the therapeutic agent. In another embodiment, an individual identified as a non-carrier of at least one variant of the present invention is instructed to take a prescribed dose of the therapeutic agent.

In certain embodiments, the kit further comprises a set of instructions for using the reagents comprising the kit. In certain embodiments, the kit further comprises a collection of data comprising correlation data between the polymorphic markers assessed by the kit and susceptibility to the disease.

Therapeutic Agents

Therapeutic Agents for Type 2 Diabetes

Currently available Type 2 diabetes medication (apart from insulin) falls into six main classes of drugs: sulfonylureas, meglitinides, biguanides, thiazolidinediones, alpha-glucosidase inhibitors and a new class of drugs called DPP-4 inhibitors. These classes of drugs work in different ways to lower blood glucose levels.

1. Sulfonylureas. Sulfonylureas stimulate the beta cells of the pancreas to release more insulin.
2. Meglitinides. Meglitinides are drugs that also stimulate the beta cells to release insulin.
3. Biguanides. Biguanides lower blood glucose levels primarily by decreasing the amount of glucose produced by the liver. Metformin also helps to lower blood glucose levels by making muscle tissue more sensitive to insulin so glucose can be absorbed.
4. Thiazolidinediones. These drugs help insulin work better in the muscle and fat and also reduce glucose production in the liver.
5. Alpha-glucosidase inhibitors. These drugs help the body to lower blood glucose levels by blocking the breakdown of starches, such as bread, potatoes, and pasta in the intestine. They also slow the breakdown of some sugars, such as table sugar. Their action slows the rise in blood glucose levels after a meal. They should be taken with the first bite of a meal.
6. DPP-4 Inhibitors. A new class of medications called DPP-4 inhibitors help improve A1C without causing hypoglycemia. They work by preventing the breakdown of a naturally occurring compound in the body, GLP-1. GLP-1 reduces blood glucose levels in the body, but is broken down very quickly so it does not work well when injected as a drug itself. By interfering in the process that breaks down GLP-1, DPP-4 inhibitors allow it to remain active in the body longer, lowering blood glucose levels only when they are elevated.

Examples of available drugs in these classes are listed in Agent Table 1.

Agent Table 1

| Drug Class | Generic name | Brand name |
|---|---|---|
| Biguanides | metformin | Glucophage, Glucophage XR, Glycon |
|  | metformin plus glyburide | Glucovance |
| Thiazolidinediones | pioglitazone | Actos |
|  | rosiglitazone | Avandia |
| Sulfonylureas | acetohexamide | Dymelor |
|  | chlorpropamide | Diabinese |
|  | gliclazide | Diamicron |
|  | Diamicron | MR |
|  | glimepiride | Amaryl |
|  | glipizide | Glucotrol, Glucotrol XL |
|  | glyburide | Micronase, DiaBeta, Glynase PresTab |
|  | glyburide plus metformin | Glucovance |
|  | tolazamide | Tolinase |
|  | tolbutamide | Orinase, Tol-Tab |
| Meglitinides | nateglinide | Starlix |
|  | repaglinide | Prandin, Gluconorm |
| Alpha-glucosidase inhibitors | acarbose | Precose, Prandase |
|  | miglitol | Glyset |
| DPP-4 Inhibitors | sitagliptin | Januvia |

Additionally, a combination therapy comprising Biguanide and Sulphonylureas has been used for treatment of Type 2 diabetes.

Additional Type 2 diabetes drugs are listed Agent Table 2.

Agent Table 2

| Compound name(s) | Compound name (generated using Autonom, ISIS Draw version 2.5 from MDL Information Systems) | Company | Compound Reference | Indications |
|---|---|---|---|---|
| AR-0133418 (SN-4521) | 1-(4-Methoxy-benzyl)-3-(5-nitro-thiazol-2-yl)-urea | AstraZeneca |  | AD |
| AR-025028 | NSD | AstraZeneca |  |  |
| CT 98023 | N-[4-(2,4-Dichloro-phenyl)-5-(1H-imidazol-2-yl)-pyrimidin-2-yl]-N'-(5-nitro-pyridin-2-yl)-ethane-1,2-diamine | Chiron Corp |  | non-insulin dependent diabetes |
| CT-20026 | NSD | Chiron Corp | Wagman et al., Curr Pharm. Des 2004: 10(10) 1105-37 | non-insulin dependent diabetes |
| CT-21022 | NSD | Chiron Corp |  | non-insulin dependent diabetes |
| CT-20014 | NSD | Chiron Corp |  | non-insulin dependent diabetes |
| CT-21018 | NSD | Chiron Corp |  | non-insulin dependent diabetes |
| CHIR-98025 | NSD | Chiron Corp |  | non-insulin dependent diabetes |
| CHIR-99021 | NSD | Chiron Corp | Wagman et al., Curr Pharm. Des 2004: 10(10) 1105-37 | non-insulin dependent diabetes |

-continued

Agent Table 2

| Compound name(s) | Compound name (generated using Autonom, ISIS Draw version 2.5 from MDL Information Systems) | Company | Compound Reference | Indications |
|---|---|---|---|---|
| CG-100179 | NSD | CrystalGenomics and Yuyu Cyclacel Ltd. | WO-2004065370 | type 2 diabetes (Korea) non-insulin dependent diabetes, among others. |
| | 4[2-(4-Dimethylamino-3-nitro-phenylamino)-pyrimidin-4-yl]-3,5-dimethyl-1H-pyrrole-2-carbonitrile | | | |
| NP-01139, NP-031112, NP-03112, NP-00361 | 4-Benzyl-2-methyl-[1,2,4]thiadiazolidine-3,5-dione | Neuropharma SA | | CNS disorders, AD |
| | 3-[9-Fluoro-2-(piperidine-1-carbonyl)-1,2,3,4-tetrahydro-[1,4]diazepino[6,7,1-hi]indol-7-yl]-4-imidazo[1,2-a]pyridin-3-yl-pyrrole-2,5-dione | Eli Lilly & Co | | non-insulin dependent diabetes |
| GW-784752x, GW-784775, SB-216763, SB-415286 | Cyclopentanecarboxylic acid (6-pyridin-3-yl-furo[2,3-d]pyrimidin-4-yl)-amide | GSK | WO-03024447 (compound referenced: 4-[2-(2-bromophenyl)-4-(4-fluorophenyl)-1H-imidazol-5-yl]pyridine | non-insulin dependent diabetes, neurodegenerative disease |
| NNC-57-0511, NNC-57-0545, NNC-57-0588 | 1-(4-Amino-furazan-3-yl)-5-piperidin-1-ylmethyl-1H-[1,2,3]triazole-4-carboxylic acid [1-pyridin-4-yl-meth-(E)-ylidene]-hydrazide | Novo Nordisk | | non-insulin dependent diabetes, |
| CP-70949 | NSD | Pfizer | | Hypoglycemic agent |
| VX-608 | NSD | | | Cerebrovascular ischemia, non-insulin dependent diabetes |
| KP-403 class | NSD | Kinetek | | Nuclear factor kappa B modulator, Anti-inflammatory, Cell cycle inhibitor, Glycogen synthase kinase-3 beta inhibitor |
| BYETTA (exenatide) | Exenatide: $C_{184}H_{282}N_{50}O_{60}S$ - Amino acid sequence: H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$ | Amylin/Eli Lilly & Co | | non-insulin dependent diabetes |
| Vildagliptin (LAF237) | NSD | Novartis | | non-insulin dependent diabetes - DPP-4 inhibitor |

Cardiovascular disease risk can be reduced in patients with diabetes. While controlling hyperglycemia remains important, the identification and treatment of other CVD risk factors is also vital. Interventions that have been shown to decrease CVD events in diabetics include the treatment of hypertension and hyperlipidemia, aspirin therapy, use of ACE inhibitors, and smoking cessation. The United Kingdom Prospective Diabetes Study demonstrated that lowering blood pressure significantly reduces stroke events, diabetes-related deaths, heart failure, and microvascular complications in patients with type 2 diabetes. Lipid management aimed at lowering LDL cholesterol, raising HDL cholesterol, and reducing triglycerides has been shown to decrease macrovascular disease and mortality in patients with type 2 diabetes, particularly those who have had prior cardiovascular events. The benefits of cholesterol lowering with statin medication in reducing CVD events also has been demonstrated in diabetic patients with average cholesterol levels and in individuals with impaired fasting glucose. ACE inhibitors have been shown to decrease cardiovascular events in type 2 diabetes patients with or without hypertension. Studies have documented the benefits of aspirin therapy and smoking cessation in reducing CVD.

Tight control of blood glucose and blood pressure are important treatments for kidney disease. Blood pressure has a dramatic effect on the rate at which the disease progresses. Even a mild rise in blood pressure can be harmful for the kidney. ACE inhibitors are recommended for most people with diabetes, high blood pressure, and kidney disease. Recent studies suggest that ACE inhibitors slow kidney disease in addition to lowering blood pressure and are helpful even in people who do not have high blood pressure. Accumulating evidence shows that diabetic vascular disease develops in individuals who are genetically susceptible and that hyperglycemia in itself is not sufficient to cause vascular complications. Since diabetic retinopathy is an unevitable and well known consequence of type 2 diabetes, with its devastating consequences, its detection at the very early stages is of utmost importance. Early intervention, through attention to glycaemic control together with other risk factors such as smoking and hypertension, may modify the further progress of this complication (Clarke, B. F., in *Type 2 diabetes in Children and Adolescents*, Kelnar, C. (ed); London, Chapman & Hall, pp 539-51 (1994)).

Variants described herein to confer risk of type 2 diabetes can be used to identify novel therapeutic targets for preventing and/or ameliorating vascular complications of type 2 diabetes. For example, the HCCA2 gene or its protein product, as well as genes or their products that are directly or indirectly regulated by, or interact with, the HCCA2 gene or its products, can be targeted for the development of therapeutic agents to treat vascular complications of type 2 diabetes, or prevent or delay onset of symptoms associated with these vascular complications. Therapeutic agents may comprise one or more of, for example, small non-protein and non-nucleic acid molecules, proteins, peptides, protein fragments, nucleic acids (DNA, RNA), PNA (peptide nucleic acids), or their derivatives or mimetics which can modulate the function and/or levels of the target genes or their gene products.

The nucleic acids and/or variants described herein, or nucleic acids comprising their complementary sequence, may also be used as antisense constructs to control gene expression in cells, tissues or organs. The methodology associated with antisense techniques is well known to the skilled artisan, and is for example described and reviewed in *AntisenseDrug Technology: Principles, Strategies, and Applications*, Crooke, ed., Marcel Dekker Inc., New York (2001). In general, antisense agents (antisense oligonucleotides) are comprised of single stranded oligonucleotides (RNA or DNA) that are capable of binding to a complimentary nucleotide segment. By binding the appropriate target sequence, an RNA-RNA, DNA-DNA or RNA-DNA duplex is formed. The antisense oligonucleotides are complementary to the sense or coding strand of a gene. It is also possible to form a triple helix, where the antisense oligonucleotide binds to duplex DNA.

Several classes of antisense oligonucleotide are known to those skilled in the art, including cleavers and blockers. The former bind to target RNA sites, activate intracellular nucleases (e.g., RnaseH or Rnase L), that cleave the target RNA. Blockers bind to target RNA, inhibit protein translation by steric hindrance of the ribosomes. Examples of blockers include nucleic acids, morpholino compounds, locked nucleic acids and methylphosphonates (Thompson, *Drug Discovery Today*, 7:912-917 (2002)). Antisense oligonucleotides are useful directly as therapeutic agents, and are also useful for determining and validating gene function, for example by gene knock-out or gene knock-down experiments. Antisense technology is further described in Layery et al., *Curr. Opin. Drug Discov. Devel.* 6:561-569 (2003), Stephens et al., *Curr. Opin. Mol. Ther.* 5:118-122 (2003), Kurreck, *Eur. J. Biochem.* 270:1628-44 (2003), Dias et al., *Mol. Cancer. Ter.* 1:347-55 (2002), Chen, *Methods Mol. Med.* 75:621-636 (2003), Wang et al., *Curr. Cancer Drug Targets* 1:177-96 (2001), and Bennett, *Antisense Nucleic Acid Drug. Dev.* 12:215-24 (2002).

In certain embodiments, the antisense agent is an oligonucleotide that is capable of binding to a nucleotide segment of a gene selected from the group consisting of the HCCA2 gene, the KRTAP5-1 gene, the KRTAP5-2 gene, the KRTAP5-3 gene, the KRTAP5-4 gene, the KRTAP5-5 gene, the KRTAP5-6 gene, the DUSP8 gene and the CTSD gene. Antisense nucleotides can be from 5-500 nucleotides in length, including 5-200 nucleotides, 5-100 nucleotides, 10-50 nucleotides, and 10-30 nucleotides. In certain preferred embodiments, the antisense nucleotides are from 14-50 nucleotides in length, including 14-40 nucleotides and 14-30 nucleotides. In certain such embodiments, the antisense nucleotide is capable of binding to a nucleotide segment of the HCCA2 gene.

The variants described herein can also be used for the selection and design of antisense reagents that are specific for particular variants. Using information about the variants described herein, antisense oligonucleotides or other antisense molecules that specifically target mRNA molecules that contain one or more variants of the invention can be designed. In this manner, expression of mRNA molecules that contain one or more variant of the present invention (markers and/or haplotypes) can be inhibited or blocked. In one embodiment, the antisense molecules are designed to specifically bind a particular allelic form (i.e., one or several variants (alleles and/or haplotypes)) of the target nucleic acid, thereby inhibiting translation of a product originating from this specific allele or haplotype, but which do not bind other or alternate variants at the specific polymorphic sites of the target nucleic acid molecule. As antisense molecules can be used to inactivate mRNA so as to inhibit gene expression, and thus protein expression, the molecules can be used for disease treatment. The methodology can involve cleavage by means of ribozymes containing nucleotide sequences complementary to one or more regions in the mRNA that attenuate the ability of the mRNA to be translated. Such mRNA regions include, for example, protein-coding regions, in particular protein-coding regions corresponding to catalytic activity, substrate and/or ligand binding sites, or other functional domains of a protein.

The phenomenon of RNA interference (RNAi) has been actively studied for the last decade, since its original discovery in *C. elegans* (Fire et al., *Nature* 391:806-11 (1998)), and in recent years its potential use in treatment of human disease has been actively pursued (reviewed in Kim & Rossi, *Nature Rev. Genet.* 8:173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a protein-RNA complex to specific sites on a target mRNA, leading to cleavage of the mRNA (Thompson, *Drug Discovery Today*, 7:912-917 (2002)). The siRNA molecules are typically about 20, 21, 22 or 23 nucleotides in length. Thus, one aspect of the invention relates to isolated nucleic acid molecules, and the use of those molecules for RNA interference, i.e. as small interfering RNA molecules (siRNA). In one embodiment, the isolated nucleic acid molecules are 18-26 nucleotides in length, preferably 19-25 nucleotides in length, more preferably 20-24 nucleotides in length, and more preferably 21, 22 or 23 nucleotides in length.

Another pathway for RNAi-mediated gene silencing originates in endogenously encoded primary microRNA (pri-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, *Nature Rev. Genet.* 8:173-204 (2007)).

Clinical applications of RNAi include the incorporation of synthetic siRNA duplexes, which preferably are approximately 20-23 nucleotides in size, and preferably have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules (typically 25-30 nucleotides in length, preferably about 27 nucleotides), as well as small hairpin RNAs (shRNAs; typically about 29 nucleotides in length). The latter are naturally expressed, as described in Amarzguioui et al. (*FEBS Lett.* 579:5974-81 (2005)). Chemically synthetic siRNAs and shRNAs are substrates for in vivo processing, and in some cases provide more potent gene-silencing than shorter designs (Kim et al., *Nature Biotechnol.* 23:222-226 (2005); Siolas et al., *Nature Biotechnol.* 23:227-231 (2005)). In general siRNAs provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., *Nature Biotechnol.* 23:559-565 (2006); Brummelkamp et al., *Science* 296: 550-553 (2002)).

Since RNAi molecules, including siRNA, miRNA and shRNA, act in a sequence-dependent manner, the variants presented herein can be used to design RNAi reagents that recognize specific nucleic acid molecules comprising specific alleles and/or haplotypes, while not recognizing nucleic acid molecules comprising other alleles or haplotypes. These RNAi reagents can thus recognize and destroy the target nucleic acid molecules. As with antisense reagents, RNAi reagents can be useful as therapeutic agents (i.e., for turning off disease-associated genes or disease-associated gene variants), but may also be useful for characterizing and validating gene function (e.g., by gene knock-out or gene knock-down experiments).

Delivery of RNAi may be performed by a range of methodologies known to those skilled in the art. Methods utilizing non-viral delivery include cholesterol, stable nucleic acid-lipid particle (SNALP), heavy-chain antibody fragment (Fab), aptamers and nanoparticles. Viral delivery methods include use of lentivirus, adenovirus and adeno-associated virus. The siRNA molecules are in some embodiments chemically modified to increase their stability. This can include modifications at the 2' position of the ribose, including 2'-O-methylpurines and 2'-fluoropyrimidines, which provide resistance to Rnase activity. Other chemical modifications are possible and known to those skilled in the art.

The following references provide a further summary of RNAi, and possibilities for targeting specific genes using RNAi: Kim & Rossi, *Nat. Rev. Genet.* 8:173-184 (2007), Chen & Rajewsky, *Nat. Rev. Genet.* 8: 93-103 (2007), Reynolds, et al., *Nat. Biotechnol.* 22:326-330 (2004), Chi et al., *Proc. Natl. Acad. Sci. USA* 100:6343-6346 (2003), Vickers et al., *J. Biol. Chem.* 278:7108-7118 (2003), Agami, *Curr. Opin. Chem. Biol.* 6:829-834 (2002), Layery, et al., *Curr. Opin. Drug Discov. Devel.* 6:561-569 (2003), Shi, *Trends Genet.* 19:9-12 (2003), Shuey et al., *Drug Discov. Today* 7:1040-46 (2002), McManus et al., *Nat. Rev. Genet.* 3:737-747 (2002), Xia et al., *Nat. Biotechnol.* 20:1006-10 (2002), Plasterk et al., *curr. Opin. Genet. Dev.* 10:562-7 (2000), Bosher et al., *Nat. Cell Biol.* 2:E31-6 (2000), and Hunter, *Curr. Biol.* 9:R440-442 (1999).

A genetic defect leading to increased predisposition or risk for development of a disease, such as type 2 diabetes, breast cancer or basal cell carcinoma, or a defect causing the disease, may be corrected permanently by administering to a subject carrying the defect a nucleic acid fragment that incorporates a repair sequence that supplies the normal/wild-type nucleotide(s) at the site of the genetic defect. Such site-specific repair sequence may concompass an RNA/DNA oligonucleotide that operates to promote endogenous repair of a subject's genomic DNA. The administration of the repair sequence may be performed by an appropriate vehicle, such as a complex with polyethelenimine, encapsulated in anionic liposomes, a viral vector such as an adenovirus vector, or other pharmaceutical compositions suitable for promoting intracellular uptake of the adminstered nucleic acid. The genetic defect may then be overcome, since the chimeric oligonucleotides induce the incorporation of the normal sequence into the genome of the subject, leading to expression of the normal/wild-type gene product. The replacement is propagated, thus rendering a permanent repair and alleviation of the symptoms associated with the disease or condition.

The present invention provides methods for identifying compounds or agents that can be used to treat a disease selected from type 2 diabetes, basal cell carcinoma and breast cancer. Thus, the variants of the invention are useful as targets for the identification and/or development of therapeutic agents. In certain embodiments, such methods include assaying the ability of an agent or compound to modulate the activity and/or expression of a nucleic acid that includes at least one of the variants (markers and/or haplotypes) of the present invention, or the encoded product of the nucleic acid (e.g., the HCCA2 gene). This in turn can be used to identify agents or compounds that inhibit or alter the undesired activity or expression of the encoded nucleic acid product. Assays for performing such experiments can be performed in cell-based systems or in cell-free systems, as known to the skilled person. Cell-based systems include cells naturally expressing the nucleic acid molecules of interest, or recombinant cells that have been genetically modified so as to express a certain desired nucleic acid molecule.

Variant gene expression in a patient can be assessed by expression of a variant-containing nucleic acid sequence (for example, a gene containing at least one variant of the present invention, which can be transcribed into RNA containing the at least one variant, and in turn translated into protein), or by altered expression of a normal/wild-type nucleic acid sequence due to variants affecting the level or pattern of expression of the normal transcripts, for example variants in the regulatory or control region of the gene. Assays for gene expression include direct nucleic acid assays (mRNA), assays for expressed protein levels, or assays of collateral compounds involved in a pathway, for example a signal pathway. Furthermore, the expression of genes that are up- or down-regulated in response to the signal pathway can also be assayed. One embodiment includes operably linking a reporter gene, such as luciferase, to the regulatory region of the gene(s) of interest.

Modulators of gene expression can in one embodiment be identified when a cell is contacted with a candidate compound or agent, and the expression of mRNA is determined. The expression level of mRNA in the presence of the candidate compound or agent is compared to the expression level in the absence of the compound or agent. Based on this comparison, candidate compounds or agents for disease treatment can be identified as those modulating the gene expression of the variant gene. When expression of mRNA or the encoded protein is statistically significantly greater in the presence of the candidate compound or agent than in its absence, then the candidate compound or agent is identified as a stimulator or up-regulator of expression of the nucleic acid. When nucleic acid expression or protein level is statistically significantly less in the presence of the candidate compound or agent than in its absence, then the candidate compound is identified as an inhibitor or down-regulator of the nucleic acid expression.

The invention further provides methods of treatment using a compound identified through drug (compound and/or agent) screening as a gene modulator (i.e. stimulator and/or inhibitor of gene expression).

Methods of Assessing Probability of Response to Therapeutic Agents, Methods of Monitoring Progress of Treatment and Methods of Treatment As is known in the art, individuals can have differential responses to a particular therapy (e.g., a therapeutic agent or therapeutic method). Pharmacogenomics addresses the issue of how genetic variations (e.g., the variants (markers and/or haplotypes) of the present invention) affect drug response, due to altered drug disposition and/or abnormal or altered action of the drug. Thus, the basis of the differential response may be genetically determined in part. Clinical outcomes due to genetic variations affecting drug response may result in toxicity of the drug in certain individuals (e.g., carriers or non-carriers of the genetic variants of the present invention), or therapeutic failure of the drug. Therefore, the variants of the present invention may predictive of the manner in which a therapeutic agent and/or method acts on the body, or the way in which the body metabolizes the therapeutic agent.

Accordingly, in one embodiment, the presence of a particular allele at a polymorphic site or haplotype is indicative of a different response, e.g. a different response rate, to a particular treatment modality. This means that a patient diagnosed with a particular disease such as type 2 diabetes, breast cancer or basal cell carcinoma, and carrying a certain allele at a polymorphic or haplotype described herein to be associated with risk of these diseases would respond better to, or worse to, a specific therapeutic, drug and/or other therapy used to treat the disease. The therapeutic can be a therapeutic agent for preventing or ameliorating the disease. This includes agents as set forth in the above under Therapeutic agents. It is also contemplated that the markers described herein may be deterministic of the response of a particular individual towards therapy for type 2 diabetes, basal cell carcinoma and/or breast cancer.

Therefore, the presence or absence of the marker allele or haplotype could aid in deciding what treatment should be used for the patient. For example, for a newly diagnosed patient, the presence of a marker or haplotype of the present invention may be assessed (e.g., through testing DNA derived from a blood sample, as described herein). If the patient is positive for a marker allele or haplotype (that is, at least one specific allele of the marker, or haplotype, is present), then the physician recommends one particular therapy, while if the patient is negative for the at least one allele of a marker, or a haplotype, then a different course of therapy may be recommended (which may include recommending that no immediate therapy, other than serial monitoring for progression of the disease, or appearance of specific symptoms, be performed). Thus, the patient's carrier status could be used to help determine whether a particular treatment modality should be administered. The value lies within the possibilities of being able to diagnose the disease at an early stage, to select the most appropriate treatment, and provide information to the clinician about prognosis/aggressiveness of the disease in order to be able to apply the most appropriate treatment.

In one particular aspect, the invention provides a method of assessing an individual for probability of response to a therapeutic agent for preventing, treating and/or ameliorating symptoms associated with type 2 diabetes, comprising analyzing sequence data about the human individual identifying at least one allele of at least one polymorphic marker selected from the group consisting of rs2237892, rs231362, rs4731702 and rs2334499, and markers in linkage disequilibrium therewith, wherein the at least one allele is associated with a probability of a positive response to the therapeutic agent in humans, and determining the probability of a positive response to the therapeutic agent from the sequence data. In certain embodiments, the method further comprises determining the parental origin of said at least one allele, where determination of particular parental origin of the at least one allele is indicative of positive response to the therapeutic agent. In a preferred embodiment, the therapeutic agent is selected from the group consisting of the agents set forth in Agent Table 1 and Agent Table 2.

In certain embodiments, determination of a paternal origin of allele T of rs2334499, or an allele in linkage disequilibrium therewith, is indicative of a positive response to the therapeutic agent. In certain embodiments, determination of a maternal origin of an allele selected from the group consisting of allele C of rs2237892, allele C of rs231362 and allele C of rs4731702, or alleles in linkage disequilibrium therewith, is indicative of a positive response to the therapeutic agent.

The present invention also relates to methods of monitoring progress or effectiveness of a treatment of type 2 diabetes, basal cell carcinoma and/or breast cancer (including the use of drugs as listed in Agent Table 1 and Agent Table 2 herein for the treatment of type 2 diabetes). This can be done based on the genotype and/or haplotype status of the markers as described herein, i.e., by assessing the absence or presence of at least one allele of at least one polymorphic marker as disclosed herein, or by monitoring expression of genes that are associated with the variants (markers and haplotypes) of the present invention. The risk gene mRNA or the encoded polypeptide can be measured in a tissue sample (e.g., a peripheral blood sample, or a biopsy sample). Expression levels and/or mRNA levels can thus be determined before and during treatment to monitor its effectiveness. Alternatively, or concomitantly, the genotype and/or haplotype status of at least one risk variant is determined before and during treatment to monitor its effectiveness.

Alternatively, biological networks or metabolic pathways containing genes associated with markers and/or haplotypes of the present invention can be monitored by determining mRNA and/or polypeptide levels. This can be done for example, by monitoring expression levels or polypeptides for one or more genes belonging to the network and/or pathway, in samples taken before and during treatment. Alternatively, metabolites of the biological network or metabolic pathway can be determined before and during treatment. Effectiveness of the treatment is determined by comparing observed changes in expression levels/metabolite levels during treatment to corresponding data from healthy subjects.

In a further aspect, the markers of the present invention can be used to increase power and effectiveness of clinical trials. Thus, individuals who are carriers of at least one at-risk variant of the present invention may be more likely to respond favourably to a particular treatment modality. In one embodiment, individuals who carry at-risk variants for gene(s) in a pathway and/or metabolic network for which a particular treatment (e.g., small molecule drug) is targeting, are more likely to be responders to the treatment. In another embodiment, individuals who carry at-risk variants for a gene, which expression and/or function is altered by the at-risk variant, are more likely to be responders to a treatment modality targeting that gene, its expression or its gene product. This application can improve the safety of clinical trials, but can also enhance the chance that a clinical trial will demonstrate statistically significant efficacy, which may be limited to a certain subgroup of the population. Thus, one possible outcome of such a trial is that carriers of certain genetic variants, e.g., the markers and haplotypes of the present invention, are statistically significantly likely to show positive response to the therapeutic agent when taking the therapeutic agent or drug as prescribed.

In a further aspect, the markers and haplotypes of the present invention can be used for targeting the selection of pharmaceutical agents for specific individuals. Personalized selection of treatment modalities, lifestyle changes or combination of lifestyle changes and administration of particular treatment, can be realized by the utilization of the at-risk variants of the present invention. Thus, the knowledge of an individual's status for particular markers of the present invention, can be useful for selection of treatment options that target genes or gene products affected by the at-risk variants of the invention. Certain combinations of variants may be suitable for one selection of treatment options, while other gene variant combinations may target other treatment options. Such combination of variant may include one variant, two variants, three variants, or four or more variants, as needed to determine with clinically reliable accuracy the selection of treatment module.

Computer-Implemented Aspects

As understood by those of ordinary skill in the art, the methods and information described herein may be implemented, in all or in part, as computer executable instructions on known computer readable media. For example, the methods described herein may be implemented in hardware. Alternatively, the method may be implemented in software stored in, for example, one or more memories or other computer readable medium and implemented on one or more processors. As is known, the processors may be associated with one or more controllers, calculation units and/or other units of a computer system, or implanted in firmware as desired. If implemented in software, the routines may be stored in any computer readable memory such as in RAM, ROM, flash memory, a magnetic disk, a laser disk, or other storage medium, as is also known. Likewise, this software may be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

When implemented in software, the software may be stored in any known computer readable medium such as on a magnetic disk, an optical disk, or other storage medium, in a RAM or ROM or flash memory of a computer, processor, hard disk drive, optical disk drive, tape drive, etc. Likewise, the software may be delivered to a user or a computing system via any known delivery method including, for example, on a computer readable disk or other transportable computer storage mechanism.

FIG. 1 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method or apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 1, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 1 illustrates operating system 134, application programs 135, other program modules 136, and program data 137.

The computer 110 may also include other removable/non-removable, volatile/nonvolatile computer storage media. By way of example only, FIG. 1 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 1, provide storage of computer readable instructions, data structures, program modules and other data for the computer 110. In FIG. 1, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The computer 110 may operate in a networked environment using logical connections to one or more remote computers, such as a remote computer 180. The remote computer 180 may be a personal computer, a server, a router, a network PC, a peer device or other common network node, and typically includes many or all of the elements described above relative to the computer 110, although only a memory storage device 181 has been illustrated in FIG. 1. The logical connections depicted in FIG. 1 include a local area network (LAN) 171 and a wide area network (WAN) 173, but may also include other networks. Such networking environments are commonplace in offices, enterprise-wide computer networks, intranets and the Internet.

When used in a LAN networking environment, the computer 110 is connected to the LAN 171 through a network interface or adapter 170. When used in a WAN networking environment, the computer 110 typically includes a modem 172 or other means for establishing communications over the WAN 173, such as the Internet. The modem 172, which may be internal or external, may be connected to the system bus 121 via the user input interface 160, or other appropriate mechanism. In a networked environment, program modules depicted relative to the computer 110, or portions thereof, may be stored in the remote memory storage device. By way of example, and not limitation, FIG. 1 illustrates remote application programs 185 as residing on memory device 181. It will be appreciated that the network connections shown are exemplary and other means of establishing a communications link between the computers may be used.

Although the forgoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

While the risk evaluation system and method, and other elements, have been described as preferably being implemented in software, they may be implemented in hardware, firmware, etc., and may be implemented by any other processor. Thus, the elements described herein may be implemented in a standard multi-purpose CPU or on specifically designed hardware or firmware such as an application-specific integrated circuit (ASIC) or other hard-wired device as desired, including, but not limited to, the computer 110 of FIG. 1. When implemented in software, the software routine may be stored in any computer readable memory such as on a magnetic disk, a laser disk, or other storage medium, in a RAM or ROM of a computer or processor, in any database, etc. Likewise, this software may be delivered to a user or a diagnostic system via any known or desired delivery method including, for example, on a computer readable disk or other transportable computer storage mechanism or over a communication channel such as a telephone line, the internet, wireless communication, etc. (which are viewed as being the same as or interchangeable with providing such software via a transportable storage medium).

Thus, many modifications and variations may be made in the techniques and structures described and illustrated herein without departing from the spirit and scope of the present invention. Thus, it should be understood that the methods and apparatus described herein are illustrative only and are not limiting upon the scope of the invention.

Accordingly, the invention relates to computer-implemented applications using the polymorphic markers and haplotypes described herein, and genotype and/or disease-association data derived therefrom. Such applications can be useful for storing, manipulating or otherwise analyzing genotype data that is useful in the methods of the invention. One example pertains to storing genotype information derived from an individual on readable media, so as to be able to provide the genotype information to a third party (e.g., the individual, a guardian of the individual, a health care provider or genetic analysis service provider), or for deriving information from the genotype data, e.g., by comparing the genotype data to information about genetic risk factors contributing to increased susceptibility to the type 2 diabetes (e.g, type 2 diabetes), and reporting results based on such comparison.

In certain embodiments, computer-readable media suitably comprise capabilities of storing (i) identifier information for at least one polymorphic marker, as described herein; (ii) an indicator of the identity (e.g., presence or absence) of at least one allele of said at least one marker, or a haplotype, in individuals with a disease selected from type 2 diabetes, basal cell carcinoma and breast cancer; and (iii) an indicator of the risk associated with the marker allele.

The susceptibility markers described herein are in certain embodiments useful for interpretation and/or analysis of genotype data, including sequence data characteristic of particular polymorphic markers. Thus in certain embodiments, an identification of an at-risk allele for type 2 diabetes, basal cell carcinoma and/or breast cancer as shown herein, or an allele at a polymorphic marker in LD with such an at-risk marker, is indicative of the individual from whom the genotype data originates is at increased risk of the particular disease for which the marker is predictive. In one such embodiment, genotype data is generated for at least one polymorphic marker, or a marker in linkage disequilibrium therewith. The genotype data is subsequently made available to a third party, such as the individual from whom the data originates, his/her guardian or representative, a physician or health care worker, genetic counselor, or insurance agent, for example via a user interface accessible over the internet, together with an interpretation of the genotype data, e.g., in the form of a risk measure (such as an absolute risk (AR), risk ratio (RR) or odds ratio (OR)) for the disease. In another embodiment, at-risk markers identified in a genotype dataset derived from an individual are assessed and results from the assessment of the risk conferred by the presence of such at-risk varians in the dataset are made available to the third party, for example via a secure web interface, or by other communication means. The results of such risk assessment can be reported in numeric form (e.g., by risk values, such as absolute risk, relative risk, and/or an odds ratio, or by a percentage increase in risk compared with a reference), by graphical means, or by other means suitable to illustrate the risk to the individual from whom the genotype data is derived.

Nucleic Acids and Polypeptides

The nucleic acids and polypeptides described herein can be used in methods and kits of the present invention. An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention can be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material can be purified to essential homogeneity, for example as determined by polyacrylamide gel electrophoresis (PAGE) or column chromatography (e.g., HPLC). An isolated nucleic acid molecule of the invention can comprise at least about 50%, at least about 80% or at least about 90% (on a molar basis) of all macromolecular species present. With regard to genomic DNA, the term "isolated" also can refer to nucleic acid molecules that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the genomic DNA of the cell from which the nucleic acid molecule is derived.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells or heterologous organisms, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Such isolated nucleotide sequences are useful, for example, in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis or other hybridization techniques.

The invention also pertains to nucleic acid molecules that hybridize under high stringency hybridization conditions, such as for selective hybridization, to a nucleotide sequence described herein (e.g., nucleic acid molecules that specifically hybridize to a nucleotide sequence containing a polymorphic site associated with a marker or haplotype described herein). Such nucleic acid molecules can be detected and/or isolated by allele- or sequence-specific hybridization (e.g., under high stringency conditions). Stringency conditions and methods for nucleic acid hybridizations are well known to the skilled person (see, e.g., *Current Protocols in Molecular Biology*, Ausubel, F. et al, John Wiley & Sons, (1998), and Kraus, M. and Aaronson, S., *Methods Enzymol.*, 200:546-556 (1991), the entire teachings of which are incorporated by reference herein.

The percent identity of two nucleotide or amino acid sequences can be determined by aligning the sequences for optimal comparison purposes (e.g., gaps can be introduced in the sequence of a first sequence). The nucleotides or amino acids at corresponding positions are then compared, and the percent identity between the two sequences is a function of the number of identical positions shared by the sequences (i.e., % identity=# of identical positions/total # of positions ×100). In certain embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S, and Altschul, S., *Proc. Natl. Acad. Sci. USA,* 90:5873-5877 (1993). Such an algorithm is incorporated into the NBLAST and XBLAST programs (version 2.0), as described in Altschul, S. et al., *Nucleic Acids Res.,* 25:3389-3402 (1997). When utilizing BLAST and Gapped BLAST programs, the default parameters of the respective programs (e.g., NBLAST) can be used. See the website on the world wide web at ncbi.nlm.nih.gov. In one embodiment, parameters for sequence comparison can be set at score=100, wordlength=12, or can be varied (e.g., W=5 or W=20). Another example of an algorithm is BLAT (Kent, W. J. *Genome Res.* 12:656-64 (2002)).

Other examples include the algorithm of Myers and Miller, CABIOS (1989), ADVANCE and ADAM as described in Torellis, A. and Robotti, C., *Comput. Appl. Biosci.* 10:3-5 (1994); and FASTA described in Pearson, W. and Lipman, D., *Proc. Natl. Acad. Sci. USA,* 85:2444-48 (1988).

In another embodiment, the percent identity between two amino acid sequences can be accomplished using the GAP program in the GCG software package (Accelrys, Cambridge, UK).

The present invention also provides isolated nucleic acid molecules that contain a fragment or portion that hybridizes under highly stringent conditions to a nucleic acid that comprises, or consists of, the nucleotide sequence of any one of SEQ ID NO:1-7, or a nucleotide sequence comprising, or consisting of, the complement of the nucleotide sequence of any one of SEQ ID NO:1-7, wherein the nucleotide sequence comprises at least one polymorphic allele contained in the markers and haplotypes described herein. The nucleic acid fragments of the invention may be at least about 15, at least about 18, 20, 23 or 25 nucleotides, and can be 30, 40, 50, 100, 200, 500, 1000, 10,000 or more nucleotides in length.

The nucleic acid fragments of the invention are used as probes or primers in assays such as those described herein. "Probes" or "primers" are oligonucleotides that hybridize in a base-specific manner to a complementary strand of a nucleic acid molecule. In addition to DNA and RNA, such probes and primers include polypeptide nucleic acids (PNA), as described in Nielsen, P. et al., *Science* 254:1497-1500 (1991). A probe or primer comprises a region of nucleotide sequence that hybridizes to at least about 15, typically about 20-25, and in certain embodiments about 40, 50 or 75, consecutive nucleotides of a nucleic acid molecule. In one embodiment, the probe or primer comprises at least one allele of at least one polymorphic marker or at least one haplotype described herein, or the complement thereof. In particular embodiments, a probe or primer can comprise 100 or fewer nucleotides; for example, in certain embodiments from 6 to 50 nucleotides, or, for example, from 12 to 30 nucleotides. In other embodiments, the probe or primer is at least 70% identical, at least 80% identical, at least 85% identical, at least 90% identical, or at least 95% identical, to the contiguous nucleotide sequence or to the complement of the contiguous nucleotide sequence. In another embodiment, the probe or primer is capable of selectively hybridizing to the contiguous nucleotide sequence or to the complement of the contiguous nucleotide sequence. Often, the probe or primer further comprises a label, e.g., a radioisotope, a fluorescent label, an enzyme label, an enzyme co-factor label, a magnetic label, a spin label, an epitope label.

The nucleic acid molecules of the invention, such as those described above, can be identified and isolated using standard molecular biology techniques well known to the skilled person. The amplified DNA can be labeled (e.g., radiolabeled, fluorescently labeled) and used as a probe for screening a cDNA library derived from human cells. The cDNA can be derived from mRNA and contained in a suitable vector. Corresponding clones can be isolated, DNA obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

Antibodies

The invention also provides antibodies which bind to an epitope comprising either a variant amino acid sequence (e.g., comprising an amino acid substitution) encoded by a variant allele or a reference amino acid sequence encoded by the corresponding non-variant or wild-type allele. In certain embodiments, the amino acid sequence is an amino acid sequence of a human HNF4G protein. The term "antibody" as used herein refers to immunoglobulin molecules and immunologically active portions of immunoglobulin molecules, i.e., molecules that contain antigen-binding sites that specifically bind an antigen. A molecule that specifically binds to a polypeptide of the invention is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind to a polypeptide of the invention. The term "monoclonal antibody" or "monoclonal antibody composition", as used herein, refers to a population of antibody molecules that contain only one species of an antigen binding site capable of immunoreacting with a particular epitope of a polypeptide of the invention. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or a fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein, *Nature* 256:495-497 (1975), the human B cell hybridoma technique (Kozbor et al., *Immunol. Today* 4: 72 (1983)), the EBV-hybridoma technique (Cole et al., *Monoclonal Antibodies and Cancer Therapy*, Alan R. Liss, 1985, Inc., pp. 77-96) or trioma techniques. The technology for producing hybridomas is well known (see generally *Current Protocols in Immunology*

(1994) Coligan et al., (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in Immunology*, supra; Galfre et al., *Nature* 266:55052 (1977); R. H. Kenneth, in *Monoclonal Antibodies: A New Dimension In Biological Analyses*, Plenum Publishing Corp., New York, N.Y. (1980); and Lerner, *Yale J. Biol. Med.* 54:387-402 (1981)). Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., Bio/Technology 9: 1370-1372 (1991); Hay et al., *Hum. Antibod. Hybridomas* 3:81-85 (1992); Huse et al., *Science* 246: 1275-1281 (1989); and Griffiths et al., *EMBO J.* 12:725-734 (1993).

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

In general, antibodies of the invention (e.g., a monoclonal antibody) can be used to isolate a polypeptide of the invention by standard techniques, such as affinity chromatography or immunoprecipitation. A polypeptide-specific antibody can facilitate the purification of natural polypeptide from cells and of recombinantly produced polypeptide expressed in host cells. Moreover, an antibody specific for a polypeptide of the invention can be used to detect the polypeptide (e.g., in a cellular lysate, cell supernatant, or tissue sample) in order to evaluate the abundance and pattern of expression of the polypeptide. Antibodies can be used diagnostically to monitor protein levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies may also be useful in pharmacogenomic analysis. In such embodiments, antibodies against variant proteins encoded by nucleic acids according to the invention, such as variant proteins that are encoded by nucleic acids that contain at least one polymorpic marker of the invention, can be used to identify individuals that require modified treatment modalities.

Antibodies can furthermore be useful for assessing expression of variant proteins in disease states, such as in active stages of, or in an individual with a predisposition to a disease related to the function of the protein (e.g., HCCA2), in particular type 2 diabetes. Antibodies specific for a variant protein of the present invention that is encoded by a nucleic acid that comprises at least one polymorphic marker or haplotype as described herein can be used to screen for the presence of the variant protein, for example to screen for a predisposition to the disease state as indicated by the presence of the variant protein.

Antibodies can be used in other methods. Thus, antibodies are useful as diagnostic tools for evaluating proteins, such as variant proteins of the invention, in conjunction with analysis by electrophoretic mobility, isoelectric point, tryptic or other protease digest, or for use in other physical assays known to those skilled in the art. Antibodies may also be used in tissue typing. In one such embodiment, a specific variant protein has been correlated with expression in a specific tissue type, and antibodies specific for the variant protein can then be used to identify the specific tissue type.

Subcellular localization of proteins, including variant proteins, can also be determined using antibodies, and can be applied to assess aberrant subcellular localization of the protein in cells in various tissues. Such use can be applied in genetic testing, but also in monitoring a particular treatment modality. In the case where treatment is aimed at correcting the expression level or presence of the variant protein or aberrant tissue distribution or developmental expression of the variant protein, antibodies specific for the variant protein or fragments thereof can be used to monitor therapeutic efficacy.

Antibodies are further useful for inhibiting variant protein function, for example by blocking the binding of a variant protein to a binding molecule or partner. Such uses can also be applied in a therapeutic context in which treatment involves inhibiting a variant protein's function. An antibody can be for example be used to block or competitively inhibit binding, thereby modulating (i.e., agonizing or antagonizing) the activity of the protein. Antibodies can be prepared against specific protein fragments containing sites required for specific function or against an intact protein that is associated with a cell or cell membrane. For administration in vivo, an antibody may be linked with an additional therapeutic payload, such as radionuclide, an enzyme, an immunogenic epitope, or a cytotoxic agent, including bacterial toxins (diphtheria or plant toxins, such as ricin). The in vivo half-life of an antibody or a fragment thereof may be increased by pegylation through conjugation to polyethylene glycol.

The present invention further relates to kits for using antibodies in the methods described herein. This includes, but is not limited to, kits for detecting the presence of a variant protein in a test sample. One preferred embodiment comprises antibodies such as a labelled or labelable antibody and a compound or agent for detecting variant proteins in a biological sample, means for determining the amount or the presence and/or absence of variant protein in the sample, and means for comparing the amount of variant protein in the sample with a standard, as well as instructions for use of the kit.

The present invention will now be exemplified by the following non-limiting examples.

EXAMPLE 1

The effect of a susceptibility variant could depend on from which parent the variant is inherited. While many associations between sequence variants and human traits have been discovered recently through genome-wide association studies, the relevance of parental origin has largely been ignored as the information is usually unavailable. By combining the Icelandic genealogy with the method of long range phasing, we demonstrate here that for the approximately 40,000 individuals who have been genotyped using a SNP chip, the parental origins of most alleles can be determined. Using these results, we focused on SNPs that reside within 500 Kb of known imprinted genes and have been established to be associated with diseases. We have data to examine seven independent SNP associations, three with type 2 diabetes, and one each with breast cancer, basal cell carcinoma, prostate cancer and CAD. Five exhibit associations that differ depending on the parental origins of the alleles. The paternally inherited allele is dominant in two cases and the maternally inherited allele is dominant in the other three. These 5 variants are located in two regions of the genome, 11p15 and 7q32, each harbouring a cluster of imprinted genes, some paternally and some maternally expressed. Finally, a novel variant in the 11p15 region was found to exhibit a striking association to type 2 diabetes where the allele that confers risk when inherited paternally is protective if maternally transmitted, a genome-wide significant result that was further confirmed by a follow-up study.

Methods to Determine Parental Origin

The genome was covered with 6 cM long tiles, with 3 cM overlap between adjacent tiles. Each tile was then phased using LRP.

For a tile T and a proband P with a haplotype A over T, the numbers f(P,T,A) resp. m(P,T,A) were defined as the meiotic distance to the closest relative on the father resp. mother side having haplotype A, excluding all descendants of the parents. If no such relative could be found, the number was set to 10,000. Then the father origin score of A was defined as $$F(P,T,A) = (1 - 2^{-m(P,T,A)})/(1 - 2^{-f(P,T,A)}).$$

M(P,T,A) was defined in a corresponding way. Note that M(P,T,A)=1/F(P,T,A).

For every pair of overlapping tiles, the LRP phasing results for a proband P were stitched together if the two overlapping haplotype pairs were compatible in one way but not the other. In this way stretches of overlapping tiles were merged together into contigs for each proband.

For each contig formed in this way, say for proband P and consisting of the tiles $T_1, \ldots, T_n$, with compatible haplotypes $A=(A_1, \ldots, A_n)$ on one hand and $B=(B_1, \ldots, B_n)$ on the other hand, the parental origin orientation score was defined as the product $$[F(P,T_1,A_1)^* \ldots {}^*F(P,T_n,A_n)]^*[M(P,T_1,B_1)^* \ldots {}^*M(P,T_n,B_n)]$$

If this was >1, A was assigned to the father and B to the mother and vice versa if the result was <1.

Imprinted Regions and Disease Association

While many mechanisms can lead to parental-origin specific association with a phenotype, a priori sequence variants located in imprinted regions probably have the highest probability to exhibit such behaviour. Forty-nine genes have been firmly established to be imprinted. Including what are within 500 Kb of one of these genes amounts to approximately 31.4 Mb, which is approximately 1% of the genome and includes 4046 of the SNPs on the Illumina 317K chip.

By consulting the Catalogue of Published Genome-Wide Association studies, we identified the reported SNP-disease associations with $P<5\times10^{-8}$ and intersected that with the known imprinted regions. When further restricting to diseases for which we/deCode have published genome scans and hence have data to access parental-origin specific effects, 4 associations resulted. Three other associations we were aware of, one reported in a study of ours that is in press, and two established by a typed 2 diabetes consortium (DIAGRAM) that we are part of, were also included in this investigation.

Analyses and Results

For each disease-SNP association, five tests are performed (see Table 2). A standard case-control test that does not take parental origin into account was performed to provide a baseline. Then, a case-control analysis was performed separately for the paternally and maternally inherited allele. A two-degree of freedom test was applied to evaluate the joint effect of the paternally and maternally inherited alleles. Here a multiplicative model was assumed for the two alleles under the alternative hypothesis, but the magnitude and direction of the effect was allowed to differ depending on parental origin. Finally, the difference between the effects of the paternally and maternally inherited alleles was directly tested by comparing the counts of the two types of heterozygous within cases.

Breast Cancer

Figure 2:
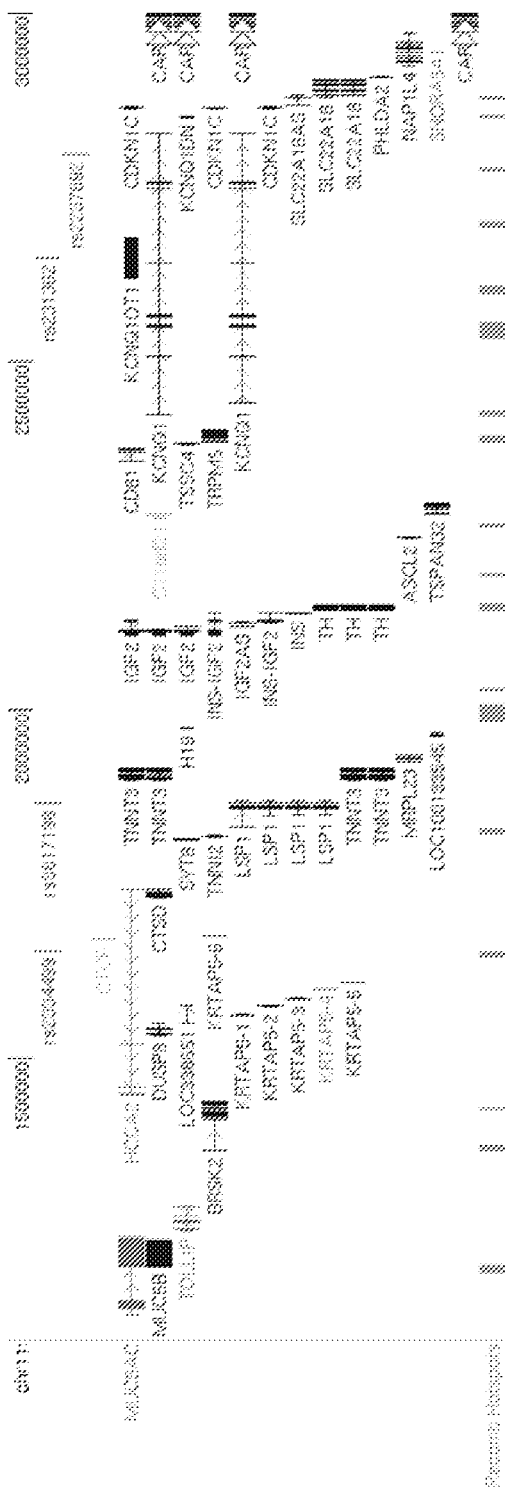
FIG. 2 shows a diagram of the chromosome 11p15 locus, illustrating the position of the markers rs2334499, rs3817198, rs231362 and rs2237892 relative to genes in the region.

Allele C of rs3817198 in the 11p15 region (FIG. 2) was reported by Easton et al (Nature 2007) to be associated with breast cancer with an allelic OR of 1.07 ($P=3\times10^{-9}$). This was a very large study that included about 20,000 cases and was the reason that such a modest effect could achieve genome-wide significance. Indeed, a study of CGEMS (Thomas et al, Nature Genetics 2009) with about 10,000 cases reported only ORs of 1.02 and 1.12 for heterozygous and homozygous carriers respectively, and a P of 0.06. In our data (Table 2), the standard case-control test gave a non-significant OR of 1.03 (P=0.42). However, when parental origin was taken into account, the paternally inherited allele showed a significant association (OR=1.16, P=0.0061). The 2-df test and the direct test of parental-origin specific effects were even more significant. Interesting, the estimated effect of the maternally inherited allele, while not significant (P=0.095), was in the opposite direction, a point we would return to later.

Type 2 Diabetes

Allele C of rs2237982 in the maternally expressed gene KCNQ1 was first observed to be associated to type 2 diabetes for individuals of Asian descent. The power to detect association in Caucasian populations is reduced because of the high frequency of the variant (~93%) there, but the association has nonetheless been conclusively replicated now. In the samples we have previously employed in genome-scans (Table 2) that include 1465 cases, none of the tests was significant. But when an extra list of diabetes patients was obtained, mainly motivated by the study of a novel variant (see below), an extra 795 cases were added, giving a total of 2260 cases. In the combined set, allele C was significantly associated with the disease (OR=1.26, P=0.018) when maternally transmitted, while the result for the paternally inherited allele was flat (OR=1.01, P=0.96).

Through a meta-analysis of diabetes genome-wide scans with addition follow-up (DIAGRAM), allele C of rs231362 was shown to be associated with the disease (OR=1.08, P=3×$10^{-13}$). In our combined sample, the standard test gave an OR of 1.10 (P=0.0092). The effect, however, appears to be limited to the maternally inherited allele (OR=1.21, P=1.0×$10^{-4}$). Like rs2237982, rs231362 is located in KNCQ1 (see FIG. 2) even though the two SNPs are not substantially correlated.

Another association with type 2 diabetes established by the DIAGRAM consortium is allele C of rs4731702 at 7q32. In our combined set, the association is again restricted to the maternally inherited allele (OR=1.18, P=5.8×$10^{-4}$), while the association to the paternally inherited allele is flat (OR=1.00, P=0.94).

Basal Cell Carcinoma

Figure 3:
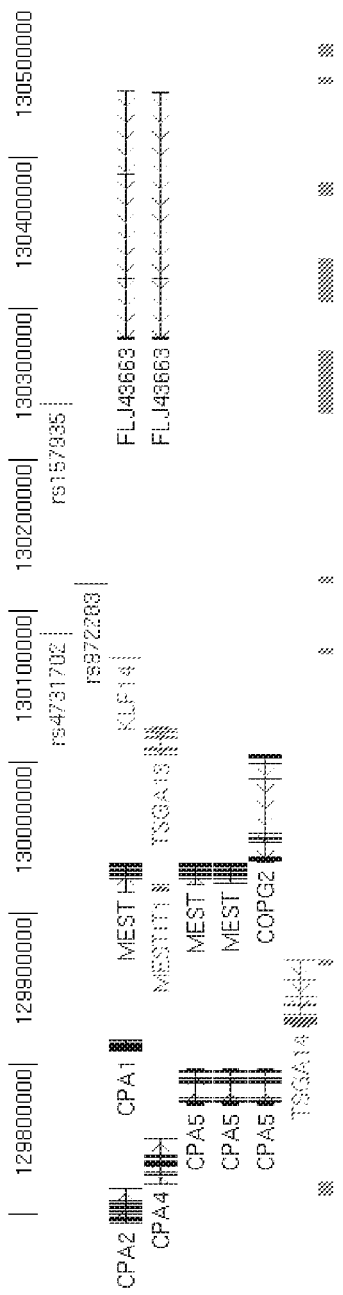
FIG. 3 shows a diagram of the chromosome 7q32 region.

Through a genome scan with follow-up, we found that allele T of rs157935, like rs231362 above also located at 7q32 (see FIG. 3), is associated with basal cell carcinoma (OR=1.23, P=5.7×$10^{-10}$. When examining our samples with genome-wide data and for which we could determine parental origins, we observed that the paternally inherited allele was significantly associated with the disease (OR=1.40, P=1.5×$10^{-6}$), but the effect of maternally inherited allele, while in the same direction, was not significant (OR=1.09, P=0.19). When tested directly, the effects of the paternally and maternally inherited alleles were significantly different (P=0.010).

A Novel Susceptibility Variant for Type 2 Diabetes

Even though our original focus was on sequence variants that were both in imprinted regions and have been established to be disease associated, the need to adjust for relatedness of the studied individuals using the method of genomic control led us to perform genome scans when studying effects of parental origin. From the type 2 diabetes genome scan performed with the original/discovery cohort, we observed a very striking result (see Table 3). Allele T of rs2334499, which is also located at 11q15 and close to breast cancer associated SNP rs3817198 (FIG. 2), showed a weak association with the disease (OR=1.12, P=0.012) in the standard case-control test, a result that would not be considered as interesting in the context of a genome scan. However, when parental origin is taking into account, both the paternally inherited allele (OR=1.42, P=4.1×$10^{-9}$) and the 2-df of freedom test (P=1.3×$10^{-8}$) are genome-wide significant. Even more interesting is that the maternally inherited allele also showed nominally significant association to the disease, but the effect is in the opposite direction (OR=0.87, P=0.029). When tested directly, the difference between the effects of the paternally and maternally inherited alleles was also genome-wide significant (P=1.3×$10^{-8}$). We note that this SNP falls within the established imprinted regions as defined, so in theory a genome-wide adjustment is not necessary and what is required is a Bonferonni adjustment factor of 4046, the number of SNPs on the Illumina 317K chip that are in the imprinted regions. Still, while the support for a parental-origin specific association between the SNP and the disease was very strong, the observation that the maternally inherited allele has an effect that is not just flat, but in the opposite direction to that of the paternally inherited allele, required replication. For this purpose, we obtained a new list of type 2 diabetes patients which added 795 cases to the study. All tests involving parental origin were replicated with significance. Combined, the paternally inherited allele has an OR of 1.35 (P=2.7×$10^{-10}$) and the maternally inherited allele has an OR of 0.87 (P=0.0038). The 2-df test and the test of difference in effects are even more significant than the test of the paternally inherited allele, giving P of 1.8×$10^{-10}$ and 5.5×$10^{-11}$ respectively.

It is interesting to note that the rs2334499 and the breast cancer associated SNP rs3817198 are not that far from each other, separated by about 200 kb, and both exhibit a strong effect with the paternally inherited allele, and a weaker effect for the maternally inherited allele in the opposite direction. While, with rs3817198, the effect of the maternally inherited allele is currently not significant, further investigation is warranted.

The associated region is within the first intron of HCCA2, a gene spanning 300 kb including several other genes. HCCA2 was initially identified as a hepatocellular carcinoma specific protein and has been shown to be involved in cell cycle regulation (Li et al. Mol Cell Biochem (2007) 304:297-304). The span of HCCA2 includes a cluster of keratin associated proteins (KRTAP5-1-5) as well as the DUSP8 gene, encoding dual specificity phosphatase 8. Intron 1 of HCCA2 further contains the CTSD gene encoding cathepsin D an intracellular aspartic protease involved in lysosomal degradation of insulin (Authier et al. J Biol. Chem. 2002 Mar. 15; 277(11):9437-46).

The associated marker is located 300 kb telomeric to the well documented imprinted region on chromosome 11p15.5 in a region that has not been previously shown to be imprinted. Based on the biallelic expression of genes immediately downstream of H19 in fetal and adult tissues, the telomeric border of the imprinted region is predicted to reside immediately downstream of H19 (Goldberg et al Hum Genet. 2003; 112). However, since functional imprinting is extremely tissue specific, imprinting cannot be excluded based on expression analysis. Recent studies using prediction models of imprinted genes predicted the murine but not the human CTSD gene to be paternally expressed, indicating that there are sequence characteristics in the region that are consistent with imprinting in the mouse (Luedi et al. Genome Res. 2005 June; 15(6):875-84; Luedi et al 2007). Allele specific expression analysis showed nominally significant excess of paternal expression of the CTSD gene in RNA isolated from whole blood.

CTCF Binding Site

Figure 4:
FIG. 4 shows the relative position of the CTCF motif on chromosome 11p15 with respect to rs2334499.

Insulators are DNA elements that affect gene expression by preventing activation of unrelated promoters by transcriptional enhancers. In vertebrates, the CCCTC-binding factor (CTCF) is the only known major insulator binding protein (Bell et al 1999). The insulator function of CTCF has been implicated in X chromosome inactivation (Filippova et al 2005) as well as regulation of expression at the imprinted Igf2/H19 locus on chromosome 11p15 (Bell and Felsenfeld, 2000). Seven tandem CTCF binding sites have been mapped to the human H19/IGF2 imprinting control region while four sites have identified at the mouse locus, where they have been shown to be important for maintenance of differential methylation (Schoenherr et al 2003). Recent studies have mapped regions of CTCF binding genome-wide (Kim et al 2007; Cuddapah et al 2009). One of the regions identified is located 17 kb centromeric to rs2334499, containing two binding motives (FIG. 4). Boundaries between a fully methylated and a fully unmethylated status have recently been mapped to 300 bp within this 2 kb binding region in human embryonic stem cells (Brunner A L, Genome Research. 2009). We analysed the methylation status of this CTCF binding region in DNA samples derived from whole blood, using bisulfite sequencing. In concordance with previous data we found conversion from unmethylated to methylated status within the binding region. At the boundaries we further found a partially methylated region of 180 bp including seven CpG dinucleotides (FIG. 4). The C/T ratio of those CpGs varied from from low to high methylation with two CpGs in particular showing around 50% methylation, consistent with one chromosome being methylated, a hallmark of imprinting. Curiously, there were clear individual differences in C/T ratio for these two CpGs. The estimated C/T ratio was correlated with the genotypes of SNPs from a 500 kb surrounding region. The most significant correlation was observed between methylation status at both CpGs and rs2334499, $r^2$=0.21; p=1.7E-09 and $r^2$=0.18, p=4.0E-08 for the two CpGs respectively, where the presence of the T allele correlated with higher level of methylation.

We have shown that rs2334499 T is correlated with increased methylation of differentially methylated CpGs at a CTCF binding site. This correlation is independent of parent of origin of the T allele. Given the well established role of CTCF in imprinting regulation that has been studied extensively at the nearby H19/IGF2 locus, and the differential methylation demonstrated here, we propose that this site is in fact an imprinting control region. The following model could account for the opposite effect of the T allele on risk of T2D, dependent on parent of origin. The model assumes that monoallelic expression of hitherto unidentified genes is dependent on hypomethylation of the paternal allele and hypermethylation of the maternal allele at this proposed imprinting control region. When the T allele is on the maternal chromosome, methylation of the already methylated maternal chromosome is enhanced while the paternally transmitted T allele increases methylation of the hypomethylated paternal allele. The paternally and maternally transmitted alleles would thereby affect monoallelic expression of the regulated genes in very different ways.

Structural Polymorphism at 11p15

Figure 5:
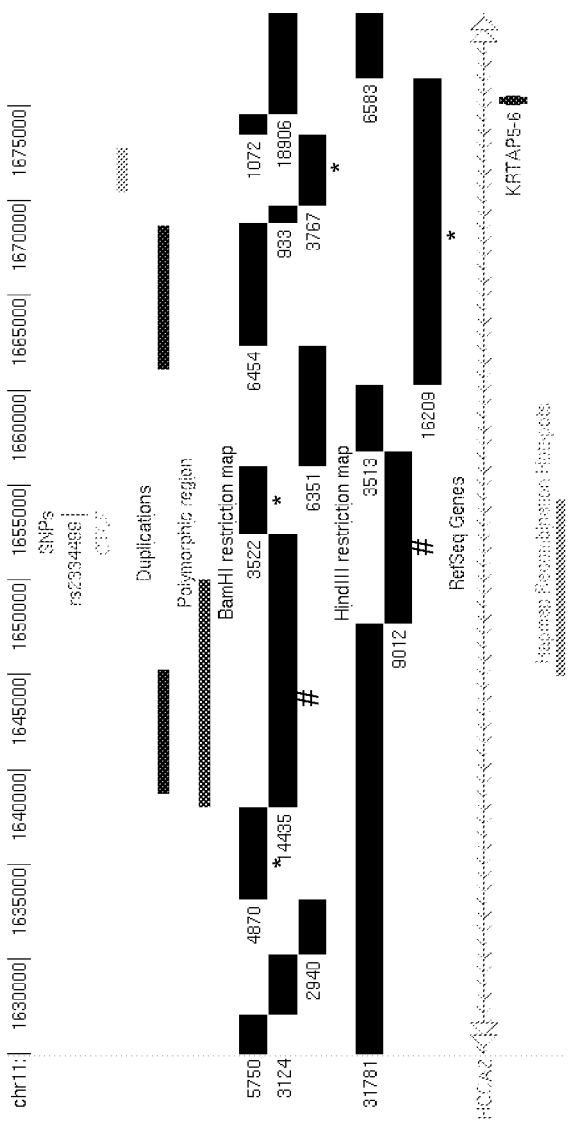
FIG. 5 shows the position on chromosome 11p15 containing a structural polymorphism, and its relationship to rs2334499, the CTCF motif, duplications in the region, and BamHI and HindIII restriction maps (upper half); and a restriction fragment illustrating the polymorphism in 24 individuals (lower half).

The associated marker rs2334499 is located in a 16 kb sequence that is flanked by a 6.5 kb inverted repeat (FIG. 5). Orientation of repetitive elements is an important predictor of imprinting (Luedi et al 2005) so we decided to analyse the region by Southern blotting looking for evidence of an inversion or other structural polymorphisms that might be correlated with the SNP. While no clear evidence of an inversion was found, a structural polymorphism was detected in the region around the telomeric repeat. Restriction mapping narrowed the polymorphic region down to a sequence predicted to be 12 kb between a BamHI site at 1.638 Mb and an EcoRI site at 1.65 Mb (FIG. 5). A HindIII fragment predicted to be 9 kb, partially overlapping this region, was found to be polymorphic, showing six different alleles, ranging from approximately 9 to 20 kb. Based on analysis of 8 HapMap CEU triads and around 500 SNPs in the region, the presence of the second largest fragment was most strongly correlated with the T allele of rs2334499 ($r^2$=0.55).

Parent of Origin Specific Expression

Monoallelic expression of imprinted genes may only occur at specific stages in development and/or in a certain tissue. Experimental detection of imprinted genes is therefore a non-trivial task. We tested several genes at the 11p15 locus for evidence of parent of origin effect on expression in whole blood and adipose tissue. Expression of HCCA2 and DUSP8 showed no evidence of parent of origin specific differences. The results for CTSD were nominally significant for excess of paternal expression. Clear evidence for parent of origin effect on expression was seen for the known imprinted IGF2, KCNQ1 and KCNQ1OT1 genes in blood and adipose tissue. Significantly higher expression is observed for IGF2 from the paternal chromosome, consistent with imprinting of the maternal chromosome. At the KCNQ1 locus an excess of the paternal allele of the KCNQ1OT1 RNA transcript was observed while the converse was seen for the KCNQ1 transcript.

TABLE 2

Parental Origin Specific Analyses of Known Disease Susceptibility Variants

| Seq ID NO | Disease, SNP [Alleles] Position B36 N (Case Sample Size) | (M) Con. Freq. | Regular case-control test | | Tests of association with parental origins | | | | | | |
|---|---|---|---|---|---|---|---|---|---|---|---|
| | | | | | Paternal Allele | | Maternal Allele | | 2-df | P. vs M. (case only) | |
| | | | OR | P | OR | P | OR | P | test P | n12:n21 | P |
| 5 | Breast Cancer rs3817198 [C/T] C11 1,865,582 (1900) | (35005) 0.302 | 1.03 | 0.42 | 1.16 | 0.0061 | 0.91 | 0.095 | 0.0031 | 433:438 | $7.1 \times 10^{-4}$ |
| 2 | T2D, rs2237892 [C/T] C11 2,796,327 | (32576) | | | | | | | | | |
| | Discovery (1465) | 0.926 | 1.16 | 0.086 | 1.11 | 0.35 | 1.21 | 0.11 | 0.17 | 81:90 | 0.51 |
| | Replication (795) | | 1.05 | 0.63 | 0.84 | 0.21 | 1.39 | 0.038 | 0.045 | 35:59 | 0.014 |
| | Combined (2260) | | 1.12 | 0.11 | 1.01 | 0.96 | 1.26 | 0.018 | 0.043 | 116:149 | 0.053 |
| 3 | T2D, rs231362 [C/T] C11 2,648,047 | (30098) | | | | | | | | | |
| | Discovery (1460) | 0.551 | 1.10 | 0.033 | 0.99 | 0.85 | 1.22 | 0.0010 | 0.0076 | 315:378 | 0.021 |
| | Replication (778) | | 1.10 | 0.082 | 1.01 | 0.92 | 1.20 | 0.020 | 0.088 | 155:180 | 0.18 |
| | Combined (2238) | | 1.10 | 0.0092 | 0.99 | 0.92 | 1.21 | $1.0 \times 10^{-4}$ | 0.0010 | 470:558 | 0.0083 |
| 4 | T2D, rs4731702 [C/T] C7 130,083,924 | (32576) | | | | | | | | | |
| | Discovery (1463) | 0.438 | 1.16 | $5.7 \times 10^{-4}$ | 1.09 | 0.14 | 1.24 | $3.2 \times 10^{-4}$ | $6.1 \times 10^{-4}$ | 330:371 | 0.15 |
| | Replication (794) | | 0.96 | 0.48 | 0.86 | 0.040 | 1.08 | 0.29 | 0.088 | 163:204 | 0.037 |
| | Combined (2257) | | 1.09 | 0.017 | 1.00 | 0.94 | 1.18 | $5.8 \times 10^{-4}$ | 0.0034 | 493:575 | 0.018 |

TABLE 2-continued

Parental Origin Specific Analyses of Known Disease Susceptibility Variants

| Seq ID NO | Disease, SNP [Alleles] Position B36 N (Case Sample Size) | (M) Con. Freq. | Regular case-control test OR | P | Tests of association with parental origins | | | | | 2-df test P | P. vs M. (case only) n12:n21 | P |
|---|---|---|---|---|---|---|---|---|---|---|---|---|
| | | | | | Paternal Allele OR | P | Maternal Allele OR | P | | | | |
| 6 | Basal Cell Carcinoma rs157935 [T/G] C7 130,236,093 (1118) | (37258) 0.676 | 1.23 | $1.8 \times 10^{-5}$ | 1.40 | $1.5 \times 10^{-6}$ | 1.09 | 0.19 | | $3.3 \times 10^{-6}$ | 237:182 | 0.010 |

For each SNP, the first allele is the reported risk allele based on analyses that did not take into account parent of origin.
M is the size of the control set used and the frequency given is that of the risk allele in the controls. Individuals used in these analyses have all been typed using an Illumina chip.
Rs3817198 and rs231362 are not on the 317K Illumina chip. Additional single-track genotyping and imputation employing phased haplotypes of the neighboring SNPs were performed. The effect of the paternally inherited allele is tested by comparing the corresponding alleles in cases to those in controls. The effect of the maternally inherited allele was similarly tested.
The 2-df of freedom test assumes a multiplicative effect for the paternally and maternally inherited alleles, but allows the effects to be different under the alternative hypothesis when the null hypothesis of no effect is tested. To directly test whether the paternally and maternally inherited alleles have different effects, the counts of the two different types of heterozygous within cases were compared; n12 denotes the number of cases who have inherited allele 1 from the father and allele 2 from the mother, and n21 is the reverse. All tests have been adjusted for relatedness and potential stratification using the method of genomic control.

TABLE 3

A novel Type 2 Diabetes variant which exhibits effects in different directions depending of parental origin

| Seq ID NO | Disease, SNP [Alleles] Position B36 N (Case Sample Size) | (M) Con. Freq. | Regular case-control test OR | P | Tests of association with parental origins of the T allele | | | | 2-df test P | P. vs M. (case only) nTC:nCT | P |
|---|---|---|---|---|---|---|---|---|---|---|---|
| | | | | | Paternal effect OR | P | Maternal effect OR | P | | | |
| 1 | T2D, rs2334499 [T/C] C11 1,653,425 Discovery (1464) Replication (795) Combined (2259) | (32583) 0.411 | 1.12 1.03 1.09 | 0.012 0.55 0.021 | 1.42 1.24 1.35 | $4.1 \times 10^{-9}$ 0.0034 $2.7 \times 10^{-10}$ | 0.87 0.85 0.87 | 0.029 0.035 0.0038 | $1.3 \times 10^{-8}$ 0.0031 $1.8 \times 10^{-10}$ | 433:275 222:157 655:432 | $1.1 \times 10^{-8}$ $8.2 \times 10^{-4}$ $5.5 \times 10^{-11}$ |

EXAMPLE 2

An association analysis was performed for markers identified in the 1000 genomes project as correlated markers with rs2334499. This was done by imputation of genotypes for Icelandic glaucoma cases based on the 1000 genomes data.

Determination of the parental origin of alleles was performed as described in the above.

Results of the association analysis is shown in Table 4. As expected, almost all of the markers do show significant association with type 2 diabetes, with paternal origin of the effect allele being indicative of increased risk of type 2 diabetes, while a maternal origin of the effect allele being protective. The strength of the observed association in general is correlated with the strength of the LD between the particular marker and rs2334499.

TABLE 4

Association to type 2 diabetes for surrogate markers of rs2334499. The data is imputation of Icelandic T2D cases using the 1000G dataset for those SNP in LD ($r^2 > 0.2$) with rs2334499. Shown is marker name, position in NCBI Build 36, allelic identity, $R^2$ values, number of controls and cases and frequencies of the risk allele in controls and T2D cases respectively, odds ratio (OR) and P-value of association with T2D based for standard case-control analysis, and for analysis of particular parental origin of the effect allele, and finally position of the marker in SEQ ID NO: 7.

| SNP | Pos | Allele Other | Effect | $R^2$ | Controls n | Frq | T2D Cases n | Frq | Standard test OR | P-value | Paternal allele OR | P-value | Maternal allele OR | P-value | Pos in Seq ID No 7 |
|---|---|---|---|---|---|---|---|---|---|---|---|---|---|---|---|
| s.1625734 | 1625734 | A | G | 0.22 | 34598 | 0.012 | 2241 | 0.012 | 1.017 | 0.96 | 0.985 | 0.97 | 1.052 | 0.92 | 301 |
| rs1038727 | 1637577 | C | T | 0.20 | 34706 | 0.798 | 2251 | 0.802 | 0.979 | 0.62 | 1.086 | 0.15 | 0.876 | 0.031 | 12144 |
| s.1643366 | 1643366 | C | A | 0.21 | 34598 | 0.780 | 2241 | 0.780 | 0.999 | 0.98 | 1.097 | 0.14 | 0.951 | 0.13 | 17933 |
| rs28526166 | 1643383 | A | G | 0.30 | 34598 | 0.537 | 2241 | 0.550 | 1.058 | 0.12 | 1.175 | 0.0011 | 0.956 | 0.36 | 17950 |
| rs7131362 | 1645901 | A | G | 0.33 | 34706 | 0.566 | 2251 | 0.580 | 1.061 | 0.096 | 1.174 | 0.00086 | 0.962 | 0.42 | 20468 |
| rs12360952 | 1647463 | T | C | 0.30 | 34598 | 0.716 | 2241 | 0.723 | 1.040 | 0.38 | 1.196 | 0.003 | 0.910 | 0.1 | 22030 |
| rs7112918 | 1647545 | T | C | 0.37 | 34598 | 0.461 | 2241 | 0.484 | 1.105 | 0.007 | 1.208 | 0.00016 | 1.013 | 0.8 | 22112 |
| s.1648379 | 1648379 | T | C | 0.38 | 34598 | 0.071 | 2241 | 0.069 | 0.921 | 0.44 | 1.119 | 0.41 | 0.735 | 0.044 | 22946 |
| s.1649074 | 1649074 | G | C | 0.69 | 34598 | 0.383 | 2241 | 0.402 | 1.093 | 0.02 | 1.359 | 1.43E−09 | 0.875 | 0.011 | 23641 |
| rs12283736 | 1651997 | T | A | 0.93 | 34598 | 0.407 | 2241 | 0.425 | 1.079 | 0.036 | 1.331 | 4.41E−09 | 0.872 | 0.0064 | 26564 |
| rs748541 | 1652592 | G | A | 0.30 | 34598 | 0.656 | 2241 | 0.670 | 1.072 | 0.086 | 1.213 | 0.0005 | 0.953 | 0.37 | 27159 |
| rs10838695 | 1653790 | C | A | 0.25 | 34598 | 0.245 | 2241 | 0.238 | 1.041 | 0.38 | 1.264 | 0.00024 | 0.869 | 0.018 | 28357 |
| rs10769275 | 1655721 | T | C | 0.27 | 34598 | 0.723 | 2241 | 0.735 | 1.078 | 0.094 | 1.190 | 0.0049 | 0.983 | 0.77 | 30288 |
| s.1657176 | 1657176 | T | C | 0.22 | 34598 | 0.200 | 2241 | 0.196 | 1.031 | 0.5 | 1.255 | 0.00066 | 0.863 | 0.016 | 31743 |
| rs4752779 | 1658046 | T | G | 0.25 | 34706 | 0.629 | 2251 | 0.639 | 1.047 | 0.22 | 1.212 | 0.00019 | 0.912 | 0.063 | 32613 |

TABLE 4-continued

Association to type 2 diabetes for surrogate markers of rs2334499. The data is imputation of Icelandic T2D cases using the 1000G dataset for those SNP in LD ($r^2 > 0.2$) with rs2334499. Shown is marker name, position in NCBI Build 36, allelic identity, $R^2$ values, number of controls and cases and frequencies of the risk allele in controls and T2D cases respectively, odds ratio (OR) and P-value of association with T2D based for standard case-control analysis, and for analysis of particular parental origin of the effect allele, and finally position of the marker in SEQ ID NO: 7.

| SNP | Pos | Allele Other | Allele Effect | $R^2$ | Controls n | Controls Frq | T2D Cases n | T2D Cases Frq | Standard test OR | Standard test P-value | Paternal allele OR | Paternal allele P-value | Maternal allele OR | Maternal allele P-value | Pos in Seq ID No 7 |
|---|---|---|---|---|---|---|---|---|---|---|---|---|---|---|---|
| rs4752780 | 1658460 | G | C | 0.82 | 34598 | 0.439 | 2241 | 0.453 | 1.067 | 0.086 | 1.307 | 1.30E−07 | 0.870 | 0.0071 | 33027 |
| rs4752781 | 1658631 | A | T | 0.82 | 34706 | 0.412 | 2251 | 0.428 | 1.068 | 0.066 | 1.342 | 1.01E−09 | 0.848 | 0.00091 | 33198 |
| s.1659505 | 1659505 | G | A | 0.82 | 34598 | 0.456 | 2241 | 0.471 | 1.080 | 0.051 | 1.313 | 2.87E−07 | 0.889 | 0.028 | 34072 |
| rs4417225 | 1660140 | C | T | 0.82 | 34598 | 0.456 | 2241 | 0.471 | 1.080 | 0.051 | 1.313 | 3.08E−07 | 0.889 | 0.029 | 34707 |
| s.1662049 | 1662049 | C | T | 0.79 | 34598 | 0.457 | 2241 | 0.472 | 1.080 | 0.052 | 1.312 | 3.46E−07 | 0.889 | 0.029 | 36616 |
| s.1662089 | 1662089 | G | C | 0.32 | 34598 | 0.653 | 2241 | 0.667 | 1.085 | 0.055 | 1.295 | 9.86E−06 | 0.917 | 0.12 | 36656 |
| s.1662163 | 1662163 | G | A | 0.82 | 34598 | 0.457 | 2241 | 0.472 | 1.080 | 0.052 | 1.312 | 3.49E−07 | 0.889 | 0.029 | 36730 |
| s.1662228 | 1662228 | A | G | 0.64 | 34598 | 0.631 | 2241 | 0.642 | 1.062 | 0.15 | 1.244 | 0.00014 | 0.913 | 0.099 | 36795 |
| s.1662252 | 1662252 | T | C | 0.27 | 34598 | 0.757 | 2241 | 0.770 | 1.088 | 0.073 | 1.182 | 0.0095 | 1.007 | 0.92 | 36819 |
| s.1663159 | 1663159 | G | T | 0.82 | 34598 | 0.345 | 2241 | 0.364 | 1.116 | 0.0079 | 1.375 | 6.91E−09 | 0.902 | 0.072 | 37726 |
| s.1663161 | 1663161 | C | T | 0.82 | 34598 | 0.345 | 2241 | 0.364 | 1.116 | 0.0079 | 1.375 | 6.91E−09 | 0.902 | 0.072 | 37728 |
| rs7102894 | 1663514 | G | C | 0.82 | 34598 | 0.461 | 2241 | 0.478 | 1.087 | 0.036 | 1.326 | 1.19E−07 | 0.892 | 0.033 | 38081 |
| s.1663762 | 1663762 | C | T | 0.75 | 34598 | 0.471 | 2241 | 0.487 | 1.084 | 0.037 | 1.321 | 1.12E−07 | 0.891 | 0.028 | 38329 |
| s.1667464 | 1667464 | C | T | 0.75 | 34598 | 0.436 | 2241 | 0.451 | 1.078 | 0.058 | 1.334 | 6.94E−08 | 0.871 | 0.011 | 42031 |
| s.1667475 | 1667475 | C | G | 0.75 | 34598 | 0.462 | 2241 | 0.479 | 1.087 | 0.036 | 1.326 | 1.49E−07 | 0.892 | 0.035 | 42042 |
| s.1667517 | 1667517 | A | T | 0.79 | 34598 | 0.462 | 2241 | 0.479 | 1.087 | 0.036 | 1.326 | 1.49E−07 | 0.892 | 0.035 | 42084 |
| s.1668164 | 1668164 | C | G | 0.75 | 34598 | 0.472 | 2241 | 0.488 | 1.084 | 0.039 | 1.321 | 1.39E−07 | 0.891 | 0.029 | 42731 |
| rs35944603 | 1668394 | G | C | 0.28 | 34598 | 0.620 | 2241 | 0.627 | 1.036 | 0.39 | 1.154 | 0.0098 | 0.933 | 0.21 | 42961 |
| s.1669681 | 1669681 | G | A | 0.28 | 34598 | 0.620 | 2241 | 0.627 | 1.036 | 0.39 | 1.153 | 0.01 | 0.934 | 0.21 | 44248 |
| s.1669874 | 1669874 | C | T | 0.28 | 34598 | 0.620 | 2241 | 0.627 | 1.036 | 0.39 | 1.153 | 0.01 | 0.934 | 0.21 | 44441 |
| s.1669942 | 1669942 | G | A | 0.41 | 34598 | 0.738 | 2241 | 0.738 | 0.999 | 0.99 | 1.277 | 8.83E−05 | 0.762 | 7.49E−05 | 44509 |
| s.1670552 | 1670552 | C | T | 0.79 | 34598 | 0.463 | 2241 | 0.479 | 1.086 | 0.039 | 1.325 | 2.02E−07 | 0.892 | 0.035 | 45119 |
| rs10769560 | 1670637 | A | G | 0.28 | 34706 | 0.585 | 2251 | 0.591 | 1.027 | 0.47 | 1.167 | 0.0021 | 0.907 | 0.048 | 45204 |
| rs17245346 | 1671223 | C | T | 0.69 | 34598 | 0.508 | 2241 | 0.520 | 1.070 | 0.097 | 1.295 | 3.34E−06 | 0.887 | 0.031 | 45790 |
| rs11607954 | 1671264 | T | C | 0.51 | 34706 | 0.529 | 2251 | 0.537 | 1.035 | 0.35 | 1.209 | 0.00012 | 0.889 | 0.016 | 45831 |
| rs10839220 | 1671312 | A | C | 0.45 | 34706 | 0.474 | 2251 | 0.484 | 1.041 | 0.26 | 1.255 | 3.89E−06 | 0.865 | 0.0034 | 45879 |
| rs11600502 | 1671560 | G | A | 0.18 | 34706 | 0.526 | 2251 | 0.534 | 1.033 | 0.37 | 1.138 | 0.0093 | 0.941 | 0.22 | 46127 |
| s.1671908 | 1671908 | T | C | 0.35 | 34598 | 0.424 | 2241 | 0.436 | 1.075 | 0.087 | 1.280 | 1.36E−05 | 0.902 | 0.074 | 46475 |

The invention claimed is:

1. A method of determining a susceptibility to type 2 diabetes in a human individual, the method comprising:

analyzing nucleic acid from a biological sample obtained from the individual with respect to the identity of at least one allele of at least one polymorphic marker, using a method that comprises at least one nucleic acid analysis technique selected from:

analysis using a whole genome SNP chip, single-stranded conformational polymorphism (SSCP) assay, restriction fragment length polymorphism (RFLP), automated fluorescent sequencing; clamped denaturing gel electrophoresis (CDGE);

denaturing gradient gel electrophoresis (DGGE), mobility shift analysis, restriction enzyme analysis, heteroduplex analysis, chemical mismatch cleavage (CMC), RNase protection assays, use of polypeptides that recognize nucleotide mismatches, allele-specific PCR, sequence analysis, and SNP genotyping, determining parental origin of the at least one allele of the at least one polymorphic marker, wherein different parental origins of the at least one allele are associated with different susceptibilities to type 2 diabetes in humans, and wherein the at least one polymorphic marker is selected from the group consisting of rs2334499, and markers in linkage disequilibrium therewith, wherein the linkage disequilibrium is characterized by a value for $r^2$ of at least 0.2, and determining a susceptibility to type 2 diabetes for the individual from the nucleic acid analysis and from the parental origin of said at least one allele, wherein a paternal origin at-risk T allele of rs2334499 or a marker allele in linkage disequilibrium therewith is determined to be present in the nucleic acid, and the step of determining a susceptibility to type 2 diabetes for the individual includes calculating a risk score that includes a relative risk (RR) or odds ratio (OR) of at least 1.1 attributed to the paternal origin at-risk allele being present in the nucleic acid; or wherein a maternal origin protective T allele of rs2334499 or a marker allele in linkage disequilibrium therewith is determined to be present in the nucleic acid, and the step of determining susceptibility to type 2 diabetes for the individual includes calculating a risk score that includes a RR or OR of less than 0.9 attributed to the maternal origin protective allele being present in the nucleic acid; and wherein the presence of a paternal origin at-risk allele for the at least one marker in the nucleic acid is indicative of an increased susceptibility to type 2 diabetes for the individual, and the presence of a maternal origin protective allele for the at least one marker in the nucleic acid is indicative of a decreased susceptibility to type 2 diabetes for the individual.

2. The method of claim 1, comprising:
analyzing the nucleic acid to identify both alleles of the at least one polymorphic marker, and
determining parental origin of both alleles of the at least one polymorphic marker, and
determining a susceptibility to type 2 diabetes based on the identity and the parental origin of both alleles of the at least one polymorphic marker.

3. The method of claim 1, wherein the at least one polymorphic marker is selected from the group consisting of rs2334499, rs1038727, rs7131362, rs748541, rs4752779, rs4752780, rs4752781, rs4417225, rs10769560, rs17245346, rs11607954, rs10839220, rs11600502, s.1625734, s.1638067, s.1638081, s.1643366, rs28526166, rs7109305, rs12360952, rs7112918, s.1648379, s.1648786, s.1648802, s.1649074, s.1650392, rs12283736, rs10838695, rs10769275, s.1657176, s.1659505, s.1660547, s.1662049, s.1662089, s.1662163, s.1662228, s.1662252, s.1663159, s.1663161, rs7102894, s.1663762, s.1664515, s.1664655, s.1667464, s.1667475, s.1667517, s.1668164, rs35944603, s.1669681, s.1669874, s.1669942, s.1670552, and s.1671908.

4. The method of claim 2, wherein a paternal origin at-risk T allele of rs2334499 or a marker allele in linkage disequilibrium therewith, is determined to be present in the biological sample, and the step of determining a susceptibility to type 2 diabetes for the individual includes calculating a risk score that includes a relative risk (RR) or odds ratio (OR) of at least 1.1 attributed to the paternal origin at-risk allele being present in the nucleic acid.

5. The method of claim 2, wherein a maternal origin protective T allele of rs2334499 or a marker allele in linkage disequilibrium therewith, is determined to be present in the biological sample, and the step of determining susceptibility to type 2 diabetes for the individual includes calculating a risk score that includes a relative risk (RR) or odds ratio (OR) of less than 0.9 attributed to the maternal origin protective allele being present in the nucleic acid.

6. The method of claim 2, further comprising determining whether at least one additional at-risk variant of type 2 diabetes is present in the individual.

7. The method of claim 6, wherein the at least one additional at-risk variant is selected from the group consisting of allele T of rs7903146, allele C of rs1801282, allele G of rs7756992, allele T of rs10811661, allele C of rs1111875, allele T of rs4402960, allele T of rs5219, allele C of rs9300039, allele A of rs8050136, allele C of rs13266634, allele T of rs7836388, allele A of rs11775310, allele C of rs1515018, allele C of rs1470579, and allele C of rs7754840.

8. The method of claim 6, wherein determination of the presence of the at least one additional at-risk variant of type 2 diabetes is based on analysis of a nucleic acid sample from the individual.

9. The method of claim 1, wherein the human individual is of an ancestry that includes European ancestry.

10. The method of claim 1, wherein the at least one allele of at least one polymorphic marker is allele T of polymorphic marker rs2334499.

11. The method of claim 10, further comprising obtaining a biological sample from the human individual prior to the analyzing.

12. The method of claim 10, wherein determining the susceptibility comprises comparing nucleic acid for the human individual obtained from the biological sample to a database containing correlation data between polymorphic markers, parental origin, and susceptibility to type 2 diabetes, wherein the polymorphic markers in the database include rs2334499.

13. The method of claim 12, wherein the database comprises at least one measure of susceptibility to type 2 diabetes for the polymorphic markers.

14. The method of claim 12, wherein the database comprises a look-up table containing at least one measure of susceptibility to type 2 diabetes for the polymorphic markers.

15. The method of claim 10, further comprising reporting the susceptibility to at least one third party selected from the group consisting of the human individual, a guardian of the human individual, a genetic service provider, a physician, a medical organization, and a medical insurer.

16. The method of claim 10, wherein the human individual has European ancestry.

* * * * *

SEQUENCE LISTING

<160> NUMBER OF SEQ ID NOS: 7

<210> SEQ ID NO 1
<211> LENGTH: 599
<212> TYPE: DNA
<213> ORGANISM: Homo sapiens

<400> SEQUENCE: 1

```
cacagaatag ttgacaataa caggaaggga aaatgcaagc caattgtatg tggactgaaa      60
gaaggctaca aaaggattaa aacattaagc cacaatgcag ctttctgaca gtcaaatgat     120
caacatacag aaatatattt tccaaccaca gggcaaaaaa aaaattagaa attaagtcac     180
aaaagggata gtgcaaatat tgtatgtttg gaaaccaaat agtctattac cataaatttg     240
gggttaaaga gataatcata attattaaaa agtaataaaa acattgcaca ttagaaggay     300
ggggcagagt gaagcagctg ttactgagag gtgtacggta ctaaatacat ttctcacaaa     360
ttatgaaatt ggatgtctac gcagatgttt tgcctgtttc taacggagct gttttttgtca    420 ttaattttt agttcctttt ccattctggg ttcaatcttt catcagtgat atggtttgca      480
aatacatcct ccagatctgc gacttatctt ccgatttctt gttagtgtct tttgaagcac     540
acatttgaaa aaaattcgat gaagttcacc ctatcaatgt tttattttac gatcttatt      599
```

<210> SEQ ID NO 2
<211> LENGTH: 599
<212> TYPE: DNA
<213> ORGANISM: Homo sapiens

<400> SEQUENCE: 2

```
cccaagagtg tgggggtcag gaatggcgtc cttgtgccct tgtcacccac tcctgtgggt    60
acacagcttc cctttctgca aagtcacacc ccaagccctg gcttgagcat gtacacaggc   120
tgcagcccgt gttcctggag ccaccgtccc aggtgtggca aaggccccca cagagtgtgc   180
atcctaaggt ggttcagagg tcctcagaaa gtgccaagag ccttcctca gaggaagagc    240
aagggtaggt gcctctggca tgagccagat gatgggagct gtcacaggac tttgccaccy   300
ggggtgaggg gcctagaaac ccctctccac cagatgcctt acacccccca tccccacacg   360
cacacagctt ggaggctgga agccccggga atgcggccca ccctgtctcc agttgttccc   420
taccagccca gctgctggtc cctaaccggg cccacctgtt gggtccttag caccagctgc   480
ccagagcccc cagcccctac cctagtctga tgacccaggc ctttcccct gcccaggcta    540
gccttgtgct cagctgccag cacagccccc accacacact ccccaacagg tgtctccac   599
```

<210> SEQ ID NO 3
<211> LENGTH: 599
<212> TYPE: DNA
<213> ORGANISM: Homo sapiens

<400> SEQUENCE: 3

```
cttcttgagg cttcaatttc cccttctgtg agctgggagg acaggcccac tagatgctct    60
ctgagggacc taccaaggat gtgggctgtg tgtctcagcc aacagcagta tctcctaacc   120
ccaacacaag aaatacacat agtaggtgtc tggttaatgc tcttggaatt tcagcctata   180
ctaaccatct gaaagccact gagtctgaac tctgctacca tatttgagat tatctctcca   240
ttgggcacct atgggttgcc tagagacaag ctaccatggt cctcttccct cgcccgtcay   300
gtgcagggtc aaaggcaggt gagctacaca gctcgccctg ctcttcactc tgctttaatg   360
tgggtgcttg ccttggcaga tgggcccgac agtgataaga acaaatgaca gatgcatact   420
ggggcacctg tgactgccat gagacacagt ccactgattc tgcctccaac cccctcccca   480
gagcagaata gtgagtgcta ggtttccgcc tgtacctcca cgggacccca acagctcctg   540
aaccccattc cgagatttga ggttgtgact tggggacctc tagacttccc ttccctcca   599
```

<210> SEQ ID NO 4
<211> LENGTH: 599
<212> TYPE: DNA
<213> ORGANISM: Homo sapiens

<400> SEQUENCE: 4

```
attaggagta gaaaggaatg tccttaattt tataaatgac atctacagaa aaacctacat    60
tgtacttaac agtgaaaaat gggatgattt tcacctaaga ttggaaataa gctaaggatg   120
ttcactctct cacttcaatt ctcagatatt attgtctatt aagaaaatcc caaggcatct   180
atccaaaagt tcatagaact aagaagtcat tttagtaagt tttcaaaata caaggtctgt   240
atactaacaa tgaatacata aaaatcaaaa ttaaaaaaca gcattatttc ccacacacay   300
cagttccatt tagcaccaaa aagataaata tttaatatat agttaacaaa attttcgtta   360
tctgtgtact aaaactaca aaagaccaat gaaagacagc atatacctaa ataaatggca   420
agtcttccat ggattggaag actcagtact gtgtagatgt catttctccc caaattgaca   480
tatagattcg aatggccgta atcaaaatcc aagtaggagt gtgactttg tagatattat    540
attttaaatt gacatggaaa gacaaactaa aataatcaaa acaattttgg aaaaaaact   599
```

<210> SEQ ID NO 5
<211> LENGTH: 599
<212> TYPE: DNA
<213> ORGANISM: Homo sapiens

<400> SEQUENCE: 5

```
accccatctg ggaagaggta taagtttgtg gccaccgggc atgggaagta tgagaaggtg      60
cttgtggaag ggggcccggc tccctaggcg tcccatctcg gtgagtccct ggcaactcac     120
agaaggggat gaggtgcaca cacgtgcact gtgctgggaa cttggcaacc tggaggctgc     180
ctggagccct gttgcaggct acaagggtgg actccgagtt ggccagaacc cagaccagct     240
cagtctccca gtcctgtgca gatgctgcct ctctcacctg ataccagatt caaactctcy     300
gctcatttca ctagagtcag cccggctcag ccactgctcc actagggaag ctcaaggctc     360
ccatctggga ctccccaaaa gccacagcag ggctcgtgag ggaagtgagg ggcagcctgg     420
ccaccacagg gctagcattg aaggaagcag gtggcatgga gcccaggttc cctgaccatc     480
tgtatgctga gggtccatag aggggcagga acttaggtcc tactccctgt cccagccgag     540
agcgattcag aggtcctgat gccctcccca tcccatgctg cagacagagc agtgccact      599
```

<210> SEQ ID NO 6
<211> LENGTH: 599
<212> TYPE: DNA
<213> ORGANISM: Homo sapiens

<400> SEQUENCE: 6

```
tgctactgca ctccagaagt ggaagtagcc accacacagc tgcacctgcc acctccttcc      60
ccactccagg gcctttgaaa tgtgctgctc tctctatgcc gagagctctc acccctaccc     120
cctgcaccca cacattcctg ctcatccctt agctgagacc ttggaaatca cctcctcagg     180
ggaccactgg gaagaaggtc cttttcatct gagtgccttc ccctcagggc atgattttc      240
ttgggccatt tttttggta tgtgtttact taggttccat gatgacagag accatgcctk     300
tgttttcatc actatcgtct tcacctcact gccaaccagt gcctggcaca cagtaggtgt     360
tcaagaaagt tttgctgaat aaatggatga acaatgacat cagcctactt tgacctcttg     420
agttcctctg atctctgaat gttctggagc aaggaccttt aacagcatct ccatctcttc     480
ctggccttgc cgccccaccc agtaaaaacca taatacttgc tggtatagcc tcttcctgca     540
aataaaagta tacaaggagt tcagaacgga cactccaaac aaagggattt atgaccttg      599
```

<210> SEQ ID NO 7
<211> LENGTH: 46775
<212> TYPE: DNA
<213> ORGANISM: Homo sapiens

<400> SEQUENCE: 7

```
ggctcacgcc tgtcatccca gcactttggg aggccgaggc gggcggatca cgaggtcagg      60
agattgagac cacggcgaaa ccccgtctct actaaaaata caaaaaatt aggtgggcgt     120
ggtggcgggc gcctgcaatc ccagctactc tggaggctga ggcaggagaa tcgcgtgaac     180
ccaggaggcg gagcttgcag tgagccgaga tggccccact gcacaccagc ctgggcgaca     240
gagcaagact ccgtctcaaa aaaaaaaaaa aaaaaaaaa aaaaagaaa agaaaagaaa      300
agaaaagaaa gaaagaaaa gaaagaaaa gaaagaaaa gaaagaaaa gaaggaaag cacgaaggaa     360
aatagcaaag ggtcccggtg ttgcacacac acaaagcagc agcagccgct ggaggtcttc     420
cgtgttttggt aaaggtggct acggactccc gcatggagac gcggcctgga gggtgtcact     480
```

-continued

| | | |
|---|---|---|
| gctctaggct gtctgcaggg cctctccgca gacctggacg gatttcagtg ggagactaga | 540 |
| gcgtcactta agatgtttga atgtaaaagc atcctgaatg atcatctttt agcttgagat | 600 |
| tttggctacc tttcaaacag acatagtttg acctttgcag tcctaggtaa tgcaggaatg | 660 |
| gcaaatgctc ctgaaggcgg ggaggcggcc cggcccgcac tgagcttctc accggccaga | 720 |
| gggcgcagcc acccggcctt cccgaagcag gacagcggcc tttccaagac cgcggagtcc | 780 |
| ccgtgaggga tggtgcctcc ggagcctggc atctcgggcg gatgagaagc tgagcgcggt | 840 |
| cagatggccc gcagggtccc actgcgggcc gagccctggc tgggggacag tttgggggga | 900 |
| agcagcagct gcctcagttt acagtggcag ccggaggagg acctgggcag tggcgagtgt | 960 |
| ggctgtttgc atggcgggga gaaagaggtg gtccctcctg cctgctgctg atgcccacgg | 1020 |
| cctcctgtcc ccaggaaagg ggtctgcgcc cctcccccac cggaacagcg acagaagagg | 1080 |
| cgaccctctc aaaggccctt ctgctgctca ccgcggggtg agtgatggtg tggagcagga | 1140 |
| tctgggtcca aggtcttctt ccacgttcag ggttcccgtg gtaactgaag aattatccat | 1200 |
| ccagagaggc aggggagggc ctgggacagg gatatatctt attattgata gtacaattt | 1260 |
| taaattttaa attatcagca ggaccgtagg agatgacata agaggaaaa ataacctgtg | 1320 |
| tggcgctctc agcataaagc gcccaggttc agggatgcgt gtgcgtcctg ctgtctgctc | 1380 |
| attcgaagag caaaggaagc agggatgatt tagggcctcc gaggtgacac ggaatcggga | 1440 |
| ggaatggcgc cacgagaaag acgtctttct cattttgtga gcagagagcc catcgttcag | 1500 |
| gaagagcatc tgagccacaa agctaatcac agatcaccga gccagcgccg gctcctgatt | 1560 |
| tgtctgtgtg gctccaggtg gcaggtgctc cacggcactc agtaaaaggt gcatatggtg | 1620 |
| aggggtgcag gcagtggcca aacaagggct tccctggatc ctggagtggc tccttccagc | 1680 |
| cacagccaag gctgctggag ggaagaccag gccgagggca cgtcttgcgt gctctcactc | 1740 |
| acaagcacac acctgtattt accatgttat gtacacccac agaatcatct ttaagatctt | 1800 |
| gttaatatta atatataat tgaaggtcgg aggcagtggc tcaagtctgt aatcccagca | 1860 |
| gtctggagg ccaaggctgg tggatcactt gaggtcagga gttcaagacc agcctggcca | 1920 |
| acatggtgaa accctgtctg tactaaaaac acaaaaatta gccgggtgca ctggcacatg | 1980 |
| cctgtaatcc cagcttctca ggaggctgag gcaggagaat cgcttgaacc tgggagtgga | 2040 |
| ggttgcagtg agccaagatt gcaccactgc actctagcct gagtgacaga gcgagactcc | 2100 |
| atctcaaaaa aaaattaata tataaattaa tatgagtaac atatacacat acattaataa | 2160 |
| aaatatacaa aataatacat atagtatata ataatatatg ctaagtatag gaaatatgaa | 2220 |
| taatataaat aaaagattta tgaattatgc attaaatatt aaataatatt aatatgaata | 2280 |
| taaatattta ttatatctat ctatctgtat gtacctatat agacacagac agatatctat | 2340 |
| ctctatagct agatatttct atctctgtac acactcatct atatccacat gcatgtatat | 2400 |
| gtaaaaagag agagagagca gagacataga gagatttatt tcaaaggatt atcccgtgct | 2460 |
| attgtagagg ttggcaactc caaaactcac agggcaggca ggaggctggt cattcccaca | 2520 |
| ggaactgctg ttgcagtcta cagcctgaag ggagaattcc ttccttcttg tgggaactca | 2580 |
| gtcttttcct tttaagacct tcacctgatt gggtgaggcc cacctgcctt cctctgactg | 2640 |
| gatgaggccc acccacattg tcagagggac atctgtttca ctcaaagcct actgatctaa | 2700 |
| aatgactttg attaaatgac cttcacagca acattcagac tggcgtttgg ccaaacagcc | 2760 |
| tggcactgtg gcccaaccta ggtgacgtga agctcatgac ctccctgtgc ctgcagggcg | 2820 |

```
ctgtggcact ccatccctct tctgtgtcaa agagctgtct gaactgctcc agcaactctg    2880
acacatgggg acgtcctgtc ctgaagggat gggggcatgc taggactggt ttgcgaatct    2940
ctccataaat ggccttgctg tctccagcat gagagaaggt tggagcgtaa agagcagatt    3000
tctgcggtgt cccttgtgct tcctgaaagg agtcccacac tcaagctcac ccccacggtg    3060
gatgtgctgg accaggaccc tggggtgctc ggggcccgag ggtgccagga ttagaacctc    3120
cacacccaga ggttcctgcc tggggcctgc atcacccgtg gcgtctcctg cctgccccgg    3180
attcctcctc tttcttccct tgccgttttt ttctggctcc tttagctgca ggtccacagc    3240
tggcttttct ccagctctcc tgcatactgg ctgagaaggg cacctatgtc attgttgctg    3300
gctgtttgcg ctgctgtaat gcaatccctg agactggggg atgtatacag acaacactg    3360
atttctcata gtcgtggagg ctgggaagtc caagatcgag gcactggtag gttcgtgtct    3420
ggtgagggcc ccagtctgct tcatagctgg tgcccttggc tgtgaccttc agaggaggtg    3480
aacgctgtgt cctcaagtgg gaggcagcag aagggcacat ccagcagtga ggctgttgct    3540
ataacaaata cctacaactg tggaagcagc tttggaactg ggtaatgtag aggctggagg    3600
atttggaagg tgcatgctag aagcagccta gattctcatg accacagaga atcaccacta    3660
agggtgattc tggcaggtcc tcggaagagg gtgctgcgga aaagcccagt tctcctcaca    3720
cttaaatggt tgtgaacaga aagttagtag aaatatggag agtgaagact attctgatgg    3780
ggtcttagaa gtgaggattt ttttttcttt gagacagggt ctggctctgt cacccaggct    3840
ggagtgcagt ggcgagatct cagctcactg cagcctcagc ctcctgggct caaatgattc    3900
tttcacctca gcctcctaaa tagctgggac tgcaggctgc cctaccccgc cctgccacct    3960
cacatggcag ctgttcttta ttcataatcc ccactgtctg tctctgcttc tcttctccct    4020
ttctcttctc tctctgtctt ttggggtttc gtcatgttgc ccacactggt ctgaaatcct    4080
gggctcaagt gatcctccca cctcagcctc ccaaagtcct gggattacag gcgtgagcca    4140
ccccacccag ccagaagtga ggaatatctt actggacgct agaggaaaga ccgaccttgt    4200
tgcaaaatgg caaagatctt ggctgaatta tgtccatgtt caagtgctct gtgtaaggag    4260
aagtttagga gccagaagct gggacattgc taatgctgca tggagccttt ttcagaggag    4320
tcttaatccc attcgcatga gaggaggcct tcctcaccgc ctactcccct cccaaaggcc    4380
cggcctgtta catttcattg caggaatttc ggatgggatg cattcacacc aaagcgtcac    4440
cctcctgagt acctctctga agccaccttg gagcctgggc tccccaggc atgggacagc    4500
acacccgtc cactggagcc gaccctgatg aatgcaggct cactggcttt gccaccgcat    4560
gcccccggag gcatcagacg ctgcttgtct ctgctgcctt tgaaggtgt gcgtggagtc    4620
gcaggcctga actacatgag atcgagacgg aaaccccgcc aggcaccaac taacggatgc    4680
ccaggctgga gtgaccctcc tcctcaccct ggcagcagag acccacgttg gccatcgaga    4740
aagaaccgac gcctagcgag aagtgacagg gaacattcag gatcccccgc ctgccccgt    4800
ctggaccttg agatgaggaa ggactttgtc gttttttgtca ctttaaccga atcttggaca    4860
atcaccgccc aaagcgtgca ctctgtgggc tgtttaaaaa attatatgcg cacagactct    4920
aaaggaaaaa ccagagacaa accgctcata ttccatgaac cttccttctg cataaaccgc    4980
cacgtgtcgc ttggcaaagc cgtgggcctg gcagtggggt tagcctttcc cactcaggaa    5040
ccgcgctggc cacgtttctg ccggcatcag cgccctgag ctgctttcca aagcgcggcg    5100
tcaggaacgt cactcttcac tgttgaattc aacgtgggca cctttaatgg ctcagtcatt    5160
ttttttaaaaa aaatcaaaat tccacgcagg ggccttggtt ccagagctcc ctttccagga    5220
```

```
ggctgttgcg cgggctggcc accaggtggc actgttgcat agcaaaagga acgcggctcc    5280
gcgctggaga accgggccgg gctgcgcgga agccctggag ggccagccgg gtggagggag    5340
ctgcaggagg gggcggcgtg ctttccgggg gtgcaacttg gttttccctg gagggataaa    5400
gctctccttt ggcaggtgcc tggggtgcc ctttaaagca gggagcccag ggaagaccca     5460
gctctcttcc tgtgagctca tccctggcat tcagggtgaa ggacctgcag cctggtctcg    5520
gaaacggccc tccaaggcct ccttgtcccc tgaagcacac aggcagaccg cgggtcgggg    5580
tgcaccgtgg ctgtcccttc cctccaatgc tgggcgaccc gggcgggtgg ccaccgcctg    5640
acctgggcct cctggctgcc agcctgcacg ccctgggtgc agaggcaggc gagcctggcc    5700
tggtctgaac agtcttatga ggattctctg ggcccgtgtg ctcccgcctg cccctgaagg    5760
gcgtagtgga agcatccgaa catgcactgg gtaccctcgt ggcctgggac agcccttccc    5820
tgctgggctc cttgctttgt gttaaccctg aggcctggga gcctgagttg gggaaacggg    5880
ggactccaga caacacccag cttggatgcc ggcgtccact tctgctcaga gaatccagtc    5940
aactcagggc tttgggcttt cccatgacca agaaaagaa gtcagtgaat gagaatcaaa      6000
taaaggaaat gattttctgc caccaccggg gcgcagactt gctgtccata ccactgtccc    6060
tggctgtagc acccatgtgt gcctgtgtgt ccagaggccc acggagccca gatgggcctg    6120
gggatgattt cagcctccaa ggaggccgcc catctcttcc ggtggcccct gcttctcacc    6180
cagtgtgggc caggcccacc tgaatgctga gggcaaggac gagtggtcgt tacctaaacg    6240
agccagagat ggcctctggg gactggccct tgggtcactt atttcttccc tgcaggctga    6300
gctcattagt tcaagagccc actggcacca aactcagatt tttatacatt caattgtttt    6360
aaaaatagcc ccaaacaagc agactttcag ccatttagag cctgcctgtt gcatgtattc    6420
tgcaaaacct cacctggcag ctgttcgcta ttcatcatcc tcactctctg tctatctctc    6480
tgagtccatc tctgtctctg tctccatctc catctctgtc tctgcctctg tttccgtctc    6540
tgtctccatc tctgtctctg cttctcttcc ccctctctct tgctctctct cccttctctc    6600
tccgtctttc tctgtctctt gctctctctc ttccttcttt cccccgctct ctcccttttct   6660
ctccccttcc tctcccccac ccctaccacc ctgtctctct tatctgtatg atggggaatg    6720
aaggatgcag caatggccgc ccatgtgtcg gtgggagctc acttccccaa gcctttactt    6780
gaggggactc tgaagggctt catgtcgcgt cagcttgtga tacgcacaag ccgactgcag    6840
cagacacagc tgggccctgt gtgcacatct tcgcccacct cgaggtcacc tgtggacacc    6900
agcatggagt ccagcctgtg gggaaggctg gagtcaggga ggctaatgcc cttctagggg    6960
caatctgtac taatgaaaga gaaataactc agaggacacc atggcgtccc ctgcagcctt    7020
gcagagggtc cccagcagct gttcctgcac tgaggcctcc ttggcctcct cctccctctt    7080
ccctgcgctt ccccgaatcc gcccccaacc cgtgagcttt gccctccagc ctttggctca    7140
gtgtctgttt tgaggaaac ataaactaag ataacagcct tgtgatttca gggctccctg     7200
tgaccgcagc agggcctggg ttatccgggc ggatgcagct gtccacagac aggcctgagg    7260
ctgggcaggg ggtaggggc tgtggcctgc gtgtgcctct gttccattc ccgtcccctt       7320
cttccttgag gagcacacgc cttctccact gtcacattcc tcctgcatca ggagccccct    7380
ggaacccgcg gcttcgggtc tggtgcaccc tgtggggcct catgccactt ggtgtcacgt    7440
actcaagagt ttattttccc acagaaattt aggagaaagt agggattgtt tgtagtcaaa    7500
ggaagaagtg ttcctcagtg gatggagaag gcctggctgt gctccaaggc cctgggccct    7560
```

```
gcatactcat ctcctggggc ttcctgaagc tccctgtgga gcgtgagcct gccgggccac    7620
ctggagcaca gggggcctcc agggacagtg ggggcactgc gggccgggcc cacgagtggg    7680
ctccttcacc tgggcctccc ccagggctga cagcccttg  gatcccaggg aaatgcgtcc    7740
caaccacaga atgaggtgct gctggggtac ctccttcctc gagcaggaca gccagtcatg    7800
gtgcccctct ctgagtggca tgggcatcca ggtagaagag tgccaggaca tgcctgggca    7860
gcaccctctg ggatgccacg ggctctatcc ccagctgccc gctgtgcctc attctggggt    7920
tgatgggtgc cagggctccc gcatgctgga ccagcagggc accctgcaag gtggtgccgc    7980
cttgaggcag tgccaggagg tgacggctcg cccacacagg ctcccgaaca tcagggatac    8040
gcagtaaaga caacctcatt ctaatgttct gtctgtttgg atagggacaa acacagccca    8100
gatctcagcc ccccggcaga caccagacac cgcaatgatt tgctccagca agccaactgt    8160
cccggagcgg tagctgctgg agtcctgatc caactccact attgtcattc ctatacccag    8220
gtgtgggcga tctgtgctgt tagacctggg gggctgcaat gggtgggacg gaagcctctg    8280
gacccccagt ccctggtgta gaatggttcc tgggagtctg gaagaggtgc catttctcac    8340
gcgcctgtcg gggatggact gacagctgca ggacccacct cgccgcttct agctgtgggt    8400
ccatgcagcc aacacagagg tttgtggtca ctgaggacat tcgtgcagac actttgtcca    8460
gtgcccgagg ggacagctgc aggccagctg tagagtccat gcaagttctg ccctgagcgg    8520
tttgcattga aatccaggca gtcgtctgct ctccacacac ttccactctg actgggaggg    8580
ggccgcagtg tccttcaacc ccatgggtca gcgtccacag gccctggatg atttaggcag    8640
agttatacca gtaaaagacc acagctgtct ggggaagcca ggagcatgcc tggcacccac    8700
tcagatgctg ccctggcagc agccttgttc agggtcccag tctcctgcac atccgggacg    8760
ctgagcaggg ctggctgtca gtggggctg  gctgccgtgc tcacctgcct tctgctgctg    8820
ggggccgggg gactgtgctt cttcgccttt agtggtggaa ggaaaatact catgtaacaa    8880
aaactataca catgaagtgt tttcccccaa agaaacaagg gtgctagccg gaaagatgat    8940
cagctgccag aaaaccaaat aaaatagcaa accttctcta taggtgccca agatgccctt    9000
gacaaaactc caaagccact catggcaaaa cccaaagcca aagagagatg gaggaaact     9060 gctcaaacat gaggaatcgt gcttctcagg agccagtggt gaacacgacc ttaacatatg    9120
aaatgcaaac cactgtcatt cgaatgagaa ctaacgtggt ccccgtcacc cccatcattt    9180
attttggttc tagccaccgc aggaggatca cagaataaca caggccatgt agggaaattg    9240
cagcctggcc gggcatggtg gctcacatat ggaatcccag cactttggga ggttgaggtg    9300
ggcagatcac ctgaagtcag gagttagaga ccagcctggc caacatggtg aaaccccatc    9360
tctatcagaa acacaaaatt atctggccat ggtggcaatt gtctgtagtc ccaactgctt    9420
gggaggctga ggcaggagaa tcacttgaac ccgggaggag gaggttgcag tgagccgaga    9480
tggtgccact gcactccagc ctgggtgaca gagcgagact ccatctcaaa aaaaaaaaa     9540 aaagaaaag  aaggaaagaa agaaagaaag aaaaagaaa  ggaaagaaag gaagaaatt     9600 gcagcctgcc tgagtggggt gtcctgctgg tgaggtgagt gctgctgggg tctggcttg     9660 ttgctgacat atgccttgag aaaggtttga atagggccgg gaacagtggc tcacacctgt    9720
aatcccagcg cttgagaggc tgaggcaggc aaatcacttg agatcaggag ttcaagacca    9780
gcctggccaa tatagtgaaa ctccgttttct actaaagacc ccccccaaaa aaaacaaaaa   9840
aaaaacaaaa acaaaattag ccgggtgtga tggctcatgc ctgtactccc agcttcttgg    9900
gaggctgagg caggagaatc gcttgaaccc aggagatgga ggttgcagtg agccgagatt    9960
```

```
gcaccactgt aatccagcct gggcgacaga gcgagactcc atctcaaaac aaaacagaaa   10020
ggtttgaatg ttcctcagcc acttgagtgg cccggtctgc ccaagtatga gagatttcca   10080
gggatgcagg gctttcaatg ctaagaatca ttttaaaaag gcagtctccg ggagtgagtg   10140
ggtcgcccta gcggctgtga ctggtggcgc ccttccccgc ccctcaccag ccctgaagaa   10200
actgcccctc attttgtttt ttctttgcat ttgtgtgatg gctgctaact ttcttgcatg   10260
cacattggcc atgagtgttt cctgtaagat ataagtttcc tgtgtgtatt atttgcccat   10320
atttcttttc ttttttttga gacggagtct cactgtgttg cccaggctag agtgcggtgg   10380
tgccatctcg gctcactgca gcctccacct cccgggttca agcaattctc ctgtcccagc   10440
ctccgaagta gctgggatta caggcgcccg ccaccatgcc tggctaattt ttgcatttt   10500 agtggagaca agagttcatc atgttggcca ggctggtctc gaactcccga cctcgtgatc   10560
cacccacctc ggcctcccaa agtgctggga ttccaggcat cagtcacggc acccagccca   10620
tatttctaca aagattttgt cttcatcttt taagttcaga atgtaaatac cctgtggctc   10680
ttccatcttg tttgggcct tagtctgaat tgcgccctgt caccacaagg tgcatgaaca   10740
agggcactgg cactgccttc agtgtcacag aaacaacaaa acgatgccaa acacacgacg   10800
tgaaatgctg agatctccat caacaggtga ccgccgaatt cacgacgatc caacgtaacc   10860
gtggaagctg atggaaaaaa ggaggtgcat atacatattg atgttacaac cgtcccatgt   10920
taggctgggc gcggtggctc aagcctgtaa tcccagcact ttgggaggcc gaggtgggcg   10980
gatcacgagg tcaggagatc gagaccatcc tggctaatac ggtgaaaccc cgtctctact   11040
aaaaatccaa aaaattagcc aggtgtggtg gcgggcacct gtagtcccag ctactcggga   11100
ggctgaggca ggagaatggc gtgaacccgg gaggcggagg ttgcagtgag ctgagatcgt   11160
gccactgcac tccagcctgg gtgacagagc aagactccgc ctcaaaaaaa aagaaaaaa   11220 aaataagaaa gaaatctgca ggtttatgag catgagcaca gacagtgggt gaaacagaca   11280
ctaagaggtg ttcacactga cagcggaagg atcaggacga aaggggttg ggggaagttt   11340 ttcgctttta attttgtac cccctattgt ttacccagta agaatggtcg ggtattcctt   11400
ttataattaa aggaagtaat ccattgaaga aaataaaata aataaagttg aaaaagatgc   11460
atgcctattg tgggcctttc ttttaggtaa aaataatgtc tagaaaaatg aaaaccaaaa   11520
tttctaacca tactttttt aaagaaagaa gttggtaaag ataaaaacat aaattaggcc   11580
agactcggtg gctcacacct gtaatcccag cactttggga ggccgaggtg tgtggatcac   11640
aaggttggga gattgagacc atcctggaga acacagtgaa acgctgtctc tactaaaaat   11700
acaaaaaatt agccgggcgt ggtggcgggc gcctgtattc ccagcaactc aggaggctga   11760
agcaggagga tggtgtgaac ccgggaggtg gagcttgcag tgagccgaga tcgcgccact   11820
gcactccagc ctgggcgaca gagcgagact ccgtctcaaa acaacaaca accacaaaaa   11880 cccaaaaaac ataaattaaa gaaatagaaa agaagagctg agcatttcac aaacggagag   11940
caggtgtctg gtgtttggtg tgttccggtc gagtgtagtc aggaaaagga agccgcgttg   12000
tctgcggggc gggggcctgt gcttgtggct gcagcagccc cttcccatca gataaggaca   12060
ttgttcatgc gcggactggc acccaggaca aaaacaacac ccacaaaacc tggtagcccc   12120
acttaatgtt cccctgccgc ggcggctgga ggatggaatt accagaagca attagacaaa   12180
ggaggttcag aaccacaggc atggaattaa ctaactttat ttaagatgac atgtggagag   12240
actggaagga caccttcgct ctgtctggga agccgtgagg ctgaggggc tgtccccgc   12300
```

```
ccgggtcccg tggggagccc atcttctacc aacccatccc aggttcagca gggtctcttg   12360
cttttgttcg gagcgcagca ggaggccact gaggtgccca caaaggggag agatgggagg   12420
cagaccatgt tctcagtgac cactgtctct gctgtgtgat gaggggttgt cttggggagg   12480
aaagaatgca tgtgaccggc aaagctgcag aaactcagct tagaacaggt cacaatcatg   12540
gtagcaaaca ctggggtggg gaagtcggcc ctgactgaga ggccaggatg gatcccaggt   12600
acgtctctga ggggaaagga acagggcccg tcacgagcag gaggtgccgc tgaggaaaag   12660
caagtttctg atgtgactcc tgacttctca caatggggcg tggcaccagc aatcagaagg   12720
gtaaaggctg tgggtcgaat cagaaggtgc atcatacgta tgccgagatc agacgcctgt   12780
gacacggcca ggaggtgtgc agaacacagc ccatgatgag actgcccctt gggcacagtt   12840
agggactgca ggatcatatt taaaatttct ggtgcacaga tgttgtgtaa agagactggg   12900
agagcgggag attgggagag gggaaggaga ggaggagggg gagaaggaga agagagaagg   12960
cctccaggag cctcagagct gatggacgcg gagaagctgc gaagcctaca caggggacag   13020
ccgggagggt aggggcagca ggtgagagga gagagggcgt taagctggac ggggtgagct   13080
gtgcgggtca ccacaggcgc agagggatga tgagcacaga acactgcctt cgggggcttg   13140
ggtgaccacg aagacgtgtg tcaggctgga gaccctaccc tgcttagaag ctgaatgtca   13200
gtctatgact gtctcatggg taccaataaa catactcccc atggccctgt cccactctcc   13260
acggccctgt cccactcccc acggccctgt catactcccc acggccctgt caaactcccc   13320
acggccctgt catactcccc acggccctgt caaactctcc actgccctgt tgcactcccc   13380
acagccctgt cgcactcccc acggccctgt cccactcccc acggccctgt cacactcccc   13440
acggccctgt cccactcccc acggccctgt cccactcccc acggccctgt cacactcccc   13500
acggccctgt cccactcccc acggccctgt cacactcccc acggccctgt cccactcccc   13560
acggccctgt cccactcccc acggccctgt cccactcccc acggccctgt cccactcccc   13620
acggccctgt catactcccc acggccctgt cccactctcc acggccctgt cccactcccc   13680
acggccctgt cacactcccc acggccctgt cacactcccc acggccctgt cccactcccc   13740
acggccctgt caaactcccc aaggccctgt cacactcccc acggccctgt cacactcccc   13800
acggccctgt cccactccct acagccctgt cgcactcccc acatcccgtg gcatctggct   13860
gtacatggaa gtgaggaagc tgctgtctcc cccaaagaac attgctccca gccagggctc   13920
agccctgtgg ggcaggactc agaggctcct ggttcagaga ccagggccct tgtcacttgc   13980
agcgtgaaca gcagggaact ttgccccgga gtcccacaac agaggtgggg accttgtcac   14040
ggtgggccca ggtgtgacaa cacagggcca gcgattcttc acccggcagc aaacactgca   14100
gcagacgaca aacattgcag cccttggcaa acaaaaagca cgcagcaaac agcgtggtca   14160
gcgaaaagac cctcccctcc ccggggatca gacagtgcaa ggccatcccc gggatgacct   14220
gcacccaccc ggctgcctgt gtgaccagcc acagaaccca ctctgcatta gcacccacgg   14280
ccaggacagg cagggtgctg cgcccgtggc ttcctgcatc tgccgacacc acccgaggct   14340
gccaggccac aacatgaagt cagctgtgcc aggaaatccc aagcctcgcc cacacctggc   14400
cccgggctgt tgctgcatgc caaggggttg cccacctggc tgtggctgcc ttaccccatg   14460
gaatccaggc tccaactgac ctcaccattc tgtgggttaa ttttcattct taaaaccttc   14520
atctaaagac ctttgcttcc tggaacacag gcctgggttt tcccaacagt cgtgggcacc   14580
cggcctggca cgtgctgctc agtggaggga cctcacagcc cgttctatgt gagctgtgca   14640
ggaaaagctc cacggacaaa ctcactctcc gtgacaatca ggaggtttct tctccaacca   14700
```

```
caagaaggag ctgggggagc tcgtgaggcc aggaagagaa cagtcctaat cccatccttc    14760
ccctcctcag cagtgacccc agggtctgct gtcctgcccc aacccacact tcaaagaagg    14820
aaggacacct gccttcccct gctacctcac accccgaagc atggggagca tggggaccct    14880
tggcagagtc cttttgtagt gaagaataac agactagtgt aaaatagcag aaaagaagct    14940
aatggccaaa cacatccaag ctggggaaaa cacctgttaa atataatgac agaatatgct    15000
ctcatcaaaa cccaggaaac tttaagaata cactaaacct cacaaaatgg gggcgaaata    15060
caatgatgac cacacgtatg agaaatggtc aatggtagaa ttgaaagaaa tgcaagggaa    15120
atgaaagata aggggtcctt tccaagcaaa gtggcaacgc cacaacagct cgcagtcagt    15180
cttggcggga caagaatgct gggcagtgct ggtttgcagg gaggggtcaa cttttctgga    15240
agcagcccag caaagtgccc cacgagccat caattattcc tgtgcttcgc agccacagcc    15300
cacgaatgca ggtgcagcca cagaagcgct ggcagagggg aggctgagag tggcgctggt    15360
tgaagatttc tcacaggaaa caaaaggcac agcctccacg tggctcatgg ccatgaaaac    15420
ccttgactca aaactttcca cgtcgtgagg aagacgcggg tcagctgccc tagttgggtg    15480
atgatgatgc tgtcagggaa agcgtctgtg cctatgtggg gagagtaggg gagtgagaaa    15540
caaagcaaag cgtggtggct ctgtggctcc agtgccccgg aggccacggc tcactttttc    15600
acaatgaaca tgggctattt tcattttttaa aagtctacta atgtttctaa ggagaccata    15660
cagaaccgaa aattctgaat aaccttgtct tccataaggc agacttttca tttctgtcac    15720 cttttccggaa gggctggaca cagagtctgt gggtctgtga tggaggcgcc accatctcac    15780
cccgagtcca cggccctcag tctctgtgct ccccgagccg aaggtgagga atccatgcct    15840
tatggttggc gagggctgct ggggcacctg ccatctcatc tgcatcctgg aagcaggaa    15900 ggagcacaga ggaaaacaca agcctgctct ggccagctca gtgtgctcct tccagaaaca    15960
ggtaaacaca aaattaccct gcgaagccgc cattccattc ctaggtctat ccccaaaaga    16020
aatcaaagca gggactcaaa tacttgcaca gcccttgcca cgacctggat gtagtcagtg    16080
catctgttcc cagcaaaaact cttgttgaaa cgggacccc agtgtggcag cgtagggagg    16140
tggggcctga ggggagggag acgtgtgggt cgtgggagtg actccctggg gagtccgtgg    16200
tgctgggagt gattctcctc ttgtgataca gggtgagttc ccatgggaat ggatttgttc    16260
ccatgagtgg ggcttgttct gaagccaaga catccctgag ctttatctct cttcccgtgt    16320
ctgcttcccc tttgacctcc tccagcagaa gccagggcca tgccattgaa cttctcagcc    16380
agcagaactg tgagcttgat gaattacccc atcacagagg ttcttttatg gctacacaga    16440
atggactcag acacccatgc tcacagccgt gcagtcacaa tagcccaaag gtggaaacaa    16500
cccagcaggt gaggggatct gaaatggggt agacaaacac atcggggtct tacgagcct    16560 ggaaaaggag tgtgctctga cgcctgcagc aacgccacca accttcacag cctcgtgccg    16620
agtgaagcca gccagtcaca ataggaccaa tgctgtgacc ccacagatgg aaggccccca    16680
gaggagtcag attcaagagg aagatggcag aatggcagtc agcagggcca gtgacagagg    16740
ccgatgggga tgagtgatta gtcaggacgg agctccagtt tcgcgcgatg aaaaggtgct    16800
ggagctgcat ggtggcgaca gtggcacagc cacgtgcagg ttcccaatgc cacggaactg    16860
tgcacttacc atggggatgg tgggaactct catgtacccg catttgacca gagaggaagg    16920
aaggaaggga gggggaggg aggagggagg gaggtagcag agaaggaagg aaggaaggga    16980
aggggagggg aggagggagg aggcagggag ggaagaagga aggaagtgag ggaggggagga    17040
```

```
agggagagag ggatggaggg agggaagaag gaaggaagga cggaccagcc tgttaggctg    17100
actgacagag tacccctgt cctccaatgc tgcccacggc aggcatgtgg cagtggctga     17160
cagggagtga gtctggaagc gacccttgtc ggggcagcct ccttggtcct gtgattcaag    17220
acagggtgaa agtcagtggc ggccattggt gcctctggcc ggggttcctc acaggggccc    17280
gcaaggggac agcgaatgga gcgtggaggg tggagggctc cttctccaga ccggagcgat    17340
gggttcggga gccattctgt gcctgtcttt gctgctgggc tgaggagctg gatggcatgc    17400
tgggagtagt gggagctgct gaggagtttg gtcctggagc gaagaggctg aatccgcatg    17460
tctggagtca ccgtggaggg cacagctaga gggagcagca gggtgtccca gggagaagac    17520
accagggctg gaattagagg gacatcaagg ctgatactta gaggcatcca atatatgggg    17580
cctgcctgat gggctgctct caggtgggat ttgggggtg tgagagggt cagtgcccaa      17640 atgaccatgg ggtccgtggc ctgtatgccc agtcaggtga cgacgccatt cagaaagtag    17700
atctcatggg gtgcccggct gctgagtctc aggccagatc tgcagtgagt gtgctgcccc    17760
aggcgtggaa cactctggtg ccatcgggac ccaaggctga gtgcacccaa gagctgtggg    17820
tctgaaacag cggtcagagg tcactgacat gtggaggagg ccctggagt gtgggagaca     17880 gaatccccag gtgtcaggct tggcaggagg ctttgcaggt ggggaggaag ggcaggtagc    17940
gtggctgccg gaggagggag ggcactggta ggaggagggt ggcctgtccc gggcagacca    18000
gcctctttgg gctgtgtggc cccagctccc tgagcccaga gggaggtgag ggtgagaagg    18060
cctggaccag gcaggacgca gcccccaggg cccctgctgg gaagaggtca gaacctccca    18120
aggacccaga aggccaggta actgagaacg gggctgctct ctgaatctcc agggaggaca    18180
aaggcggcca tggcagcaag gggacagggc agagggaaag gccggcaggt ggatgttgga    18240
agccgcagat tccatccag tatcctagag gaggagaccc agggctgtgt cctaggaggc     18300
ccaggaagcc tggtcagcct ggaggctgag ggcgggcccg ggagatctgg taaggacatc    18360
agtgtctcca cgaagagcag cagggtctca gcccatggca gccgcaggcc ccatgactgg    18420
ggccgcagcc tccagagccg ccacagcagc ccgttgttct gggggggtcaa aggtggaggc    18480 tgtcagaggg gcagtgcagg gggctgctgg ggtgaagccc cctgtagcag cagcacccag    18540
cctgctgtgg ctctgccctc ctggaccccc tgccctcctg gacccccgt cctcctggac      18600 cctctgccct cctagacccc ctgccctcca ggaccccctg ccctcctgga cccctgtct      18660 gtggcccctg ctcctctcct ccttccccga cacatgactg gaccccccga tctgcagccg    18720
gggtctgggc actggggtc ctgtggacct ctcggtgtct ggggacaatc acaggttccc      18780
gtgcccacac ccagcctctg cttccagaac acactagagg gtcccggcat cctgatgagt    18840
ccactgtccc cgcgatggtt ttcagggatg gagaaggctc cctgtcctcc gctgaaccc     18900 tgcagccggg ctgacggtac ccccaccacc cacccagggg ccccagaccc tccccatctc    18960
caccgccaac ccaggccccg gctgcgcacg cgggggcagg ccgtgagctg ctgtccccgg    19020
atggggccgc cccgggctgg cctggctcac tccgtgtcac agatattccc acagagaccc    19080
cagcgagacc tgcagaacat tacagcagaa tgaaggagag ccagaggaag aggcagatgt    19140
gctggcctgt aaacagtctg atttccaatg taaaccagat tcaggcccac gacatcaggt    19200
aaacatctgc atcagagccc ccggcccccc accgcccggg aggccccggg gtccacacgg    19260
ccgactctgg gacccgtcac agtgaccgcc gagacatttc gtaattaggc aaaattgatc    19320 cttgcattc ttccctaaat cccaaatctc tgcaatttta cttcttctca aaaatgaaaa      19380
catttggcaa ttagctgatc caagtgaaaa aggtagagaa tgtgctctca actggaaaat    19440
```

```
gccaattaag gaagcagctc tgacttccca cccgccctgg ctaagctggg agcttatctt    19500
ccccgagaag aatctgctgg gataagggg cttgggaaac accgagggca gggctgcctc    19560
ctcagcttcc tctgagagca gattagccgt ggccttgtgc cagcagggcc tgggtgccac    19620
acagggtggc aggggtggca gagccgggcc cggctctggt actgggattt ggggtggcgg    19680
gacccagtgg ggcacccgct tgtgggcggc actgagggcg gtgacgtagg cagcgggtgc    19740
cggtgtctgc ccctccatct ggccgggctc cccaccctgc tcctgcagcc ctggacctca    19800
gggcccattt gcggtgcaag gcggctcttg gccattttgc ccgcagggcc tacccttggg    19860
tcttgggagc ttctgtccct tgccctctct tgtccaggtc agcatctccc actgtgggaa    19920
tcctatgtgg ccccatcgtc tggacagtgt gggtcaggtc actgtggctg ttttgtgatg    19980
cgtgtgtggg ctcatccctc agtgctcaga agctgcagac actatggaac cgcttttcag    20040
gccccgtggc cgtcaccccc gctctagaga cttgattgca gggaccatgc ccggccggcc    20100
taactgcacc cctcactcca ggtggtggg gggacccagg cctgctggcc cctgtggtgg    20160
tgcagcccag aaggtgtgaa tcagtttaca ctgttcagtg cctgaataaa agtcacagga    20220
caaagaggac ttggttgcac aaactactga catgaaattc acattttgtc ctgaaggaaa    20280
cgcaagatga attgaactca tgttcagttt ttatttctca tttctcccgc ctcagtctct    20340
tctcacgtgc acgacctcac agcgctgtca caaggcctgc tgggcacacg cagctcatag    20400
agaagtgatg gcttcctcct tgcccctca cctccctcct tccctctcc ccctcacttc    20460 ggagcacgca ggctgattgt ggagacatct cccagccagg atgtgtcaac agggaatgtg    20520
ctggggacag cgggagttca cagccacccc cgcaggcgcc ttcctggagc acgtccacag    20580
gccatgtgca gctgcatccc ccacgacggc agggacaagt tccttccata gggcccgggt    20640
ggcccccaga gctgcaccat ttatgatccg gtcctttgca gaacgcaagg gacagacaca    20700
tgaaccctga cctaggttct tgtgcagaaa tgttctctca tcggaataga aaggtatgag    20760
tctcaggact ggttctctgc aaagcagcca tcggcctttc aagcagaaac catggagccc    20820
ccagaggctg agtcttccaa ggcgctggga gacttggcgt ttgcctcttt tttaaatgca    20880
atgaccgttg cagtgcatgg aatcagagac atgtatctat gcgtagaaat gagtctgtaa    20940
acacgatcaa ggtgtgattt ctgtatgaca atgcagttgg atcagaaatt ggagagtgct    21000
ggccgggcgc ggcggctcac gcctgtaatc ccagcacttt gggaggccga ggcggatgga    21060
tcacttgagg tcaggagttc gagaccagcc tgggcaacat ggtgaaaccc catctctact    21120
gaaaacacag aaaattagccg ggtgtggtgg cgtgtgcctg tagtcccagc tactcggag    21180 gctgacgtgg gaggatcact tgagcccagg aggcagaggc tgcagtgagt agagatagca    21240
ccactgaact ccagcctggg caacagactg agactccatc tcaaaaaaat aaataaataa    21300
ataaataaat aagaaagaaa agaagaaata gtggagtgct gtggtcactc tggaaaaaga    21360
ggagggaccc caccccaaatg tggttcctcc gtcaaccctg aagacgcccc cacacaccgg    21420
gacgagatga aagggtctgg tacttaccta gctgggcttt cacggggtgc acggtggctt    21480
caggaaggga gctggcgtgg ggctcttctt atgcctcggg ggtgggggtga tggcctcaca    21540 tgggcaggag cctgcagggc ttgagcctct cactggcacc aaagacacct gccctgctgt    21600
ggggcacacg ggaagaggga tgggtgaggt gtcaaagcag tgagccgtca aacatcataa    21660
aaacggagtc aggctctta ttgcaggaaa caatttgcgg cttctgtgc agagagcagg    21720 ggggatttga ggtgggcttt gtagagtgag ggagttcacc agattgacag tgtgggctgg    21780
```

```
gtcaccctgt gcaaagcagc gatttccatg ttgcccctga gagaatgttt tcctgtgatc    21840
tccagcatcg agatttaaaa attatcatgt tcatagtctg atgataaaac attaatttt     21900 aggaaggcag aggacctgcc tgcttttcct gataagacct cgttccattg ccctaggtca    21960
ggcatggatt attaactctc agggttttgg gggaccagca gccacagatg tggagtcctg    22020
gggaaagggt gacagcctcc tctgcctccg gggatttgtc cttcagtgac ttgacgcccg    22080
caagagtgga tgctaattct caccgtcccc atgaaatccc tgctgacgca tgctgcccag    22140
gagacatctc cacaatcagc ctgcctgctg gagagaggaa ggagggaagc gagggtgcaa    22200
ggaggaagcc agcccttctc tgtgagctgc atgtgcccag catgcctcat gacagccctg    22260
tgaggtgaga ggagactaag gcgggagaaa tgagaagctt gcccgagtca cgcaaccgaa    22320
gcacagagcc agggtctggc gccctgagag gtcctgggtg cattggatgc tgtgcacgta    22380
cttcagcaaa gaggcaggat gttgtcatct tccttcggag ccagtaacat tttctgctgc    22440
cagcaaggaa agaacattgg atcacgcgcc tccatgcagg cagggtcctt cagtggcgct    22500
gatcctgagc ccagccctct cgtggtctgt gctgacgcca gggcctctcg ttggaaggcc    22560
tcgtgctcca cagttccccc acaaagggga ggatgctgaa ctctttacct gtaattctgg    22620
cctcgaagca gctgttttct gcctggcttc tcacccccagc catgcacagt ggaggtgtca    22680
gcaaatccct ggagagaaag cccggtggac acagggttcc tttctctgag gctcccttc     22740 cctgggatca cagtagctga gtcggggtct ccagagaaac agaactgggg taggggggt     22800 gcataaagtg agaaggagat ttattataag gcggggactc atgggtaat ggaggctgca     22860 agtccagcat ctgcagtgtg ggcagtgtgg gtagtgtggg cagtgtgggt agtgtgggca    22920
gtgtgggtag tgtgggcagt gtgggtagtg tgggtaatgt ggatagtgtg ggtagtgtgg    22980
gcagtgtggg tagtgtgggc agtgtgggta gtgtggatag tgtggatagt gtgggtagtg    23040
tgggtagtgt gggtagtgtg gatagtgtgg gtagtgtggg tagtgtggat agtgtgggta    23100
gtgtgggcag tgtgggtagt gtggatagtg tgggcagtgt gggtagtgtg ggtggtgtgg    23160
gcagtgtgga tggtgtgggt agtgtgggta acatgggcag tgtgggtagt gtgggtagtg    23220
tggatagtgt gggtagtgtg ggtagtgtgg atagtgtggg tggtgtgggt actgtgggta    23280
gcgtggatag tgtgggcagt gtgggtaacg tgggcagtgc gggcagtgtg ggtagtgtgg    23340
atagtgtggg tagtgtggat agtgtgggca gtgtgggtaa tgtgggcagt gtgggtagtg    23400
tgggtagtgt ggatagagtg ggtggtgtgg gtagtgtgga tagtgtaggt agtgtgggta    23460
gtgtgggcag tgtgggcagt gcaggcagtg tgggttggcc agctgcagac ccagcagagt    23520
ccgtggagcg gatgaagtcc caaggccgtc cgctggagaa tctctcttgc tcaggaaggc    23580
tggctttctg ctgtattcaa gactttaact gatcggaaga ggccacccac attacagaag    23640
gcaacatgct tcacccaaag ttcatccatt taaaagttaa cctcaggctg ggcgcagtgg    23700
ctcatgcctg taatcccaac actttgggag gccgaggcag gcgggtcacc tgaggtcagg    23760
agtttgagac cagcctggcc aacatgggga atcccgtctc tactaaaaa tacaaaaat     23820 tagccgggca tggtggcaca cacctgtgat accagctact cgggaggctg aggcaggaga    23880
atcggttgaa cccagaaggt agaggtggag gctgcagtga gccgagatca caccactgca    23940
ctccagcctg ggaacagag ccagactccg tctcaaaaa aataaataaa tgaagttaat      24000
gtcctctaaa tacactttcc aaattgacac ataaaattaa tcatcataag agagctgaca    24060 ttcattttt aatattcaaa ataggatctt gcaacaagac agtcagctgg aaagctaggc     24120
ttgtcgagag aggcagacag agagaaagag agaaacagag agaaagacag agaggacttg    24180
```

```
ctaagttcct tcatcctatc cagaagcaaa cccgggagac ttcgcccata gctgctgtga    24240
gcgttcgtgg gcaaatgctt tcatttctct tgctaaatac ctaggtgtag aattggtcat    24300
atggaaagcg tggacctcac cgtttaagaa cccaccaaac tgttttcaa agcggttgcg     24360 tcgtttaaaa tccctcctc atactgtata ttttgttctg ctgacccgtt tgtctctctt     24420
gacaccaatc cccttctgtc tccatgactg tagcctcacg gcgagtcttg aaatcacaga    24480
tctttggtcc tccaactgtt ttctcttttt caagattctt ttggttattc taggtcctct    24540
gcatgtcctt atatttttta taatcaacat gggaatttct cttaagagaa aagaagcgct    24600
tctgggattc tgattgcaat ggtactgaat tcattaaccc atttgggaag acgtggcatc    24660
ccgtcaatat caagagtttg acccgtgaac gtggtgcgca cctccattta tttcattcac    24720
cttgactttc tcccagccgt gctcttagca tatctcgtac atcttttgtg agatttattc    24780
gtaaggattc atgttctctc tgtaattta aatggcattt gagttcaatt tctgctgtaa     24840
tacagaaatg caattgattt ttagtggcct catgaagata aaactcatat cacacacttc    24900
acccacttca agtacacaat tcggtggttt ttcatatatt cgcagagttg tccagccgtc    24960
accatgctct aaccaccatc acaatgtaat tctagaacat ttttatcacc tcaaagaagc    25020
catacccatc agcagtcact ccctactcct cccgctgagc ttctccgctg gccttggcca    25080
ccactgatct ctcctcctc tctgcggctt tgcctctgct gaatacaaat cgggttctgc     25140
tatgttcatc cttctgtgtc tggcctcttt cacttagcgc aaggtttcaa ggttcatgca    25200
cgtcatggtg accagaactt catttctttt tatagctgag aaatacccca ttgtgtggct    25260
agtctgcgtt ttgtgaaacc atttattggt gctgggacac atgggctgct ccctccatgt    25320
ggctattaga acaatgccat ggtggacatt tgtgcacatg tttttgtgtg gacacgtttt    25380 cattttctt gggtggagta gaattgctaa atcataggat acatctatgt ttaacatttt     25440
gaggaactgc caaactgttc tccaaggcga ttaaatcatg ttgtgttccc gccaacaaca    25500
taggagtgtt cgaacttatc cacgtcctca ctaacacgga ttatcggcct cactgacgct    25560
gttccagaga cagtgtggaa tgatgcctca ctgtgagtgt gttttgtgct tccctaatga    25620
gtagtgacat gccacacctt ttcctgtgct atttgccatt tgtatctctt ctttggagac    25680
atgtctatca ttttttaaat ggggttaatt atcccttat tactgactac tgattttgta     25740
tactgatctt atagcctact attttgctta agtcactcat tagttctagt agctttctag    25800
aagattctgt tagattttct acagggatgg ccatgaccct gtcttacttc ttcctctgca    25860
atctatgttt tgttttgttt tgttttcctt tccgtgcctc attgcaccaa ctagaataga    25920
gacgctttga gtaggcactg ctgctggttc cttctcttgg gggaaagcgg gcaatcttct    25980
gctaggaagc aagatgcctg ctgcatctgc ttcggagacg ccccttatc agactgggaa     26040 cattcccttg tgctctcatt tggcttgagt ttttattata aatgcataac ggatatcaga    26100 ttttttctg tgtctatgga gatgatcata tggcttttct tttttagctt gtgaatgtgg     26160
tgaaatgcac tgatctttca aatattcagt tgatcttgcg ttactgggat aaactccacg    26220
ttgtcatcat gtattattat tgtacatatt actgtatcca gtttgctaaa tgtttgcctc    26280
tatgttcatg aggggtattg gcctgtagtt ctccttgtgat atctttgttt ggttttgta     26340 tcaggataag cctcgtagaa tgtgttagga aatgttctct ggtcttcggt ttcctggaaa    26400
aagttgtaca gagtcaggat tctctatttg ttgactgctg ggtgaaattt accagtgaaa    26460
caatttgacc tgtcatttcc tttgtcggaa ggttttgaa ctacaagttt aatttcctta     26520
```

```
acaaatacag ggctctttgg tttatctatt tttttagtga ctttaataat tcgtgtcttt   26580
caaaaaaatg tatccatcac atctgagttg tcagatttat tgacctgaat gttctgaata   26640
gtcccttcca tccttttaca tatttataga atctccttct ttcccaatct tgctaatttg   26700
tgcagtctct ctctttagtg attagacagg ggaaagatta atcaatttta tggattttct   26760
gaaatcatgt gtgcagagca gccacgggat agcacggcct ctgcacgctg tggggtgttc   26820
atcagctgga caggcagctg ccacctggac agagtgaaac ccaccgcctg agttctggag   26880
taattgtccc aaggaggacc tttccactct gggttgtcct ggaagaggc tgctcctcgt    26940 ctaggaagtg aggtcctggg caaagacctc agtgggaggg aggagacatg atcttcctga   27000
gtctcagccc caaggcacca gcctggatcc ctcggtgtgc tgcccagagc tcgtcaggca   27060
ctgatgagga ttgagaggag ggcagggggg agcacccacg tacgacagga cacacacaca   27120
cacacacaca ttcccctcct gagacatttg catccaggga acatgcaggc aattccttgt   27180
ttgtgcaact aaaactccag agtcccccaa agtgaaaaca gcaggcggct ccgaagtgaa   27240
ctgcaactac cacctcttcc gagacagaaa acgctcagta ctgggaggac agggtttcca   27300 gattttctt ccccaagtag gttccaaaaa taccaaggca ctgagtttca gccagggcac    27360
gcctcgcacc tggcctggtc ccggggatca ggatgcactc tccgcacgga gccctcttct   27420
tggtggcctc tgcggcctct gcaacggagc ttgtcctggg acaacaaagg tcttaatctg   27480
gcagctcctc aaatgaccag ccctgggaag ggaacatggt catgaaaata ataagaaaga   27540
aaaaggacta cagcaaaaca gaaaacctga tttaagacag caggacttt gaatcctgat    27600 acaacaggtt atcagaagaa cgaataaatt aaacttacca attaaaagac acaagagtat   27660
ggatggagtt aaacgatgtt acccgcgaga gacacagaat agttgacaat aacaggaagg   27720
gaaaatgcaa gccaattgta tgtggactga agaaggcta caaaaggatt aaaacattaa    27780
gccacaatgc agctttctga cagtcaaatg atcaacatac agaaatatat tttccaacca   27840
cagggcaaaa aaaaaattag aaattaagtc acaaagggga tagtgcaaat attgtatgtt   27900
tggaaaccaa atagtctatt accataaatt tggggttaaa gagataatca taattattaa   27960
aaagtaataa aaacattgca cattagaagg acggggcaga gtgaagcagc tgttactgag   28020
aggtgtacgg tactaaatac atttctcaca aattatgaaa ttggatgtct acgcagatgt   28080
tttgcctgtt tctaacggag ctgtttttgt cattaatttt ttagttcctt ttccattctg   28140
ggttcaatct ttcatcagtg atatggtttg caaatacatc ctccagatct gcgacttatc   28200
ttccgatttc ttgttagtgt cttttgaagc acacatttga aaaaaattcg atgaagttca   28260
ccctatcaat gttttatttt acgatcttat ttttgatgtc atggctaagg aattgcacct   28320
ggcccacagc ttccttgact ttctcccatg ttttctacaa gttttagttc ccggttttca   28380
tgtaaccctc tttgtgttaa ttcttgtgga ggacatgaga tagggttcca aacttctttc   28440
tcatgtggct atccagatgt cccagcacta tttgtggaaa agactgtctg tcccccgact   28500
gagttctgtt tgttgccttt gtcaaaaatc aattgacaat ctacataaaa cgttttttt    28560 ttttcctgga cttttgatcc tgtttcattg atctgtgtgg ctacagtgaa accaatacga   28620
gactgtcttt gttactaaat tttgttcttt taaaaaattg ttttatccat accgggtcct   28680
ttaagttatt tttgtcatga agtttttagc tctttttct attctggata caatcttta    28740 tcagttatat gatttgtcaa tattttatcc taatcggtgg ctttcctttc attttcattt   28800
gtaaatatta ggatcaattt gtcaattttt gcacaaatgc ctgctggatt ttgacaggga   28860
ttatattgga tttacaaatt gccatgttaa cgtgattgtg cctctggccc atgaacacgg   28920
```

```
gcggcctccc cagttgctca tgttttcttt aattcctctc agcaggattt gggggttta    28980
gcatttaact cttatacttc tttggttacg tatatgcttc tgtatttat tctattatta    29040
tttaaaattt tcttaatttc attttcagat tgtctattac taatgtatag aaattcagtg    29100
gattttgtg tattgatact acactctgca cctttgctgg attttttatt agttctaaca    29160
ggagtgtttg tgtttattct gcttagggct ctccaaaatt ctcaaatatg tgattttttt    29220
tgtctttgac tagctttggg agactctcag ccaccatctc tccaagtagc ttttcttcca    29280
cgatttcttc tttcctctta ggatcataag tggacattca ctagagtgtg ttgaagtgtt    29340
ttaaaggtct tggatgcttg atttagttct ctctctttgt cttttttctc tttgtgttca    29400
ttttggatga cttctactca cctgtctccc agtttatgga ttctttcctt agttctttcc    29460
agtgtgttaa ttagcctatg ataagaatgt tgatattgtt ggtgggggg cggtggtgga    29520
gaggctattt ccatttgact tttgtttttt ttgagacagg gccacgctct gttgcccagg    29580
caggagtgca gtggttcgat cacagctcac tgcagcctct aactcctggg ctcaagagat    29640
cctcctgcct cagcctccaa agtagctggg actataatcc cagcactttg ggaggccaag    29700
gtgggtggat cacctgaggt caggagttca agaccagcct gaccaacatg gtgaaacccc    29760
gtctctacta aaaatacaaa acatagttgg gcatggtggc acacgcctgt aatcccagta    29820
ctggggagtc tgaggcagga gaatcactcg aacatgggag gcagaggttg cagtgagcca    29880
agatcacacc actgcactcc agcctgggca acagtgtggg actccatctc aaaaataaat    29940
aaataaaaac agtgttctag tttttttcag ttttcattta tctgttgaaa ttcctcacct    30000
gttaatgcat attgactaaa catacccatc acagttattt ttatttattt atttgttttt    30060
ttgagatgga gtctagctct gtcacccagg ctggagtaca gtgatgtaat ctcagctcac    30120
tgcaagctct gcctcccggg ttcgagcgat tctcctgcct cagcctcccg agtaactggg    30180
accacaggca cctgccacca tgcccagcta atttttgtat ttttagtaga gatggggttt    30240
caccttgttg gccaggctgg tctcgaactc ctgacctcat gatccgctca cctcggcctc    30300
ccagagtgct gggattgcag gagtgagtca ccgcacctgg cctgtgagtt atttaaagt    30360
ccctgtgcaa cagtgtcaac attggagtca tctcaaagtt ggattctatt aattgtttta    30420
tcacatggcc atggttcatt ttaccttcct tccttgctat ctcataaatt ttaattgaat    30480
ttcagacact gtgtccagag aataatagag acggaggcag gtagccttta tgccccagat    30540
ggctttggat ccccttcttc tgggtatgaa tgtgggatct gtgccagcct gggccatggg    30600
tgggccgggt cagggtgagg tgtggccgcc attacctcag ggcgtcagag actgcgaggc    30660
ctcctaggca agctcaccct tacctggtgc tgaagcctgg ggctgggac agggaggat    30720
tttctttttt ctttttttga cagagtttt tgttctgtcg cccaggatgg agtgcagtgg    30780
cgtgatctca gctcactgca agctccacct cccgggttca tgccatcctc ctgtctcagc    30840
ctcccaagta ggtgggacta caggcgtgta tcaccacgct gggctaattt tttttgtattt    30900
ttattagaga tggggttttg ccacgttggc caggctggtt tcgaactcct gacctcgtga    30960
tctgcccgcc ttggcctccc aaagtgctgg gattacaggt gtgagccacc acgcccggcc    31020
ccagggaggg tttcctcagt gcccctacag ctccattgca gcaggccctt catgcctgaa    31080
ccacagaggt ggttttctcc atgttcttgc cccttcgttc attttacgca acagatatct    31140
attgagcaac tgccatgtgc cagacactga gctcaagtat ggtttattct agcgaggcag    31200
gaagagcagt gggtctattt atgtgattct ggaaattcac aaaggatgaa acctatgact    31260
```

```
actcaagtat tagctgcaaa agctggtaaa gttcaacaaa gttcgaaagc ttgctatggt   31320
tcagcattcg tttatgttag aaaaaaagaa aaacttgaaa agctattaat atctaacttc   31380
tgaagaatat ccctcgggaa gtgatattaa aagtcacata gaaacattag gagaagcagc   31440
tactacctgt cttattaaac attgttttga atgatagcat tgggacacac taaaaactaa   31500
atacagttca aaatatttaa aaggaagaaa tgaaacaact agaacaaaag ctgagtaaag   31560
atacaacatt ataaatcaac ggattttcta gacactatgt agagaaaata ccacatgaca   31620
acatttccca tttataattt taaaattata gaattctatg gcagccggg cacagtggct    31680 cacacctgta atcccagtac tttgggaggc tgaggaggcc aggtcacttg aggtcaagag   31740
ttcgaaacca ccctggccaa catggcgaaa cccagtctct actaaaaata caaaaactta   31800
gctcggcatg gtggctcatg cctataatcc caactgcttg ggaggctgag gcaggggaat   31860
cacttgaacc caggaggcgg aggttgcaat gtgccaagat tacaccattg cactccagcc   31920
tgggcaatga gagtgaaacc ccatctcaaa aaaaaaaaa aaaaaagcct cctacccata    31980
agatgtaaat aaatggagag ataacagg cttcttgatt gagaacactt acaacttcag     32040
gtctctaaaa atcaacctat ggatttaatt atattccaat taaataaat aattactttt    32100 atcttgccaa gttttctcta aaattctcat caaaatgtat aggcaagtgt agccattaaa   32160 ttttggggggg atgtctttat aattttttta aattttata gccattaaaa atttaaaagc   32220
aaaatataaa ggaagaagaa tgagtggtga tttcccagac agctatcaga acagactata   32280
aagctacagt tattaaaaca gcactgcctt gcttctggat tacataaatt gaaggaggaa   32340
gtggagccgg gccctggcag ccttctcagt gtaactcagg accccgtgga cggggtgtct   32400
gagccagcag gaagagacag ggcctgctgc agaggacgta acaacagaac cacgcacctg   32460
cagcaaggca gtcccatctc cgtctcagct gagacacaga gcaaccaccc agctaggcag   32520
tcccatctca gctggagcac atccacgagg aatccaaatg cacacaaaaa aataaaagta   32580
caaaattcct ggaaggacat gtggggaatg tattcccgat attgggggg ccttaaagca    32640 tggcgcgaaa cacaagcatt gttaacggag tgtctgggag atttcactgt ttcaaaagga   32700
aacacttctt tattgaaaat cacagtaaaa aaatgacata gtacagattc agagaaaatg   32760
tttcttacaa atataacaat aaaaattaat atctctgata tccaaattga ttatacaaat   32820
caatagcagc tcagtagaaa aatggactaa acgtatgaat attaattctc acacttttta   32880
tggaataatg tttagaaaaa gaaaaacttt aaaattcaca gagggctaa gttttaggga    32940 atagttttga gtgtcatcta tatagttttt ctcaataaat atattaatgt agtaaattac   33000
attgagtgct tttatatttt aatttagttt ttcctaaatt gatctagata gatttttat    33060 caaaaatacc aggaatacat attaatcaac acaccaaaat atcaaaaata ttttttatta   33120
gataaattga ttctaaaatg tgtacaaagg ggcaaaggaa ctagaatagc taaatgataa   33180
aagaagaaga aaggaagaat cgtgcccctc aatgttaaga gttactcaaa agctcccgta   33240
atcaagagtg tcaccgtggg tgtgggcaca gcagctcatg catgtaatcc tagcactttg   33300
ggagcctgag gaaggaggat ctcttgaggc tagagttcta gacctgcctg ggctacatag   33360
tgagacctca tctctaaaat taaaaaaaaa aaattaatt aaaattaaaa aaatagaaaa    33420
ttgaaaaaga gagtgtcacc ccagggaaga gagagagtgg aggtaaaggg gcgtgcagac   33480
ccccaggatc acggccacct ggcctccac aagggaccaa gagccgtcaa tgccagaaga    33540
gccgctttcc caacaagcca tgctagagca gactcatggg ttcaaaaatg gccgtagacc   33600
tacacgttca tatgaaaatt aactcaaact ggggctgggc acagtggctc atgcctgtaa   33660
```

```
tcccagcact ttgggaggcc gaggctggca gatcacttga gatcgggagt tcgaaaccag   33720
cctggccaac atggtgaaac cctgtctcta tgaaaaatac aaaaattagc tgggcgtggt   33780
ggcaggcacc tgtaatccca gctacttggg aggctgaggc aggagaatcg cttgaaccca   33840
ggaggcagag gttgcagtga gccaagatca tgccactgca ctccagtctg gcaacagag   33900 agagactcgt ctcgaaataa ataaatacat taataaacaa aaattatcca ggcgtggtgg   33960
caggcacctg taatcccagc tacttgggag gctgagacat gagaatcatt taaacctggg   34020
ggttggaggt cgcagtgagc caagatcacg ccactgaact ccagcctggg agacagagta   34080
agactccgtc cccccccaaa aaaaaaaaaa agtaaaaat aaaggaaatt aactcaaatt    34140
ggatcaaaaa caataacact tttagaatag aagaaagtgt ccaggacctg ggcttggca    34200 aggacttcct agatataaca tcaaaagcat gattcatata tattttaaat caatgaatta   34260
gatctcattg aaattaaaaa cttttatgcc gtgaaagatc ctgttaggat ggatgaaaag   34320
ataagctgtg ggctgggaga aaatgtttgc aaaacccatg tctgacaaag gactcgtatc   34380
tagaatataa gaagaactct caaaactcaa cggaacaggg ccaaataatc caatgaaaga   34440
aggatcatgg agacaaggtg gagatggcag atgaagtcac aaaacggcct tcaacccgcg   34500
tggccccagg gaaacacagg ctgggaccat gacccaatat ttctccgtac ctattagaac   34560
agctaacgca aaatataata acaagaccaa atgctggcag agattcggag aaacggtatg   34620
acattcactg cgtgtggaat gtaacatggc gcacccacca tggaaaagag tttgacagtt   34680
tcttaaaaaa gcgaaacaga ctctgaccat ttgacccagc agtcacactc ctgggcattt   34740
gtcccagaga aagaaagatt tatgttcaca caaacaccta tacgtgattg ctcatggcag   34800
cgctatttgt aatagtcaaa agcttcagta ggtgaatggt aaacaaagag gtcctttcct   34860
accaggggag gctacttatc agtaaaaagg aactaactgt tgacacagga agcagcttag   34920
atggtctcaa gggcatgttc ctgagtgaag agctcatctg aaagggtccc acgcattcca   34980
tttacatcac atttgcaaaa tgacaaattt atagccatag gaaaaggcca gagggtgtga   35040
ggaggaagga acggggacat gggcagtgag tctctgggat gaggcagccc cggagatggc   35100
cgtggcagtg ggacagctct gtgtcctgtt cctggtggtg tgtacacaaa ttcccacatc   35160
ctacaacatg gcaaaaaccc agatacacac actgtagcac ggtcagcttc ctggcttaga   35220
cacgcactcc agctaaggga gacgaagccg ttgggaaaac tggttgaggg gcatgtggaa   35280
atctctgtac tagttttgag acttcctgtg aatctgtaat gatttcaaaa taaaatcttt   35340
aaagaaaatc acgagcttga taagagaat atacattgta tgctgccttt tgaataaaaa   35400
aaaaattaga catgcaggta ttccgttatt gttgcaaaca gaaaccacgg gaagaaggag   35460
acagaactca tggactcggt gagtggagaa cagaaagttt gagcgtctga ggttacttaa   35520
cgatttcaca tttaaaaatt atttaaatta agtaaaaaag gatacagaac acataaatgg   35580
aacacaagaa aacaaacaaa tgggcatttt caacgcataa atgttaagga gtggagaccg   35640
accaagagcc gccttgcacc gcaaatgggc cctgaggtcc agggctgcag gagcagggtg   35700
gggagcccgg ccagatggag gggcagacac cggcacccgc tgcctacgtc accgccctca   35760
gtgctgccca caagcgggtg ccccactggg tcccgccacc ccaaatccca gtgccggagc   35820
ggggcccggc tctgccaccc gctgccaccc ggtgtggcac ccaggccctg ctggcacaag   35880
gccacggcta atctgctctc agaggaagct gaggaggtga ggaggcagcc ctgccctcgg   35940
tgtttcccaa gcccccttat cccagcagat tcttctcggg gaagataagc tcccagctta   36000
```

```
gccagggcgg gtgggaagtc agagctgctt ccttaattgg cattttccag ttgagagcac   36060
attctctacc tttttcactt ggatcagcta attgccaaat gttttcattt ttgagaagaa   36120
gtaaaattgc agagatttgg gatttaggga aggaatgcaa ggatcaattt tgcctaatta   36180
cgaaatgtct cggcggtcac tgtgacgggt cccagagtcg gccgtgtgga ccccggggcc   36240
tcccgggcgg tggggggccg ggggctctga tgcagatgtt tacctgatgt cgtgggcctg   36300
aatctggttt acattggaaa tcagactgtt tacaggccag cacatctgcc tcttcctctg   36360
gctctccttc attctgctgt aatgttctgc aggtctcgct ggggtctctg tgggaatatc   36420
tgtgacacgg agtgagccag gccagcccgg ggcggcccca tccggggaca gcagctcacg   36480
gcctggcccc gcgtgcgcag ccggggcctg ggttggcggt ggagatgggg agggtctggg   36540
ggcccctggg tgggtggtgg gggtaccgtc agcccggctg cagggttcca gcggaggaca   36600
gggagccttc tccatccctg aaaaccatcg cggggacagt ggactcatca ggatgccggg   36660
accctctagt gtgttctgga agcagaggct gggtgtgggc acgggaacct gtgattgtcc   36720
ccagacaccg agaggcccac aggacccca gtgcccagac cccggctgca gatcgggggg   36780
tccagtcatg tgtcggggaa ggaggagggg agcaggggcc acagacaggg ggtccaggag   36840 ggcaggggt ccaggagggc agaggaccca ggacagcaaa gggtccggga gggcagagga   36900
tccaggagga caggggtcc agagggcag ggggtccagg agggcccagg agggcagggg   36960
gtccaggagg acagggggtc ctggaggca ggggtccag gagggcaggg ggtccaggag   37020
ggcagagggt ccaggagggc agaggtcca gagggccca ggagggcagg gggtccagga   37080 ggacagggg tcctggaggg caggggtcc aggaggcag ggggtccagg agggcagagg   37140
gtccaggagg gcccaggagg caggggtc caggaggaca gggggtcctg gagggcaggg   37200
ggtcccggag ggcagagggt cctggagggc aggggtccc ggaggcaga gggtcctgga   37260 gggcagggg tccaggaggg caggggtcc aggagggcag aggtcctgg agggcagggg   37320 gtccaggagg gcaggggtc caggagggcc aggagggaa gggggtccag gaggacaggg   37380
ggtccaggag ggcagagcca cagcaggctg ggtgctgctg ctacaggggg cttccccca   37440 gcagccccct gcactgcccc tctgacagcc tccacctttg accccaga acaatgggct   37500 gctgtggcgg ctctggaggc tgcggcccca gtcatggggc ctgcggctgc catgggctga   37560
gaccctgctg ctcttcgtgg agacactgat gtccttacca gatctcccgg gcccgccctc   37620
agcctccagg ctgaccaggc ttcctgggcc tcctaggaca cagccctggg tctcctcctc   37680
taggatactg gatgggaatc tgcggcttcc aacatccacc tgcccgcctt ccctctgcc   37740 ctgtccccttt gctgccatgg ccgcctttgt cctccctgga gattcagaga gcagccccgt   37800
tctcagttac ctggccttct gggtccttgg gaggttctga cctcttccca gcaggggcc   37860 tgggggctgc gtcctgcctg gtccaggcct tctcaccctc acctccctct gggctcaggg   37920
agctggggcc acacagccca gagaggctgg tctgcccagg acaggccacc ctcctcctgc   37980
tcccaggagt gcctgcagcc ctgtcagttt ccaagagtgt ctccttcaag cagcctcgtc   38040
aggtcgagcc accccagtg ccctctctcc tctggcagcc gcgctccctg cccttcctcc   38100
ccacctgctc agtcctgcaa agcctcctgc ctagctggac acctggggt tctgtatccc   38160 acactccagg ggcctccttc acatgtcggt gacctctgac actccagggg cctccttcac   38220
atgtcggtga cctctgaccg ctgttttcaga cccacagctc ctgggtgcac tcagccttgg   38280
gtcccgatgg caccagagtg ttccacgcct ggggcagcgc actcattgca gatctggcct   38340
gagactcagc agccgggcac cccatgagat ctactttctg aatggcgtcg tcacctgact   38400
```

```
gggcatacag gccacggacc ccatggtcat ttgggcactg acccctctca cacccccaa   38460
atcccacctg agagcagccc atcaggcagg ccccatatat tggatgcctc taagtatcag   38520
ccttgatgtc cctctaattc cagccctggt gtcttctccc tgggacaccc tgctgctccc   38580
tctagctgtg ccctccacgg tgactccaga catgcggatt cagcctcttc gctccaggac   38640
caaactcctc agcagctccc actactccca gcatgccatc cagctcctca gcccagcagc   38700
aaagacaggc acagaatggc tcccgaaccc atcgctccgg tccggagaag gagccctcca   38760
ccctccacgc tccattcgct gtcccctcgc gggccctgt gaggaacccc agccagaggc    38820
accaatggcc gccactgact tcaccctgt cctgaatcac aggaccaagg aggctgcccc    38880
gacaagggtc gcttccagac tcactccctg tcagccactg ccacatgcct gccgtgggca   38940
gcattggagg acagggggta ctctgtcagt cagcctaaca ggctggtccg tccttccttc   39000
cttccttcct tcttccctcc ctcacttcct tccttcttcc ctccctgcct ccctcccttc   39060
cttctctgct ccctccctcc ctcctccctc cccctccttc cctgcctccc tcctccctcc   39120
ttctctgcct ccttcctccc ccttccctcc cttccttcct tctctgctcc ccccctccct   39180
cttccctcc ctccctcttt ccctcccttc ctccctcctc ctcctccctc cctcccttcc    39240
ttccttcttt cttccttcc ttccttcctg cttctctccc ttcctccctc cctcacttcc    39300
ttccttcctt cttccctccc tgcctccctc ccttccttct ctgctccctc cctccccct    39360
tccctgcctc cctcttccct ccttctttgc ctcctccctc ccccttccct tccttccttc   39420
cttctctgct acctccctcc ctcctccctc cccctccct tccttccttc ctctctggtc    39480
aaatgcgggt acatgagagt tcccaccatc cccatggtaa gtgcacagtt ccgtggcatt   39540
gggaacctgc acgtggctgt gccactgtcg ccaccatgca gctccagcac cttttcatcg   39600
cgcgaaactg gagctccgtc ctgactaatc actcactccc atcggcctct gtcactggcc   39660
ctgctgacta ccattctgcc atcttcctct tgaatctgac tcctctgggg gccttccatc   39720
tgtgggtca cagcattggt cctattgtga ctggctggct tcactcggca cgaggctgtg   39780
aaggttggtg gcgttgctgc aggcgtcaga gcacactcct tttccaggct ccgtaagacc   39840
ccgatgtgtt tgtctacccc atttcagatc ccctcacctg ctgggttgtt tccacctttg   39900
ggctattgtg actgcacggc tgtgagcatg ggtgtctgag tccattctgt gtagccataa   39960
aagaacctct gtgatggggt aattcatcaa gctcacagtt ctgctggctg agaagttcaa   40020
tggcatggcc ctggcttctg ctggaggagg tcaaggggga agcagacacg ggaagagaga   40080
taaagctcag ggatgtcttg gcttcagaac aagcccact catgggaaca aatccattcc    40140
catgggaact caccctgtat cacaagagga gaatcactcc cagcaccacg gactccccag   40200
ggagtcactc ccacgaccca cacgtctccc tcccctcagg ccccacctcc ctacgctgcc   40260
acactggggg tcccgtttca acaagagttt tgctgggaac agatgcactg actacatcca   40320
ggtcgtggta agggctgtgc aagtatttga gtccctgctt tgatttcttt tggggataga   40380
cctaggaatg gaatggcggc ttcgcagggt aattttgtgt ttacctgttt ctggaaggag   40440
cacactgagc tggccagagc aggcttgtgt tttcctctgt gctccttcct gcttcccagg   40500
atgcagatga gatggcaggt gccccagcag ccctcgccaa ccataaggca tggattcctc   40560
accttcggct cggggagcac agagactgag ggccgtggac tcggggtgag atggtggcac   40620
ctccatcaca gacccacagt ctctgtgtcc agccttccg gaaagatgac agaaatgaaa    40680
agtctgcctt atggaagaca aggttattca gaatttcgg ttctgtatgg tctccttaga    40740
```

| | | | | | |
|---|---|---|---|---|---|
| aacattagca | gactttaaaa | aatgaaaata | gcccatgttc | attgtgaaaa | agtgagccat 40800 |
| ggcctccggg | gcaccggagc | cacagagcca | ccacgctttg | cttttgtttc | tcactcccct 40860 |
| actctcccca | cataggcacc | gacgctttcc | ctgacagcat | catcatcacc | caactagggc 40920 |
| agctgacccg | cgtcttcctc | acgacgtgga | atggtttgag | tcaagggttt | tcatggccat 40980 |
| gagccacgtg | gaggctgtgc | cttttgtttc | ctgtgagaaa | tcttcaacca | gcgccactct 41040 |
| cagcctcccc | tctgccagcg | cttctgtggc | tgcacctgca | ttcgtgggct | gtggctgcga 41100 |
| agcacaggaa | taattgatgg | ctctggggca | ctttgctggg | ctgcttccag | aaaagttgac 41160 |
| ccctccctgc | aaaccagcac | tgcccagcat | tcttgtcccg | ccaagcctga | ctgtgagctg 41220 |
| ttgtgacgtt | gccactttgc | tcggaaagga | cccttacct | tttatttccc | ttgcatttct 41280 |
| ttcaattcta | ccattgacca | tttctcatac | gtgtggtcat | cattgtattt | cgcccccatt 41340 |
| ttgtgaggtt | tagtgtattc | ttaaagtttc | ctgggttttg | atgagagcat | attctgtcat 41400 |
| tatatttaac | aggtgttttc | cccagcttgg | atgtgtttgg | ccattagctt | cttttctgct 41460 |
| attttacact | agtctgttat | tcttcactac | aaaaggactc | tgccgagggt | ccccatgctc 41520 |
| cccatgcttc | ggggtgtgag | gtagcagggg | aaggcaggtg | tccttccttc | tttgaagtgc 41580 |
| gggttggggc | aggacagcag | accctggggt | cactgctgag | gaggggaagg | atgggattag 41640 |
| gactgttctc | ttcctggcct | catgagctcc | cccagctcct | tctggtggtt | ggagaagaaa 41700 |
| cctcctgatt | gtcacggaga | gtgagtttgt | ccgtggagct | tttcctgcac | ggctcacata 41760 |
| gaacgggctg | tgaggtccct | ccactgagca | gcacgtgcca | ggccgggtgc | ccacgactgt 41820 |
| tgggaaaacc | caggcctgta | ttccaggaag | caaaggtctt | tagatgaagg | ttttaagaat 41880 |
| gaaaattaac | ccacagaatg | gtgaggtcag | ttggagcctg | gattccatgg | ggtaagacag 41940 |
| ccacagccag | gtgggcatcc | tgctccttcc | ctttcccctg | tccctgccca | ccggccatgc 42000 |
| cctagagtag | gggcacactc | ggaccccagc | ccagcgccca | cccatgctgc | ctgcaggcct 42060 |
| gcgaggtccc | acaaccccctt | ggcatgcagc | gacagcccgg | ggccaggtgt | gggtgaggct 42120 |
| tgggatttcc | tggcacagct | gacttcatgt | tgtggcctgg | cagcctcggg | tggtgtcggc 42180 |
| agatgcagga | agccacgggc | gcagctccct | gcctgtcccg | gccgtgggtg | ctaatgcaga 42240 |
| gtgggttctg | tggctggtca | cacaggcagc | cgggtgggtg | caggtcatcc | cggggatggc 42300 |
| cttgcactgt | ctgatccccg | gggaggggag | ggtcttttcg | ctgaccacgc | tgtttgctgc 42360 |
| gtgcttttttg | tttgccaagg | gctgcaatgt | ttgtcgtctg | ccgcagtgtt | tgctgccggg 42420 |
| tgaagaatcg | ctggccctgt | gttgtcacct | gggcccaccg | tgacaaggtc | cccacctctg 42480 |
| ttgtgggact | cgggggcaaa | gttccctgct | gttcacgctg | caagtgacaa | gggccttggt 42540 |
| ctctgaacca | ggagcctctg | agtcctgccc | cacaggctg | agccctggct | gggagcaatg 42600 |
| ttctttgggg | gagacagcag | cttcctcact | tccatgtaca | gccagatgcc | acgggatgtg 42660 |
| gggagtgcga | cagggccgtg | gggagtgtga | caaggccttg | gggagtgtga | cagggctgtg 42720 |
| gggagtgtga | cagggccttg | gggagtttga | cagggccgtg | gggagtgtga | cagagccgtg 42780 |
| gggagtggga | caaggccgtg | gggagtggga | cagggccgtg | gggaatggga | cagggccgtg 42840 |
| gggagtgtga | cagggccatg | gggagtttga | cagggccgtg | gggagtggga | cagggctgtg 42900 |
| gggagtgcga | caggtctgtg | gcgagtgtga | cagggctgtg | gggagtgcga | cagggctgtg 42960 |
| gggagttttg | aaagggccat | ggggagtttt | gacagggctg | tgcggagtgt | gacagggctg 43020 |
| tgcggagtgt | gacagggatg | tggggagtgc | gacagggctg | tggggagtgt | gacagggctg 43080 |
| tggggagtgt | gacagggctg | tgggaagtgc | gacaggtctg | tggcgagtgt | gacagagctg 43140 |

```
tggggagtgc aacaggtctg tggcgagtgt gacagagctg tggggagttt tgacacgtct   43200
gtggggagtg caacagggct gtggggagtg tgacagggct gtggggagtg cgacagggct   43260
gtggggaatg tgacggggct gtgtgggagc aggtggtcct gtgggcatc ccggggtctg    43320 tgctcaggct gtgggaggtg gggctggcag gggatcctgg agaaacacct ttggggctc    43380 aggtttggtg gagctcccac ttccacagtg gctctgagtg gggcctgagc aggttttcct   43440
ggcagtggct gagggtgggt gggcctggta ggtactgggc tgctcagaag ccagccagct   43500
ccatgttgcc cacctcagcc tcccaggctt ctcagggccc agctgtgctc tgtccctggg   43560
gcccttccct ccccggacac tgctcacccc tggcaagggc tctgccctgg acacacccct   43620
gctagaccct cagatctgat cccagccctt cccatgtgac tccctgggtg ctcccagatg   43680
actgggatgt ggggaaggat caaagagcac tttggttgtc tctgtaactc ttctagtgat   43740
tagataaggg ctggatttaa ggattacttc tgcaatgcaa atagatgaaa ggaacaagct   43800
aaataacaaa ctcttcccat tcccagaaca aagtcagctc tggcctggtt ccacgtgccc   43860
tgtccagcac gtcccccaag cgcaggcatg gcccccgga ccagccgcgg acccctcctc     43920
gcgctttgca acgcctcaca gctggcccg caccccctggg gcaggaccac tccctcttct    43980
tattcttctc tgtgtcacct tcccagactc tgcacatagt cggcgctaca taaatggtgg   44040
ctgcaaaaag gagacgagca gcagagcaat gccccaggga acaagagggg cgctgttgcc   44100
aaggccaggg ccagggtatc tgccctgagg cctgagcccc acacgaccca gggctccaga   44160
gccccatggc ccatctcact gctggggctg aaccccagg gccctgcag ccactgcctc       44220 aggaggtcag gttggggtgt ggagtaggag ggacgggtgt ttccagggaa tccctgtgta   44280
ggtgggatcc agagggcttg aaaccctcaa gctaccagcc agctccacgc ctaggacagg   44340
ccttattaga gttcaggatc tgccagctcc caggggcagc ctcaatgtcc ggggtggatg   44400
ggggtttctg tgggttcact tctgccccca gctgggatgc ctggaaggag agctcaggga   44460
cagtgtggcc agaccctgac ccagacagaa gattctgtct gagagaccgg ggaccttcac   44520
agagggacag aggcccagga agcagcggct gctgctgtaa gcctacggcg agagccatgg   44580
tcacagaaga cccacttgtt gccaggcgtt ttgccttcac aatggcaaag tctcccagtg   44640
gcccaggaga aaagggaatg ctcattccat tctgcctgcc agaaaacaga ggctgaggcc   44700
cagaggctca ggcaacctcc ccaggttcac ctcatttgga aacagcccct tcccatcccc   44760
ggttgctgcc gcaatcttct aaggggactt cctcagaggt cattaaatgc attgaaaact   44820
ggttctggtc ctcgacccta agctgctgga ggaggggtg tgggagcaga ttcggggtgc     44880
acctgtgtgt tcaggtgaag gcggagggaa attagtcatg gagctaagct gaaccacctg   44940
ctgggcccca gcaggcaag gccctgtggg caggtgggaa gccagaggcc gcctctcacc      45000
ccggggaggg gcaggggctg gagtgacggt gcagggtgag attttggcca ggcacaactc   45060
catccatccc tgcatcccca ggaagccaca gacacccagg ttctgagagc ccggctctcg   45120
aatgtccctc ctcccccgac ctccttcggt gcccctggcc atgccagccc tgagcatgaa   45180
gccttcaact ttcccacgca cccacttcca ctctccaggg ctgaggagca ggaaggagat   45240
ggcttggagg ggtgagcccc tgtcctgttc tcagagggtc acagctactc actacctgct   45300
acgaagacag ggaagggtgg gagccgttct aaaccagcat cagtgcatgc cacaaaatag   45360
aagccgtgca ttacaaacta gaaacgaggg cttggttgca ggcaccttcc ctagagaccc   45420
tggctgagca gaggctgggg tctggctgcg ctgctctgac ggtgtgcacg ggcgggctag   45480
```

```
gcactcgccc tgagtcccag aaagaggagc ccacagatac aaaacttaaa ggatgtgtta  45540 tttatttt   taatttaatt tttgtttttt caaaagcatc aaagtcattg tgattggaag   45600
gaatgcgcaa gttggtctgg ggtgctgtcc ctgggcgccg aaccagccgg ggacatggcc   45660
cctggagagc tgccgacccc ggggctaggg gagtggtctt gcgaggagcc tttgcttccc   45720
actcgccggc cgccccgcgg ggccctcctg ccaccaggtg gcgcttctcg gccagcccgg   45780
gccgcaggac ctgcagtctc gtttccccag gaatggcgac ggccctgtta ttcccatcac   45840
aattttacag gtcagaaaag gagactcgga gtgcatatat agcaacttgg agaaagtcgc   45900
aagggacgaa ggaccctccc ccggacacag gaaccttctg ggggatgggg acagggactc   45960
aggtgcagag aaaaccagag ctgctaccgt ggggacagaa agggagtcta cccagagaca   46020
gcagaggcag gagctgcccc ccctctttgc ccccagtggc cccgagcgag gggttgccac   46080
cacctagagc ctggggacca ggggccagtg cctggggacg gaggccgtgg tcgagacagg   46140
cgagggatgt ggcggagaca gggaggccca ggtcggctgg cacagggcaa ggagcaggcg   46200
agccgacccc agggccttgc ccttgtcacg cccctgcca  tgttcctgct ggcccccttc   46260
ctgttctgtg aggtcaacac gcaggagaaa ggggcagaag ggaaggtctc cccacaccga   46320
gggctctgcc cgcttgggcc aggggttggg gggtggtcat ggcaccaggg ctgctctgag   46380
ctacagcccc gagggggggc cgggcgatgc ctcctcctcc gtgccagcct gtgccggggc   46440
ccctaggaac ccccaagtcc ctgcctgtga cctctgcaga gcccagcagg cgcctccccg   46500
ccctcggcca caggctcgga gctcacggcc cccaggggc  gctcaaggac tgctcatctg    46560
cgcttctgcc gcgggcagct ctgacccctc ccgctgcgct cctccagccg catccctgca   46620
gccttgggcc ctactggccc gggggaggag gcactgcgct ttggggagga agagagacta   46680
aaggggagac cgagaacccc gggtcaggaa gcggagagct aaaacgacaa ccgtgggtca   46740
gcggaggccg gcaacttcat ttcatgacct ctggc                              46775
```